US009200061B2

(12) United States Patent
Tesar et al.

(10) Patent No.: US 9,200,061 B2

(45) **Date of Patent: *Dec. 1, 2015**

(54) GENERATION AND PROFILING OF FULLY HUMAN HUCAL GOLD®-DERIVED THERAPEUTIC ANTIBODIES SPECIFIC FOR HUMAN CD3I

(75) Inventors: Michael Tesar, Weilheim i. Ob. (DE); Ute Jaeger, Munich (DE)

(73) Assignee: Morpho Sys AG, Planegg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/302,195

(22) Filed: Nov. 22, 2011

(65) Prior Publication Data

US 2012/0076782 A1 Mar. 29, 2012

Related U.S. Application Data

(63) Continuation-in-part of application No. 10/588,568, filed as application No. PCT/IB2005/002476 on Feb. 7, 2005, now Pat. No. 8,263,746, application No. 13/302,195, which is a continuation of application No. 11/920,830, filed as application No. PCT/EP2006/004991 on May 24, 2006, now abandoned.

(60) Provisional application No. 60/541,911, filed on Feb. 6, 2004, provisional application No. 60/547,584, filed on Feb. 26, 2004, provisional application No. 60/553,948, filed on Mar. 18, 2004, provisional application No. 60/599,014, filed on Aug. 6, 2004, provisional application No. 60/614,471, filed on Oct. 1, 2004, provisional application No. 60/683,772, filed on May 24, 2005, provisional application No. 60/706,004, filed on Aug. 8, 2005.

(51) Int. Cl.

| | |
|---|---|
| ***A61K 39/395*** | (2006.01) |
| ***C07K 16/00*** | (2006.01) |
| ***C07K 16/28*** | (2006.01) |
| ***C12N 9/24*** | (2006.01) |
| *A61K 39/00* | (2006.01) |

(52) U.S. Cl.

CPC ........... *C07K 16/005* (2013.01); *C07K 16/2896* (2013.01); *C12N 9/2497* (2013.01); *C12Y 302/02005* (2013.01); *A61K 2039/505* (2013.01); *C07K 2317/21* (2013.01); *C07K 2317/24* (2013.01); *C07K 2317/33* (2013.01); *C07K 2317/34* (2013.01); *C07K 2317/55* (2013.01); *C07K 2317/56* (2013.01); *C07K 2317/565* (2013.01); *C07K 2317/732* (2013.01); *C07K 2317/734* (2013.01); *C07K 2317/74* (2013.01); *C07K 2317/75* (2013.01); *C07K 2317/92* (2013.01); *C07K 2319/30* (2013.01)

(58) Field of Classification Search

CPC ........... C07K 16/2896; C07K 2316/95; C07K 236/96; C07K 2317/70; C07K 2317/21; C07K 2317/71–2317/734; C07K 2317/24; C07K 16/40; C07K 2317/34

See application file for complete search history.

(56) References Cited

U.S. PATENT DOCUMENTS

| | | | | |
|---|---|---|---|---|
| 5,545,405 | A | 8/1996 | Page | |
| 6,300,064 | B1 | 10/2001 | Knappik et al. | |
| 7,084,257 | B2 | 8/2006 | Deshpande et al. | |
| 7,091,323 | B2 | 8/2006 | Pan et al. | |
| 7,223,397 | B1 | 5/2007 | Rosenblum et al. | |
| 7,262,278 | B2 | 8/2007 | Tawara et al. | |
| 7,794,719 | B2 | 9/2010 | Bardroff et al. | |
| 8,362,211 | B2 * | 1/2013 | Elias et al. | 530/387.1 |
| 2002/0164788 | A1 | 11/2002 | Ellis et al. | |
| 2003/0211553 | A1 | 11/2003 | Logtenberg et al. | |
| 2004/0141982 | A1 | 7/2004 | Lust et al. | |
| 2007/0031406 | A1 * | 2/2007 | Zand et al. | 424/144.1 |
| 2009/0123950 | A1 * | 5/2009 | Tesar | 435/7.23 |
| 2010/0172907 | A1 | 7/2010 | Bardroff et al. | |
| 2010/0285004 | A1 * | 11/2010 | Tesar et al. | 424/133.1 |
| 2012/0052078 | A1 * | 3/2012 | Tesar et al. | 424/173.1 |
| 2012/0189622 | A1 * | 7/2012 | Tesar et al. | 424/133.1 |

FOREIGN PATENT DOCUMENTS

| | | | |
|---|---|---|---|
| EP | 1 174 440 | A1 | 1/2002 |
| EP | 1 720 907 | A2 | 11/2006 |
| WO | WO 94/17184 | A1 | 8/1994 |
| WO | WO 96/16990 | A1 | 6/1996 |
| WO | WO 99/62526 | A2 | 12/1999 |

(Continued)

OTHER PUBLICATIONS

Nuckel et al., Eur J. Pharmacol 2005; 514:217-224.*
Stanglmaier et al. Ann Hematol. 2004; 83:634-645.*
Genmab Dec. 2013 Post ASH Seminar, pp. 1 and 70-73.*
Deckert et al., Clin. Cancer Res. 2014; 20:4574-83.*
U.S. Appl. No. 10/588,568, filed Oct. 14, 2009, Michael Tesar et al.
U.S. Appl. No. 11/920,830, filed Nov. 21, 2007, Michael Tesar et al.
U.S. Appl. No. 12/089,806, filed Oct. 12, 2006, Tesar et al.
Antonelli et al., "Human anti-CD38 autoantibodies raise intracellular calcium and stimulate insulin release in human pancreatic islets," Diabetes, May 2001, 50:985-991.
Ausiello et al., "Functional topography of discrete domains of human CD38," Tissue Antigens, Dec. 2000, 56(6):539-547.

(Continued)

*Primary Examiner* — Sheela J Huff
*Assistant Examiner* — Jessica H Roark
(74) *Attorney, Agent, or Firm* — Paul F. Wiegel

(57) ABSTRACT

The present invention provides methods for using recombinant antigen-binding regions and antibodies and functional fragments containing such antigen-binding regions that are specific for CD38, which plays an integral role in various disorders or conditions. These methods take advantage of newly discovered antibodies and surprising properties of such antibodies, such as the ability to bind CD38 of minipig origin and the ability to induce, by cross-linking, specific killing of cells that express CD38. These antibodies as well as the methods for using those antibodies can be used to treat, for example, hematological malignancies such as multiple myeloma.

15 Claims, 30 Drawing Sheets

(56) References Cited

FOREIGN PATENT DOCUMENTS

| | | | |
|---|---|---|---|
| WO | WO 00/40265 | A1 | 7/2000 |
| WO | WO 00/48631 | A2 | 8/2000 |
| WO | WO 01/05950 | A2 | 1/2001 |
| WO | WO 02/06347 | A1 | 1/2002 |
| WO | WO 02/32288 | A2 | 4/2002 |
| WO | WO 03/070760 | A2 | 8/2003 |
| WO | WO 2004/003019 | A2 | 1/2004 |
| WO | WO 2005/042019 | A1 | 5/2004 |
| WO | WO 2005/087806 | A2 | 9/2005 |
| WO | WO 2005/103083 | A2 | 11/2005 |
| WO | WO 2006/088951 | A2 | 8/2006 |
| WO | WO 2006/099875 | A1 | 9/2006 |
| WO | WO 2006/110581 | A2 | 10/2006 |
| WO | WO 2006/125640 | A2 | 11/2006 |
| WO | WO2008/047242 | A2 * | 4/2008 |

OTHER PUBLICATIONS

Bollen et al., "The Goettingen Minipig in pharmacology and toxicology" Pharmacology and Toxicology, vol. 80, No. Suppl. 2, 1997, pp. 3-4, XP009075772 & Workshop and Symposium on Anaesthesia and Experimental Surgery and Research Application of Minipigs; Odense, Denmark; Jun. 11-12, 1996 ISSN: 0901-9928.
Brorson et al., "Mutational Analysis of Avidity and Fine Specificity of Anti-Levan Antibodies," J. Immunol., 1999, 163:6694-6701.
Brummel et al., "Probing the combining site of an anti-carbohydrate antibody by saturation-mutagenesis: role of the heavy-chain CDR3 residues," Biochemistry, 1993, 32:1180-1187, PubMed abstract, 2 pages.
Burgess et al., "Possible dissociation of the heparin-binding and mitogenic activities of heparin-binding (acidic fibroblast) growth factor-1 from its receptor binding activities by site directed mutagenesis of a single lysine residue," Journal of Cell Biology, 1990, 111:2129-2138.
Burks et al., "In vitro scanning saturation mutagenesis of an antibody binding pocket," Proc. Natl. Acad. Sci. USA, Jan. 1997, 94:412-417.
Casset et al., "A peptide mimetic of an anti-CD4 monoclonal antibody by rational design," Biochemical and Biophysical Research Communications, 2003, 307:198-205.
Chamow et al., "A Humanized, bispecific immunoadhesin-antibody that retargets CD3+ effectors to kill HIV-1-infected cells," J. Immunol., Nov. 1, 1994, 153(9):4268-4280.
Chen et al., "Selection and Analysis of an Optimized Anti-VEGF Antibody: Crystal Structure of an Affinity-matured Fab in Complex with Antigen," J. Mol. Biol., 1999, 283:865-881.
Colman, P.M., "Effects of amino acid sequence changes on antibody-antigen interactions," Research in Immunol., 1994, 145:33-36.
DePascalis et al,. "Grafting of 'Abbreviated' Complementarity-Determining Regions Containing Specificity-Determining Residues Essential for Ligand Contact to Engineer a Less Immunogenic Humanized Monoclonal Antibody," J. Immunol., 2002, 169:3076-3084.
Deshpande et al., "Cloning and functional characterization of cDNA encoding porcine CD38" FASEB Journal, vol. 18, No. 4-5, 2004, pp. Abst. 842.4, URL—http://ww, XP009075817 & FASEB Meeting on Experimental Biology: Translating the Genome; Washington, District of Columbia, USA; Apr. 17-21, 2004 ISSN: 0892-6638.
Dufner et al., "Harnessing phage and ribosome display for antibody optimization," Trends in Biotechnology, 2006, 24(11):523-529.
Ellis et al., "Engineered anti-CD38 monoclonal antibodies for immunotherapy of multiple myeloma," Journal of Immunology, The Williams and Wilkins Co. Baltimore, US, vol. 155, No. 2, 1995, pp. 925-937, XP002146232 ISSN: 0022-1767.
Ferrero et al., "Characterization and phylogenetic epitope mapping of CD38 ADPR cyclase in the cynomolgus macaque," BMC Immunology, vol. 5, Sep. 2004, 13 pages, XP002410155 ISSN: 1471-2172.
Flavell et al., "Therapy of human T-cell acute lymphoblastic leukaemia with a combination of anti-CD7 and anti-CD38-saporin immunotoxins is significantly better than therapy with each individual immunotoxin," Br. J. Cancer., 2001, 84(4):571-578.
Funaro et al., "Involvement of the multilineage CD38 molecule in a unique pathway of cell activation and proliferation," J. Immunol., Oct. 15, 1990, 145(8):2390-2396.
Holm et al., "Functional mapping and single chain construction of the anti-cytokeratin 8 monoclonal antibody TS1," Molecular Immunology, 2007, 44:1075-1084.
Hoshino et al. "Mapping of the Catalytic and Epitopic Sites of Human CD38/$NAD^+$ Glycohydrolase to a Functional Domain in the Carboxyl Terminus," J. Immunol., 1997, 158(2):741-747.
Jackson et al., "Isolation of a cDNA encoding the human CD38 (T10) molecule, a cell surface glycoprotein with an unusaul discontinuous pattern of expression during lymphocyte differentiation," J. Immunol., Apr. 1, 1990, 144(7):2811-2815.
Jang et al., "The structural basis for DNA binding by an anti-DNA autoantibody," Molecular Immunology, 1998, 35:1207-1217.
Knappik et al., "Fully synthetic human combinatorial antibody libraries (HuCAL) based on modular consensus frameworks and CDRs randomized with trinucleotides," J. Mol. Biol., 2000, 296:57-86.
Kobayashi et al., "Tryptophan H33 plays an important role in pyrimidine (6-4) pyrimidone photoproduct.binding by a high-affinity antibody," Protein Engineering, 1999, 12(10):879-884.
Konopleva et al., "Ligation of Cell Surface CD38 Protein with Agonistic Monoclonal Antibody Induces a Cell Growth Signal in Myeloid Leukemia Cells," J. Immunol., 1998, 161:4702-4708.
Krebs et al., "High-throughput generation and engineering of recombinant human antibodies," J. Immunol. Methods, 2001, 254:67-84.
Kretzschmar et al., "Antibody discovery: phage display," Current Opinion in Biotechnology, 2002, 13:598-602.
Kumar et al., "Molecular Cloning and Expression of the Fabs of Human Autoantibodies in *Escherichia coli*," J. Biol. Chem., 2000, 275:35129-35136.
Lazar et al., "Transforming growth factor alpha: mutation of aspartic acid 47 and leucine 48 results in different biological activities," Molecular and Cellular Biology, 1988, 8:1247-1252.
MacCallum et al., "Antibody-antigen Interactions: Contact Analysis and Binding Site Topography," J. Mol. Biol., 1996, 262:732-745.
Malavasi et al., "Characterization of a murine monoclonal antibody specific for human early lymphohemopoietic cells," Hum. Immunol., Jan. 1984, 9(1):9-20.
Maloney et al., "Antibody Therapy for Treatment of Multiple Myeloma," Seminars in Hematology, Jan. 1999, 36(1):Suppl 3:30-33, XP000857401 ISSN: 0037-1963.
Marchetti et al., "Prolonged In Vitro Exposure to Autoantibodies Against CD38 Impairs the Function and Survival of Human Panceratic Islets," Diabetes, Dec. 2002, 51(Supp.3):S474-S477.
Mehta et al., "Retinoic acid-induced CD38 antigen as a target for immunotoxin-mediated killing of leukemia cells," Mol. Cancer Ther., 2004, 3:345-352.
Namba et al., "Establishment of five human myeloma cell lines," In Vitro Cell. & Dev. Biol., Aug. 1989, 25(8):723-729.
Nata et al. "Human gene encoding CD38 (ADP-ribosyl cyclase/cyclic ADP-ribose hydrolase): organization, nucleotide sequence and alternative splicing," Gene, 1997, 186(2):285-292.
Reinherz et al., "Discree stages of human intrathymic differentiation: Analysis of normal thymocytes and leukemic lymphoblasts of T-cell lineage," PNAS USA, Mar. 1980, 77(3):1588-1592.
Rudikoff et al., "Single amino acid substitution altering antigen binding specificity," PNAS, 1982, 79:1979-1983.
Skolnick et al., "From genes to protein structure and function: novel applications of computational approaches in the genomic era," Trends in Biotechnology, 2000, 18:34-39.
Smith-Gill et al., "Contributions of Immunoglobulin Heavy and Light Chains to Antibody Specificity for Lysozyme and Two Haptens," J. Immunol., Oct. 15, 1987, 139:4135-4144.
Song et al., "Light Chain of Natural Antibody Plays a Dominant Role in Protein Antigen Binding," Biochemical and Biophysical Research Communications, 2000, 268:390-394.
Stein et al., Clinical Cancer Research, Apr. 15, 2004, 10:2868-2878.

(56) References Cited

OTHER PUBLICATIONS

Stevenson et al., "Preliminary Studies for an Immunotherapy Approach to the Treatment of Human Myeloma Using Chimeric Anti-CD38 Antibody," Blood, Mar. 1, 1991, 77(5):1071-1079, XP000930093 ISSN: 006-4971.
Vajdos et al., "Comprehensive Functional Maps of the Antigen-binding Site of an Anti-ErbB2 Antibody Obtained with Shotgun Scanning Mutagenesis," J. Mol. Biol., 2002, 320:415-428.
Ward et al., "Binding activities of a repertoire of single immunoglobulin variable domains secreted from *Escherichia coli*," Nature, 1989, 341:544-546.
Wu et al. "Humanization of a Murine Monoclonal Antibody by Simultaneous Optimization of Framework and CDR Residues," J. Mol. Biol., 1999, 294:151-162.
Zhou et al., "Optimization of primer sequences for mouse scFv repertoire display library construction," Nucleic Acids Res., 1994, 22(5):888-889.
Zocchi et al., "A single protein immunologically identified as CD38 displays NAD+ glycohydrolase, ADP-ribosyl cyclase and cyclic ADP-ribose hydrolase activities at the outer surface of human erythrocytes," Biochemical and Biophysical Research Communications, Nov. 15, 1993, 196(3):1459-1465, XP002410154 ISSN: 0006-291X.

* cited by examiner

Figure 1a

Variable Heavy Chain DNA

3077_VH1B (SEQ ID NO: 1):

(1) CAGGTGCAAT TGGTTCAGAG CGGCGCGGAA GTGAAAAAAC CGGGCGCGAG
(51) CGTGAAAGTG AGCTGCAAAG CCTCCGGATA TACCTTTACT TCTTATTCTA
(101) TTAATTGGGT CCGCCAAGCC CCTGGGCAGG GTCTCGAGTG GATGGGCTAT
(151) ATCGATCCGA ATCGTGGCAA TACGAATTAC GCGCAGAAGT TTCAGGGCCG
(201) GGTGACCATG ACCCGTGATA CCAGCATTAG CACCGCGTAT ATGGAACTGA
(251) GCAGCCTGCG TAGCGAAGAT ACGGCCGTGT ATTATTGCGC GCGTGAGTAT
(301) ATTTATTTTA TTCATGGTAT GCTTGATTTT TGGGGCCAAG GCACCCTGGT
(351) GACGGTTAGC TCA

3079_VH3 (SEQ ID NO: 2):

(1) CAGGTGCAAT TGGTGGAAAG CGGCGGCGGC CTGGTGCAAC CGGGCGGCAG
(51) CCTGCGTCTG AGCTGCGCGG CCTCCGGATT TACCTTTTCT AATTATGGTA
(101) TGCATTGGGT GCGCCAAGCC CCTGGGAAGG GTCTCGAGTG GGTGAGCAAT
(151) ATCCGTTCTG ATGGTAGCTG GACCTATTAT GCGGATAGCG TGAAAGGCCG
(201) TTTTACCATT TCACGTGATA ATTCGAAAAA CACCCTGTAT CTGCAAATGA
(251) ACAGCCTGCG TGCGGAAGAT ACGGCCGTGT ATTATTGCGC GCGTCGTTAT
(301) TGGTCTAAGT CTCATGCTTC TGTTACTGAT TATTGGGGCC AAGGCACCCT
(351) GGTGACGGTT AGCTCA

3080_ VH3 (SEQ ID NO: 3):

(1) CAGGTGCAAT TGGTGGAAAG CGGCGGCGGC CTGGTGCAAC CGGGCGGCAG
(51) CCTGCGTCTG AGCTGCGCGG CCTCCGGATT TACCTTTTCT TCTTATGGTA
(101) TGCATTGGGT GCGCCAAGCC CCTGGGAAGG GTCTCGAGTG GGTGAGCAAT
(151) ATCTATTCTG ATGGTAGCAA TACCTTTTAT GCGGATAGCG TGAAAGGCCG
(201) TTTTACCATT TCACGTGATA ATTCGAAAAA CACCCTGTAT CTGCAAATGA
(251) ACAGCCTGCG TGCGGAAGAT ACGGCCGTGT ATTATTGCGC GCGTAATATG
(301) TATCGTTGGC CTTTTCATTA TTTTTTTGAT TATTGGGGCC AAGGCACCCT
(351) GGTGACGGTT AGCTCA

3100_VH 3 (SEQ ID NO: 4):

(1) CAGGTGCAAT TGGTGGAAAG CGGCGGCGGC CTGGTGCAAC CGGGCGGCAG
(51) CCTGCGTCTG AGCTGCGCGG CCTCCGGATT TACCTTTTCT TCTAATGGTA
(101) TGTCTTGGGT GCGCCAAGCC CCTGGGAAGG GTCTCGAGTG GGTGAGCAAT
(151) ATCTCTTATC TTTCTAGCTC TACCTATTAT GCGGATAGCG TGAAAGGCCG
(201) TTTTACCATT TCACGTGATA ATTCGAAAAA CACCCTGTAT CTGCAAATGA
(251) ACAGCCTGCG TGCGGAAGAT ACGGCCGTGT ATTATTGCGC GCGTTTTTAT
(301) GGTTATTTTA ATTATGCTGA TGTTTGGGGC CAAGGCACCC TGGTGACGGT
(351) TAGCTCA

3077_1_VH1B (SEQ ID NO: 31):

(1) CAGGTGCAAT TAGTCCAAAG TGGTGCGGAA GTGAAAAAAC CGGGCGCGAG
(51) CGTGAAAGTG AGCTGCAAAG CCTCCGGATA TACCTTTACT TCTTATTCTA
(101) TTAATTGGGT CCGCCAAGCC CCTGGGCAGG GTCTCGAGTG GATGGGCTAT
(151) ATCGATCCGA ATCGTGGCAA TACGAATTAC GCGCAGAAGT TTCAGGGCCG
(201) GGTGACCATG ACCCGTGATA CCAGCATTAG CACCGCGTAT ATGGAACTGA
(251) GCAGCCTGCG TAGCGAAGAT ACGGCCGTGT ATTATTGCGC GCGTGAGTAT

Figure 1a (Continued)

```
(301) ATTTATTTTA TTCATGGTAT GCTTGATTTT TGGGGCCAAG GCACCCTGGT
(351) GACGGTTAGC TCA
```

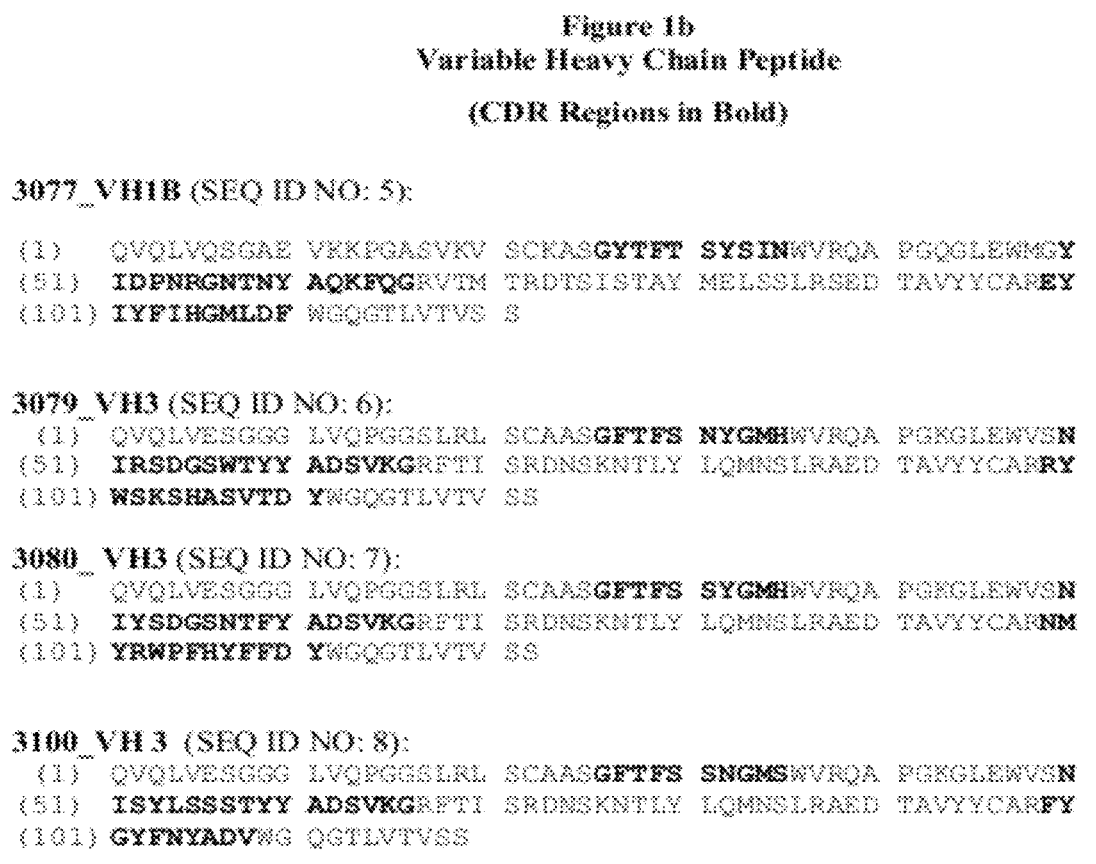

Figure 1b
Variable Heavy Chain Peptide

(CDR Regions in Bold)

3077_VH1B (SEQ ID NO: 5):

(1) QVQLVQSGAE VKKPGASVKV SCKASGYTFT SYSINWVRQA PGQGLEWMGY
(51) IDPNRGNTNY AQKFQGRVTM TRDTSISTAY MELSSLRSED TAVYYCAREY
(101) IYFIHGMLDF WGQGTLVTVS S

3079_VH3 (SEQ ID NO: 6):
(1) QVQLVESGGG LVQPGGSLRL SCAASGFTFS NYGMHWVRQA PGKGLEWVSN
(51) IRSDGSWTYY ADSVKGRFTI SRDNSKNTLY LQMNSLRAED TAVYYCARRY
(101) WSKSHASVTD YWGQGTLVTV SS

3080_ VH3 (SEQ ID NO: 7):
(1) QVQLVESGGG LVQPGGSLRL SCAASGFTFS SYGMHWVRQA PGKGLEWVSN
(51) IYSDGSNTFY ADSVKGRFTI SRDNSKNTLY LQMNSLRAED TAVYYCARNM
(101) YRWPFHYFFD YWGQGTLVTV SS

3100_VH 3 (SEQ ID NO: 8):
(1) QVQLVESGGG LVQPGGSLRL SCAASGFTFS SNGMSWVRQA PGKGLEWVSN
(51) ISYLSSSTYY ADSVKGRFTI SRDNSKNTLY LQMNSLRAED TAVYYCARFY
(101) GYFNYADVWG QGTLVTVSS

Figure 2a

Variable Light Chain DNA

3077_Vk kappa 2 (SEQ ID NO: 9):

```
(1)   GATATCGTGA TGACCCAGAG CCCACTGAGC CTGCCAGTGA CTCCGGGCGA
(51)  GCCTGCGAGC ATTAGCTGCA GAAGCAGCCA AAGCCTGCTT TTTATTGATG
(101) GCAATAATTA TCTGAATTGG TACCTTCAAA AACCAGGTCA AAGCCCGCAG
(151) CTATTAATTT ATCTTGGTTC TAATCGTGCC AGTGGGGTCC CGGATCGTTT
(201) TAGCGGCTCT GGATCCGGCA CCGATTTTAC CCTGAAAATT AGCCGTGTGG
(251) AAGCTGAAGA CGTGGGCGTG TATTATTGCC AGCAGTATTC TTCTAAGTCT
(301) GCTACCTTTG GCCAGGGTAC GAAAGTTGAA ATTAAACGTA CG
```

3079_Vk kappa 1 (SEQ ID NO: 10):

```
(1)   GATATCCAGA TGACCCAGAG CCCGTCTAGC CTGAGCGCGA GCGTGGGTGA
(51)  TCGTGTGACC ATTACCTGCA GAGCGAGCCA GGATATTTCT GCTTTTCTGA
(101) ATTGGTACCA GCAGAAACCA GGTAAAGCAC CGAAACTATT AATTTATAAG
(151) GTTTCTAATT TGCAAAGCGG GGTCCCGTCC CGTTTTAGCG GCTCTGGATC
(201) CGGCACTGAT TTTACCCTGA CCATTAGCAG CCTGCAACCT GAAGACTTTG
(251) CGACTTATTA TTGCCAGCAG GCTTATTCTG GTTCTATTAC CTTTGGCCAG
(301) GGTACGAAAG TTGAAATTAA ACGTACG
```

3080_Vl lambda 3 (SEQ ID NO: 11):

```
(1)   GATATCGAAC TGACCCAGCC GCCTTCAGTG AGCGTTGCAC CAGGTCAGAC
(51)  CGCGCGTATC TCGTGTAGCG GCGATAATAT TGGTAATAAG TATGTTTCTT
(101) GGTACCAGCA GAAACCCGGG CAGGCGCCAG TTGTTGTGAT TTATGGTGAT
(151) AATAATCGTC CCTCAGGCAT CCCGGAACGC TTTAGCGGAT CCAACAGCGG
(201) CAACACCGCG ACCCTGACCA TTAGCGGCAC TCAGGCGGAA GACGAAGCGG
(251) ATTATTATTG CTCTTCTTAT GATTCTTCTT ATTTTGTGTT TGGCGGCGGC
(301) ACGAAGTTAA CCGTTCTTGG CCAG
```

3100_Vl lambda 3 (SEQ ID NO: 12):

```
(1)   GATATCGAAC TGACCCAGCC GCCTTCAGTG AGCGTTGCAC CAGGTCAGAC
(51)  CGCGCGTATC TCGTGTAGCG GCGATAATAT TGGTCATTAT TATGCTTCTT
(101) GGTACCAGCA GAAACCCGGG CAGGCGCCAG TTCTTGTGAT TTATCGTGAT
(151) AATGATCGTC CCTCAGGCAT CCCGGAACGC TTTAGCGGAT CCAACAGCGG
(201) CAACACCGCG ACCCTGACCA TTAGCGGCAC TCAGGCGGAA GACGAAGCGG
(251) ATTATTATTG CCAGTCTTAT GATTATCTTC ATGATTTTGT GTTTGGCGGC
(301) GGCACGAAGT TAACCGTTCT TGGCCAG
```

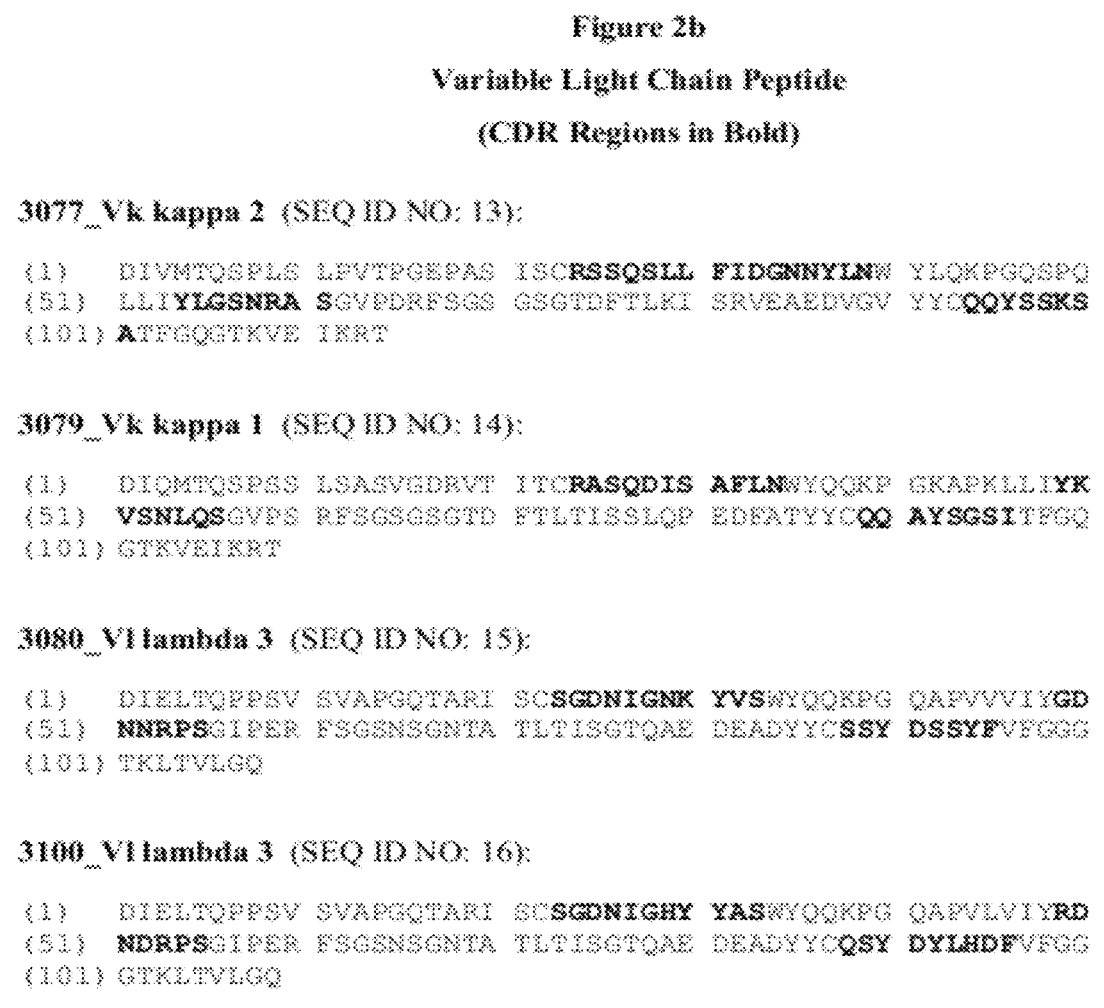

Figure 2b
Variable Light Chain Peptide
(CDR Regions in Bold)

3077_Vk kappa 2 (SEQ ID NO: 13):

(1) DIVMTQSPLS LPVTPGEPAS ISCRSSQSLL FIDGNNYLNW YLQKPGQSPQ
(51) LLIYLGSNRA SGVPDRFSGS GSGTDFTLKI SRVEAEDVGV YYCQQYSSKS
(101) ATFGQGTKVE IKRT

3079_Vk kappa 1 (SEQ ID NO: 14):

(1) DIQMTQSPSS LSASVGDRVT ITCRASQDIS AFLNWYQQKP GKAPKLLIYK
(51) VSNLQSGVPS RFSGSGSGTD FTLTISSLQP EDFATYYCQQ AYSGSITFGQ
(101) GTKVEIKRT

3080_Vl lambda 3 (SEQ ID NO: 15):

(1) DIELTQPPSV SVAPGQTARI SCSGDNIGNK YVSWYQQKPG QAPVVVIYGD
(51) NNRPSGIPER FSGSNSGNTA TLTISGTQAE DEADYYCSSY DSSYFVFGGG
(101) TKLTVLGQ

3100_Vl lambda 3 (SEQ ID NO: 16):

(1) DIELTQPPSV SVAPGQTARI SCSGDNIGHY YASWYQQKPG QAPVLVIYRD
(51) NDRPSGIPER FSGSNSGNTA TLTISGTQAE DEADYYCQSY DYLHDFVFGG
(101) GTKLTVLGQ

Figure 3

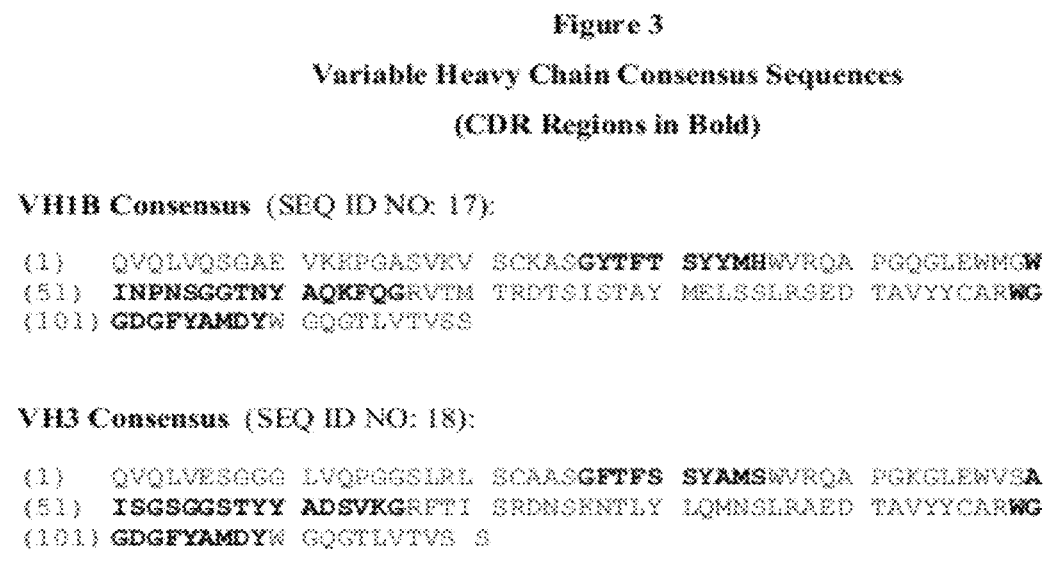

Variable Heavy Chain Consensus Sequences

(CDR Regions in Bold)

VH1B Consensus (SEQ ID NO: 17):

(1) QVQLVQSGAE VKKPGASVKV SCKASGYTFT SYYMHWVRQA PGQGLEWMGW
(51) INPNSGGTNY AQKFQGRVTM TRDTSISTAY MELSSLRSED TAVYYCARWG
(101) GDGFYAMDYW GQGTLVTVSS

VH3 Consensus (SEQ ID NO: 18):

(1) QVQLVESGGG LVQPGGSLRL SCAASGFTFS SYAMSWVRQA PGKGLEWVSA
(51) ISGSGGSTYY ADSVKGRFTI SRDNSKNTLY LQMNSLRAED TAVYYCARWG
(101) GDGFYAMDYW GQGTLVTVS S

Figure 4

Variable Light Chain Consensus Sequences (CDR Regions in Bold)

VL_λ3 Consensus (SEQ ID NO: 19):

(1) SYELTQPPSV SVAPGQTARI SCSGDALGDK YASWYQQKPG QAPVLVIYDD
(51) SDRPSGIPER FSGSNSGNTA TLTISGTQAE DEADYYCQQH YTTPPVFGGG
(101) TKLTVLG

VL_k1 Consensus (SEQ ID NO: 20):

(1) DIQMTQSPSS LSASVGDRVT ITCRASQGIS SYLAWYQQKP GKAPKLLIYA
(51) ASSLQSGVPS RFSGSGSGTD FTLTISSLQP EDFATYYCQQ HYTTPPTFGQ
(101) GTKVEIKR

VL_k2 Consensus (SEQ ID NO: 21):

(1) DIVMTQSPLS LPVTPGEPAS ISCRSSQSLL HSNGYNYLDW YLQKPGQSPQ
(51) LLIYLGSNRA SGVPDRFSGS GSGTDFTLKI SRVEAEDVGV YYCQQHYTTP
(101) PTFGQGTKVE IKR

Figure 5

Peptide Sequence of CD38

(SEQ ID NO: 22):

```
1     mancefspvs gdkpccrlsr raqlclgvsi lvlilvvvla vvvprwrqqw sgpgttkrfp
61    etvlarcvky teihpemrhv dcqsvwdafk gafiskhpcn iteedyqplm klgtqtvpcn
121   killwsrikd lahqftqvqr dmftledtll gyladdltwc gefntskiny qscpdwrkdc
181   snnpvsvfwk tvsrrfaeaa cdvvhvmlng srskifdkns tfgsvevhnl qpekvqtlea
241   wvihggreds rdlcqdptik elesiiskrn iqfsckniyr pdkflqcvkn pedssctsei
```

Figure 6
Nucleotide Sequence of Chimeric OKT10

Heavy Chain (SEQ ID NO: 23):

caggtggaat tggtggaatc tggaggatcc ctgaaactct cctgtgcagc ctcaggattc
gattttagta gatcctggat gaattgggtc cggcaggctc caggaaaagg gctagaatgg
attggagaaa ttaatccaga tagcagtacg ataaactata cgacatctct aaaggataaa
ttcatcatct ccagagacaa cgccaaaaat acgctgtacc tgcaaatgac caaagtgaga
tctgaggaca cagcccttta ttactgtgca agatatggta actggtttcc ttattggggc
caagggactc tggtcactgt cagctcagcc tccaccaagg gtccatcggt cttccccctg
gcaccctcct ccaagagcac ctctgggggc acagcggccc tgggctgcct ggtcaaggac
tacttccccg aaccggtgac ggtgtcgtgg aactcaggcg ccctgaccag cggcgtgcac
accttcccgg ctgtcctaca gtcctcagga ctctactccc tcagcagcgt ggtgaccgtg
ccctccagca gcttgggcac ccagacctac atctgcaacg tgaatcacaa gcccagcaac
accaaggtgg acaagaaagt tgagcccaaa tcttgtgaca aaactcacac atgcccaccg
tgcccagcac ctgaactcct ggggggaccg tcagtcttcc tcttcccccc aaaacccaag
gacaccctca tgatctcccg gacccctgag gtcacatgcg tggtggtgga cgtgagccac
gaagaccctg aggtcaagtt caactggtac gtggacggcg tggaggtgca taatgccaag
acaaagccgc gggaggagca gtacaacagc acgtaccggg tggtcagcgt cctcaccgtc
ctgcaccagg actggctgaa tggcaaggag tacaagtgca aggtctccaa caaagccctc
ccagccccca tcgagaaaac catctccaaa gccaaagggc agccccgaga accacaggtg
tacaccctgc ccccatcccg ggatgagctg accaagaacc aggtcagcct gacctgcctg
gtcaaaggct tctatcccag cgacatcgcc gtggagtggg agagcaatgg gcagccggag
aacaactaca agaccacgcc tcccgtgctg gactccgacg gctccttctt cctctacagc
aagctcaccg tggacaagag caggtggcag caggggaacg tcttctcatg ctccgtgatg
catgaggctc tgcacaacca ctacacgcag aagagcctct ccctgtctcc gggtaaa

Light Chain (SEQ ID NO: 24):

gatatcctga tgacccagtc tcaaaaaatc atgcccacat cagtgggaga cagggtcagc
gtcacctgca aggccagtca aaatgtggat actaatgtag cctggtatca acagaaacca
ggacagtctc ctaaagcact gatttactcg gcatcctacc gatacagtgg agtccctgat

Figure 6 (Continued)

cgcttcacag gcagtggatc tgggacagat ttcactctca ccatcaccaa tgtgcagtct
gaggacttgg cagagtattt ctgtcagcaa tatgacagct atcctctcac gttcggtgct
gggaccaagc tggacctgaa acgtacggtg gctgcaccat ctgtcttcat cttcccgcca
tctgatgagc agttgaaatc tggaactgcc tctgttgtgt gcctgctgaa taacttctat
cccagagagg ccaaagtaca gtggaaggtg gataacgccc tccaatcggg taactcccag
gagagtgtca cagagcagga cagcaaggac agcacctaca gcctcagcag caccctgacg
ctgagcaaag cagactacga gaaacacaaa gtctacgcct gcgaagtcac ccatcagggc
ctgagctcgc ccgtcacaaa gagcttcaac aggggagagt gt Fig.7: Schematic Overview of Epitopes
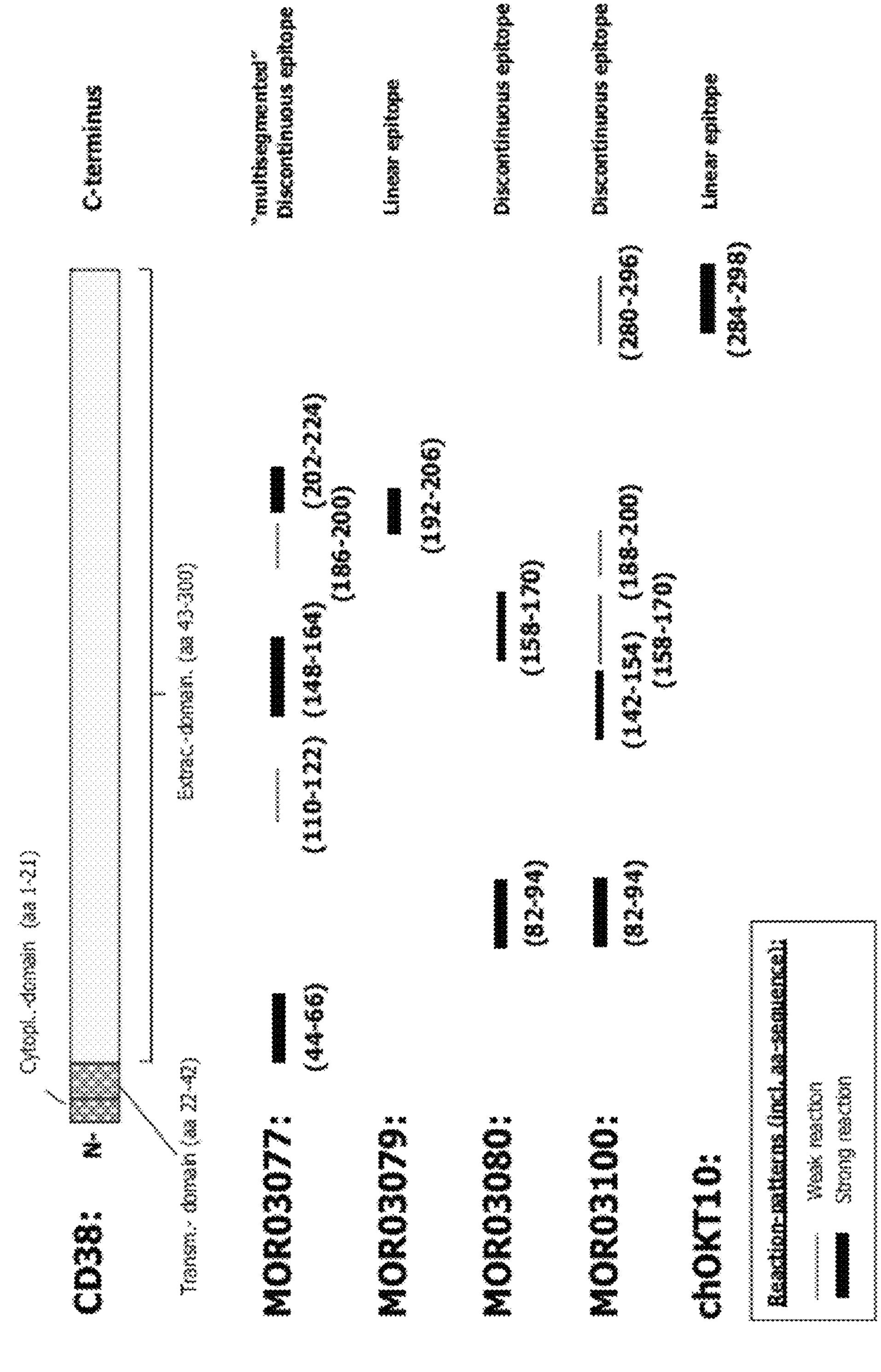

Figure 8: DNA sequence of pMOPRH®_h_IgG1_1

```
                  StyI
                 ~~~~~~~
 601    TCGCTATTAC CATGGTGATG CGGTTTTGGC AGTACATCAA TGGGCGTGGA
        AGCGATAATG GTACCACTAC GCCAAAACCG TCATGTAGTT ACCCGCACCT

                                                     AatII
                                                    ~~~~~~
 651    TAGCGGTTTG ACTCACGGGG ATTTCCAAGT CTCCACCCCA TTGACGTCAA
        ATCGCCAAAC TGAGTGCCCC TAAAGGTTCA GAGGTGGGGT AACTGCAGTT

 701    TGGGAGTTTG TTTTGGCACC AAAATCAACG GGACTTTCCA AAATGTCGTA
        ACCCTCAAAC AAAACCGTGG TTTTAGTTGC CCTGAAAGGT TTTACAGCAT

 751    ACAACTCCGC CCCATTGACG CAAATGGGCG GTAGGCGTGT ACGGTGGGAG
        TGTTGAGGCG GGGTAACTGC GTTTACCCGC CATCCGCACA TGCCACCCTC

 801    GTCTATATAA GCAGAGCTCT CTGGCTAACT AGAGAACCCA CTGCTTACTG
        CAGATATATT CGTCTCGAGA GACCGATTGA TCTCTTGGGT GACGAATGAC

                   pMORPH®_Ig_FOR 100.0%                NheI
                   ~~~~~~~~~~~~~~~~~~~~~~              ~~~~~~
 851    GCTTATCGAA ATTAATACGA CTCACTATAG GGAGACCCAA GCTGGCTAGC
        CGAATAGCTT TAATTATGCT GAGTGATATC CCTCTGGGTT CGACCGATCG

                   M   K   H  L  W   F  F  L   L  L  V  A   A  P  R ·
 901    GCCACCATGA AACACCTGTG GTTCTTCCTC CTGCTGGTGG CAGCTCCCAG
        CGGTGGTACT TTGTGGACAC CAAGAAGGAG GACGACCACC GTCGAGGGTC

                             EcoRI                 BlpI        StyI
                             ~~~~~~~               ~~~~~~~~     ~
                                                              A  S  T ·
        · W  V  L   S  Q  V  E   F  C  R   R  L  A   Q
 951    ATGGGTCCTG TCCCAGGTGG AATTCTGCAG GCGGTTAGCT CAGCCTCCAC
        TACCCAGGAC AGGGTCCACC TTAAGACGTC CGCCAATCGA GTCGGAGGTG

        StyI           BbsI
        ~~~~~         ~~~~~~
        · K  G  P   S  V  F  P   L  A  P   S  S  K   S  T  S  G ·
1001    CAAGGGTCCA TCGGTCTTCC CCCTGGCACC CTCCTCCAAG AGCACCTCTG
        GTTCCCAGGT AGCCAGAAGG GGGACCGTGG GAGGAGGTTC TCGTGGAGAC

        ·  G  T  A   A  L  G   C  L  V  K   D  Y  F   P  E  P
1051    GGGGCACAGC GGCCCTGGGC TGCCTGGTCA AGGACTACTT CCCCGAACCG
        CCCCGTGTCG CCGGGACCCG ACGGACCAGT TCCTGATGAA GGGGCTTGGC
```

Figure 8 (Continued)

```
             V  T  V  S   W  N  S   G  A  L   T  S  G  V   H  T  F ·
1101      GTGACGGTGT CGTGGAACTC AGGCGCCCTG ACCAGCGGCG TGCACACCTT
          CACTGCCACA GCACCTTGAG TCCGCGGGAC TGGTCGCCGC ACGTGTGGAA

          · P  A  V   L  Q  S  S   G  L  Y   S  L  S   S  V  V  T ·
1151      CCCGGCTGTC CTACAGTCCT CAGGACTCTA CTCCCTCAGC AGCGTGGTGA
          GGGCCGACAG GATGTCAGGA GTCCTGAGAT GAGGGAGTCG TCGCACCACT

          ·  V  P  S   S  S  L   G  T  Q  T   Y  I  C   N  V  N
1201      CCGTGCCCTC CAGCAGCTTG GGCACCCAGA CCTACATCTG CAACGTGAAT
          GGCACGGGAG GTCGTCGAAC CCGTGGGTCT GGATGTAGAC GTTGCACTTA

                              StyI
                             ~~~~~~
           H  K  P  S   N  T  K   V  D  K   K  V  E  P   K  S  C ·
1251      CACAAGCCCA GCAACACCAA GGTGGACAAG AAAGTTGAGC CCAAATCTTG
          GTGTTCGGGT CGTTGTGGTT CCACCTGTTC TTTCAACTCG GGTTTAGAAC

          · D  K  T   H  T  C  P   P  C  P   A  P  E   L  L  G  G ·
1301      TGACAAAACT CACACATGCC CACCGTGCCC AGCACCTGAA CTCCTGGGGG
          ACTGTTTTGA GTGTGTACGG GTGGCACGGG TCGTGGACTT GAGGACCCCC

                   BbsI                        StyI
                  ~~~~~~                      ~~~~~
          ·  P  S  V   F  L  F   P  P  K  P   K  D  T   L  M  I
1351      GACCGTCAGT CTTCCTCTTC CCCCCAAAAC CCAAGGACAC CCTCATGATC
          CTGGCAGTCA GAAGGAGAAG GGGGGTTTTG GGTTCCTGTG GGAGTACTAG

                                                         BbsI
                                                        ~~~~~
           S  R  T  P   E  V  T   C  V  V   V  D  V  S   H  E  D ·
1401      TCCCGGACCC CTGAGGTCAC ATGCGTGGTG GTGGACGTGA GCCACGAAGA
          AGGGCCTGGG GACTCCAGTG TACGCACCAC CACCTGCACT CGGTGCTTCT

          BbsI
          ~
          · P  E  V   K  F  N  W   Y  V  D   G  V  E   V  H  N  A ·
1451      CCCTGAGGTC AAGTTCAACT GGTACGTGGA CGGCGTGGAG GTGCATAATG
          GGGACTCCAG TTCAAGTTGA CCATGCACCT GCCGCACCTC CACGTATTAC

          ·  K  T  K   P  R  E   E  Q  Y  N   S  T  Y   R  V  V
1501      CCAAGACAAA GCCGCGGGAG GAGCAGTACA ACAGCACGTA CCGGGTGGTC
          GGTTCTGTTT CGGCGCCCTC CTCGTCATGT TGTCGTGCAT GGCCCACCAG

           S  V  L  T   V  L  H   Q  D  W   L  N  G  K   E  Y  K ·
1551      AGCGTCCTCA CCGTCCTGCA CCAGGACTGG CTGAATGGCA AGGAGTACAA
          TCGCAGGAGT GGCAGGACGT GGTCCTGACC GACTTACCGT TCCTCATGTT

          · C  K  V   S  N  K  A   L  P  A   P  I  E   K  T  I  S ·
1601      GTGCAAGGTC TCCAACAAAG CCCTCCCAGC CCCCATCGAG AAAACCATCT
          CACGTTCCAG AGGTTGTTTC GGGAGGGTCG GGGGTAGCTC TTTTGGTAGA

                                                 BsrGI
                                                ~~~~~~
          ·  K  A  K   G  Q  P   R  E  P  Q   V  Y  T   L  P  P
1651      CCAAAGCCAA AGGGCAGCCC CGAGAACCAC AGGTGTACAC CCTGCCCCCA
          GGTTTCGGTT TCCCGTCGGG GCTCTTGGTG TCCACATGTG GGACGGGGGT
```

Figure 8 (Continued)

```
          S  R  D  E   L  T  K   N  Q  V   S  L  T  C   L  V  K ·
1701      TCCCGGGATG AGCTGACCAA GAACCAGGTC AGCCTGACCT GCCTGGTCAA
          AGGGCCCTAC TCGACTGGTT CTTGGTCCAG TCGGACTGGA CGGACCAGTT

          · G  F  Y   P  S  D  I   A  V  E   W  E  S   N  G  Q  P ·
1751      AGGCTTCTAT CCCAGCGACA TCGCCGTGGA GTGGGAGAGC AATGGGCAGC
          TCCGAAGATA GGGTCGCTGT AGCGGCACCT CACCCTCTCG TTACCCGTCG

          ·  E  N  N   Y  K  T   T  P  P  V   L  D  S   D  G  S
1801      CGGAGAACAA CTACAAGACC ACGCCTCCCG TGCTGGACTC CGACGGCTCC
          GCCTCTTGTT GATGTTCTGG TGCGGAGGGC ACGACCTGAG GCTGCCGAGG

           F  F  L  Y   S  K  L   T  V  D   K  S  R  W   Q  Q  G ·
1851      TTCTTCCTCT ACAGCAAGCT CACCGTGGAC AAGAGCAGGT GGCAGCAGGG
          AAGAAGGAGA TGTCGTTCGA GTGGCACCTG TTCTCGTCCA CCGTCGTCCC

               BbsI                 NsiI
              ~~~~~~~              ~~~~~~
          · N  V  F   S  C  S  V   M  H  E   A  L  H   N  H  Y  T ·
1901      GAACGTCTTC TCATGCTCCG TGATGCATGA GGCTCTGCAC AACCACTACA
          CTTGCAGAAG AGTACGAGGC ACTACGTACT CCGAGACGTG TTGGTGATGT

               SapI                                        PmeI
              ~~~~~~~~~                                 ~~~~~~~~~
          ·  Q  K  S   L  S  L   S  P  G  K   *
1951      CGCAGAAGAG CCTCTCCCTG TCTCCGGGTA AATGAGGGCC CGTTTAAACC
          GCGTCTTCTC GGAGAGGGAC AGAGGCCCAT TTACTCCCGG GCAAATTTGG

2001      CGCTGATCAG CCTCGACTGT GCCTTCTAGT TGCCAGCCAT CTGTTGTTTG
          GCGACTAGTC GGAGCTGACA CGGAAGATCA ACGGTCGGTA GACAACAAAC

                     ~~~~~~~~~~~~~~~~~~~~
                     pNORPH® Ig_REV 100.0%
2051      CCCCTCCCCC GTGCCTTCCT TGACCCTGGA AGGTGCCACT CCCACTGTCC
          GGGGAGGGGG CACGGAAGGA ACTGGGACCT TCCACGGTGA GGGTGACAGG
```

Figure 9: DNA Sequence of Ig kappa light chain expression vector pMORPH®_h_Igκ_1

```
                       StyI
                     ~~~~~~~
 601  TCGCTATTAC CATGGTGATG CGGTTTTGGC AGTACATCAA TGGGCGTGGA
      AGCGATAATG GTACCACTAC GCCAAAACCG TCATGTAGTT ACCCGCACCT

 651  TAGCGGTTTG ACTCACGGGG ATTTCCAAGT CTCCACCCCA TTGACGTCAA
      ATCGCCAAAC TGAGTGCCCC TAAAGGTTCA GAGGTGGGGT AACTGCAGTT

 701  TGGGAGTTTG TTTTGGCACC AAAATCAACG GGACTTTCCA AAATGTCGTA
      ACCCTCAAAC AAAACCGTGG TTTTAGTTGC CCTGAAAGGT TTTACAGCAT

 751  ACAACTCCGC CCCATTGACG CAAATGGGCG GTAGGCGTGT ACGGTGGGAG
      TGTTGAGGCG GGGTAACTGC GTTTACCCGC CATCCGCACA TGCCACCCTC

 801  GTCTATATAA GCAGAGCTCT CTGGCTAACT AGAGAACCCA CTGCTTACTG
      CAGATATATT CGTCTCGAGA GACCGATTGA TCTCTTGGGT GACGAATGAC

                    pMORPH®_Ig_FOR 100%                NheI
                 ~~~~~~~~~~~~~~~~~~~~~~~~~~~~          ~~~~~~
 851  GCTTATCGAA ATTAATACGA CTCACTATAG GGAGACCCAA GCTGGCTAGC
      CGAATAGCTT TAATTATGCT GAGTGATATC CCTCTGGGTT CGACCGATCG

  +1          M  V   L  Q  T   Q  V  F   I  S  L  L   L  W  I
          StyI
         ~~~~~~
 901  GCCACCATGG TGTTGCAGAC CCAGGTCTTC ATTTCTCTGT TGCTCTGGAT
      CGGTGGTACC ACAACGTCTG GGTCCAGAAG TAAAGAGACA ACGAGACCTA
                                  BbsI
                                ~~~~~~~

  +1   S  G  A   Y  G  D  I   V  M  I   K  R  T   V  A  A
                     EcoRV                 BsiWI
                   ~~~~~~~~              ~~~~~~~
 951  CTCTGGTGCC TACGGGGATA TCGTGATGAT TAAACGTACG GTGGCTGCAC
      GAGACCACGG ATGCCCCTAT AGCACTACTA ATTTGCATGC CACCGACGTG

  +1 P  S  V  F   I  F  P   P  S  D  E   Q  L  K   S  G  T
1001  CATCTGTCTT CATCTTCCCG CCATCTGATG AGCAGTTGAA ATCTGGAACT
      GTAGACAGAA GTAGAAGGGC GGTAGACTAC TCGTCAACTT TAGACCTTGA
           BbsI
         ~~~~~~~~
```

Figure 9 (Continued)

```
  +1  A  S  V  V   C  L  L   N  N  F   Y  P  R  E   A  K  V
1051  GCCTCTGTTG TGTGCCTGCT GAATAACTTC TATCCCAGAG AGGCCAAAGT
      CGGAGACAAC ACACGGACGA CTTATTGAAG ATAGGGTCTC TCCGGTTTCA

  +1   Q  W  K   V  D  N  A   L  Q  S   G  N  S   Q  E  S
1101  ACAGTGGAAG GTGGATAACG CCCTCCAATC GGGTAACTCC CAGGAGAGTG
      TGTCACCTTC CACCTATTGC GGGAGGTTAG CCCATTGAGG GTCCTCTCAC

  +1 V  T  E  Q   D  S  K   D  S  T  Y   S  L  S   S  T  L
1151  TCACAGAGCA GGACAGCAAG GACAGCACCT ACAGCCTCAG CAGCACCCTG
      AGTGTCTCGT CCTGTCGTTC CTGTCGTGGA TGTCGGAGTC GTCGTGGGAC

  +1  T  L  S  K   A  D  Y   E  K  H   K  V  Y  A   C  E  V
         BlpI
        ~~~~~~~
1201  ACGCTGAGCA AAGCAGACTA CGAGAAACAC AAAGTCTACG CCTGCGAAGT
      TGCGACTCGT TTCGTCTGAT GCTCTTTGTG TTTCAGATGC GGACGCTTCA

  +1   T  H  Q   G  L  S  S   P  V  T   K  S  F   N  R  G
1251  CACCCATCAG GGCCTGAGCT CGCCCGTCAC AAAGAGCTTC AACAGGGGAG
      GTGGGTAGTC CCGGACTCGA GCGGGCAGTG TTTCTCGAAG TTGTCCCCTC

  +1 E  C  *
                      PmeI                  pMORPH®_Ig_REV 100%
                    ~~~~~~~~~~              ==========================
1301  AGTGTTAGGG GCCCGTTTAA ACCCGCTGAT CAGCCTCGAC TGTGCCTTCT
      TCACAATCCC CGGGCAAATT TGGGCGACTA GTCGGAGCTG ACACGGAAGA


      =
1351  AGTTGCCAGC CATCTGTTGT TTGCCCCTCC CCCGTGCCTT CCTTGACCCT
      TCAACGGTCG GTAGACAACA AACGGGGAGG GGGCACGGAA GGAACTGGGA
```

Figure 10: DNA Sequence of HuCAL® Ig lambda light chain vector pMORPH®_h_Igλ_1

```
                    StyI
                  ~~~~~~~
 601   TCGCTATTAC CATGGTGATG CGGTTTTGGC AGTACATCAA TGGGCGTGGA
       AGCGATAATG GTACCACTAC GCCAAAACCG TCATGTAGTT ACCCGCACCT

 651   TAGCGGTTTG ACTCACGGGG ATTTCCAAGT CTCCACCCCA TTGACGTCAA
       ATCGCCAAAC TGAGTGCCCC TAAAGGTTCA GAGGTGGGGT AACTGCAGTT

 701   TGGGAGTTTG TTTTGGCACC AAAATCAACG GGACTTTCCA AAATGTCGTA
       ACCCTCAAAC AAAACCGTGG TTTTAGTTGC CCTGAAAGGT TTTACAGCAT

 751   ACAACTCCGC CCCATTGACG CAAATGGGCG GTAGGCGTGT ACGGTGGGAG
       TGTTGAGGCG GGGTAACTGC GTTTACCCGC CATCCGCACA TGCCACCCTC

 801   GTCTATATAA GCAGAGCTCT CTGGCTAACT AGAGAACCCA CTGCTTACTG
       CAGATATATT CGTCTCGAGA GACCGATTGA TCTCTTGGGT GACGAATGAC

                     pM_Ig_FOR  100.0%                 NheI
                  ~~~~~~~~~~~~~~~~~~~~~~~~~~          ~~~~~~
 851   GCTTATCGAA ATTAATACGA CTCACTATAG GGAGACCCAA GCTGGCTAGC
       CGAATAGCTT TAATTATGCT GAGTGATATC CCTCTGGGTT CGACCGATCG

  +1         M  A   W  A  L   L  L  L   T  L  L  T   Q  G  T
          StyI
        ~~~~~~
 901   GCCACCATGG CCTGGGCTCT GCTGCTCCTC ACCCTCCTCA CTCAGGGCAC
       CGGTGGTACC GGACCCGAGA CGACGAGGAG TGGGAGGAGT GAGTCCCGTG

  +2                                             T  V   L  G  Q
  +1    G  S  W   A  D  I  V   M  H  E   V
       BamHI         EcoRV                 HpaI       StyI
       ~~~~~~       ~~~~~~               ~~~~~~     ~~~~~~
 951   AGGATCCTGG GCTGATATCG TGATGCACGA AGTTAACCGT CCTAGGTCAG
       TCCTAGGACC CGACTATAGC ACTACGTGCT TCAATTGGCA GGATCCAGTC

  +2   P  K  A  A   P  S  V   T  L  F   P  P  S  S   E  E  L
       StyI
      ~~~~~~
1001   CCCAAGGCTG CCCCCTCGGT CACTCTGTTC CCGCCCTCCT CTGAGGAGCT
       GGGTTCCGAC GGGGGAGCCA GTGAGACAAG GGCGGGAGGA GACTCCTCGA

  +2    Q  A  N   K  A  T  L   V  C  L   I  S  D   F  Y  P
1051   TCAAGCCAAC AAGGCCACAC TGGTGTGTCT CATAAGTGAC TTCTACCCGG
       AGTTCGGTTG TTCCGGTGTG ACCACACAGA GTATTCACTG AAGATGGGCC
```

Figure 10 (Continued)

```
    +2 G   A   V   T    V   A   W    K   G   D   S    S   P   V    K   A   G
1101   GAGCCGTGAC AGTGGCCTGG AAGGGAGATA GCAGCCCCGT CAAGGCGGGA
       CTCGGCACTG TCACCGGACC TTCCCTCTAT CGTCGGGGCA GTTCCGCCCT

    +2  V   E   T   T    T   P   S    K   Q   S    N   N   K   Y    A   A   S
1151   GTGGAGACCA CCACACCCTC CAAACAAAGC AACAACAAGT ACGCGGCCAG
       CACCTCTGGT GGTGTGGGAG GTTTGTTTCG TTGTTGTTCA TGCGCCGGTC

    +2   S   Y   L    S   L   T   P    E   Q   W    K   S   H    R   S   Y
1201   CAGCTATCTG AGCCTGACGC CTGAGCAGTG GAAGTCCCAC AGAAGCTACA
       GTCGATAGAC TCGGACTGCG GACTCGTCAC CTTCAGGGTG TCTTCGATGT

    +2 S   C   Q   V    T   H   E    G   S   T   V    E   K   T    V   A   P
                                                     SbsI
                                                    ~~~~~~
1251   GCTGCCAGGT CACGCATGAA GGGAGCACCG TGGAGAAGAC AGTGGCCCCT
       CGACGGTCCA GTGCGTACTT CCCTCGTGGC ACCTCTTCTG TCACCGGGGA

    +2  T   E   C   S    *
                                     PmeI
                                   ~~~~~~~~~
1301   ACAGAATGTT CATAGGGGCC CGTTTAAACC CGCTGATCAG CCTCGACTGT
       TGTCTTACAA GTATCCCCGG GCAAATTTGG GCGACTAGTC GGAGCTGACA
                                                  pM_Ig_REV 100%
                                                   ~~~~~~~~~~~

1351   GCCTTCTAGT TGCCAGCCAT CTGTTGTTTG CCCCTCCCCC GTGCCTTCCT
       CGGAAGATCA ACGGTCGGTA GACAACAAAC GGGGAGGGGG CACGGAAGGA
       pM_Ig_REV  100.0%
       ~~~~~~~~~
```

Fig. 11: Agonistic activities
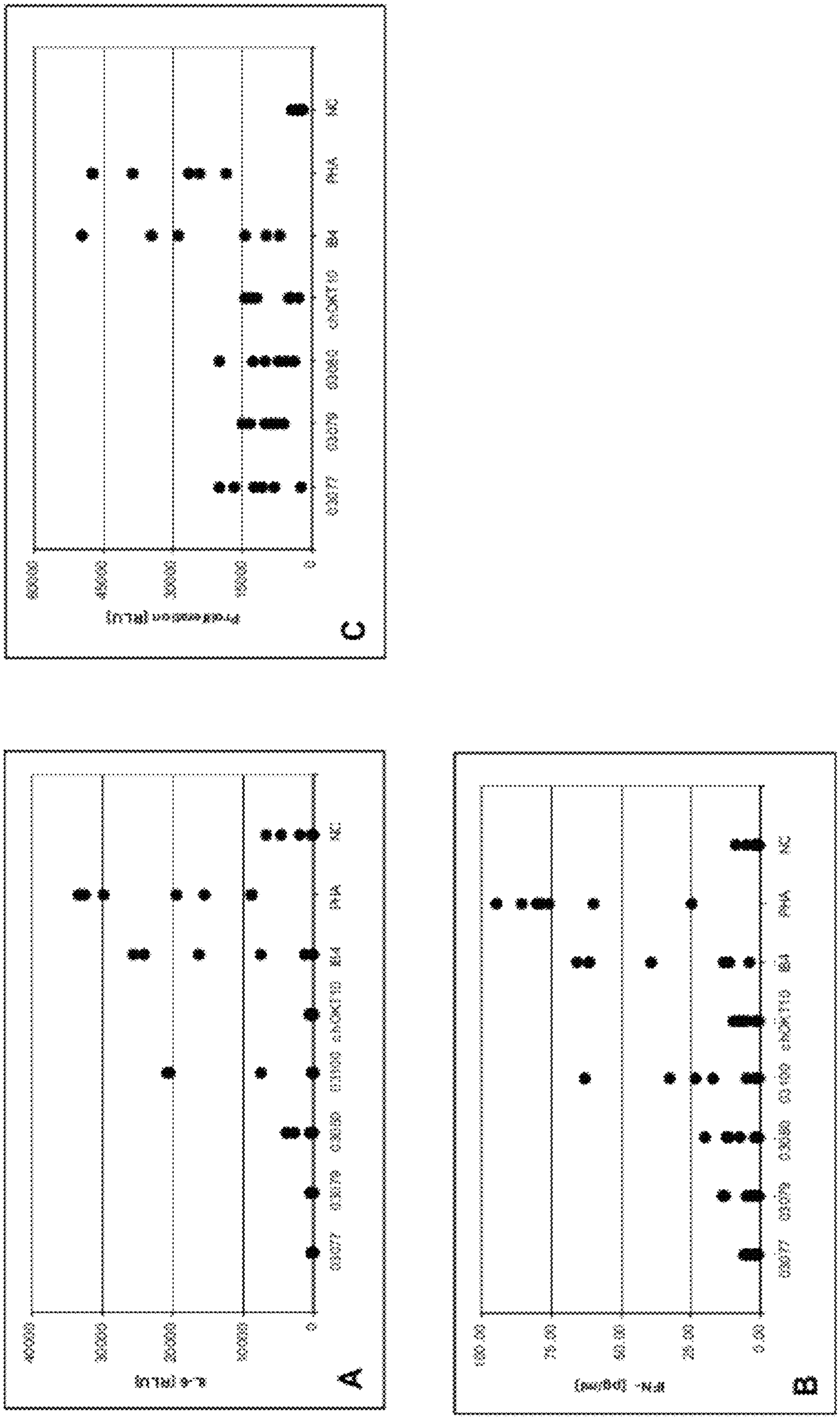

Figure 12: Specificity ELISA
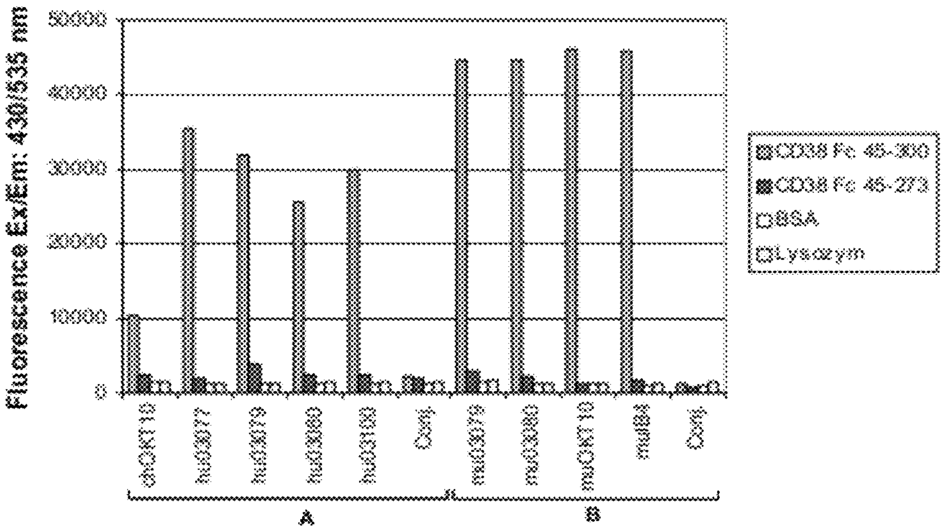

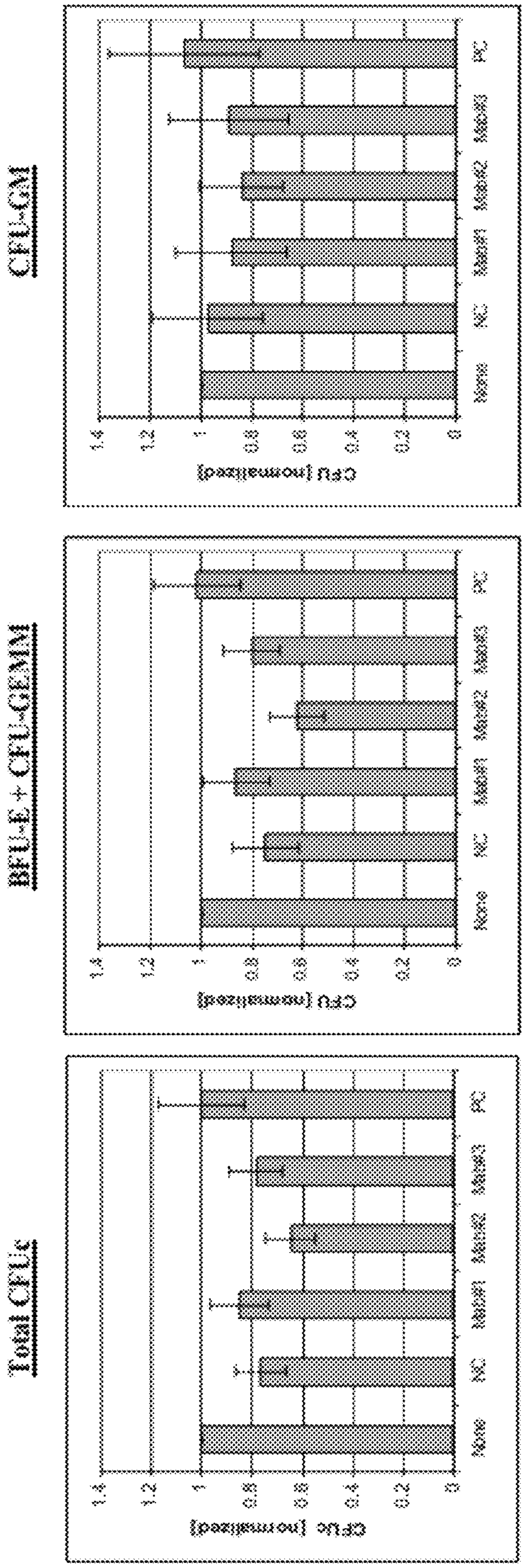
Fig. 13: Cytotoxicity towards CD34+/CD38+ progenitor cells

Fig. 14: ADCC with different cell-lines

| Cell line | Culture Collection | Origin | Expression [MFI] | Max. specific killing [%] in ADCC[a,c] | | | |
|---|---|---|---|---|---|---|---|
| | | | | Mab#1 | Mab#2 | Mab#3 | PC |
| RPMI 8226 | ATCC CCL-155 | MM | 405.71 | 56 | 58 | 54 | 46 |
| KMS-12-BM | DSMZ ACC551 | MM | 142.29 | 26 | 32 | 30 | 34 |
| NCI-H929 | ECACC95050415 | MM | 45.01 | 68 | 73 | 38 | 54 |
| OPM-2 | DSMZ ACC50 | MM | 37.99 | 6 | 13 | 3 | 7 |
| U-266 | ECACC85051003 | MM | 26.14 | 17 | 14 | 12 | 16 |
| KMS-11 | Namba *et al.*, 1989[b] | MM | 26.81[c] | 22 | 30 | 26 | 28 |
| JVM-13 | DSMZACC19 | CLL | 463.93 | 11 | 20 | 12 | 15 |
| JVM-2 | DSMZACC12 | CLL | 140.84 | 22 | 28 | 10 | 24 |
| CCRF-CEM | ECACC85112105 | ALL | 301.46 | 24 | 29 | 20 | 22 |
| Jurkat | DSMZ ACC282 | ALL | 202.99 | 7 | 8 | 13 | 12 |
| AML-193 | DSMZ ACC549 | AML | 62.69[d] | 33 | 26 | 39 | 33 |
| OCI-AML5 | DSMZ ACC247 | AML | 207.55[d] | 20 | 21 | 16 | 26 |
| NB-4 | DSMZ ACC207 | AML | 164.7[d] | 36 | 38 | 32 | 37 |
| THP-1 | DSMZ ACC16 | AML | 34.41 | 64 | 59 | 38 | 43 |
| HL-60[e] | DSMZ ACC3 | AML | 18.43[c] | 29 | 35 | 29 | 29 |
| Raji | Burkitt's Lymph. | Burkitt's lymph. | n.d. | 53 | 62 | 48 | n.d. |

Fig. 15: ADCC with MM-samples

| Parameters: / Antibodies | Mab#1 | Mab#2 | Mab#3 | PC |
|---|---|---|---|---|
| MM samples: EC50 [nM]#: | 0.116-0.202 | 0.006-0.185 | 0.027-0.249 | 0.282-0.356 |
| MM samples: Max spec. killing [%] | 13.1 - 61.6 | 16.2 - 57.9 | 13.6 - 36.0 | 15.5 - 49.5 |

Fig. 16: Treatment of human myeloma xenograft with MOR03080
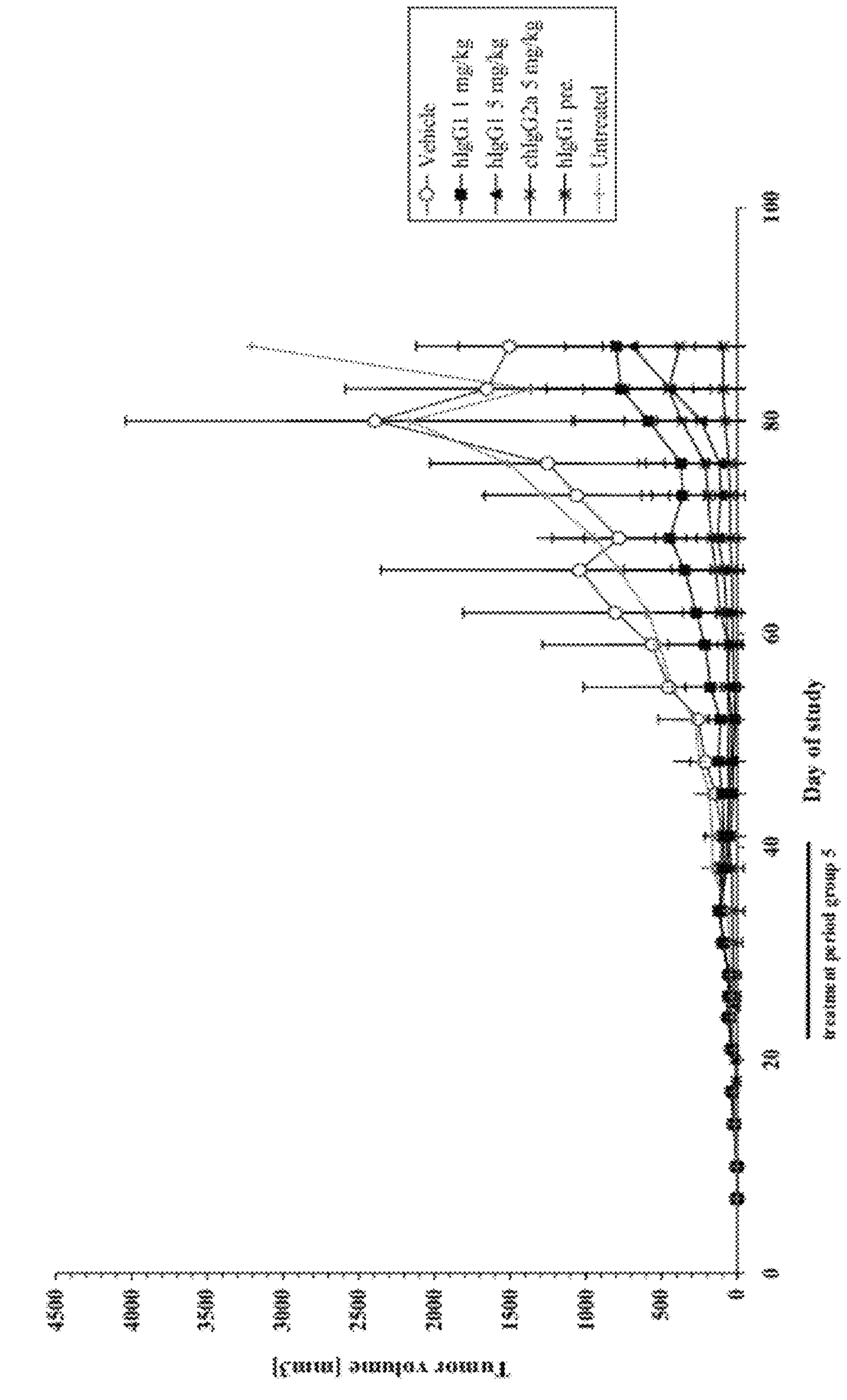

Fig. 17: Cross-reactivity FACS analysis
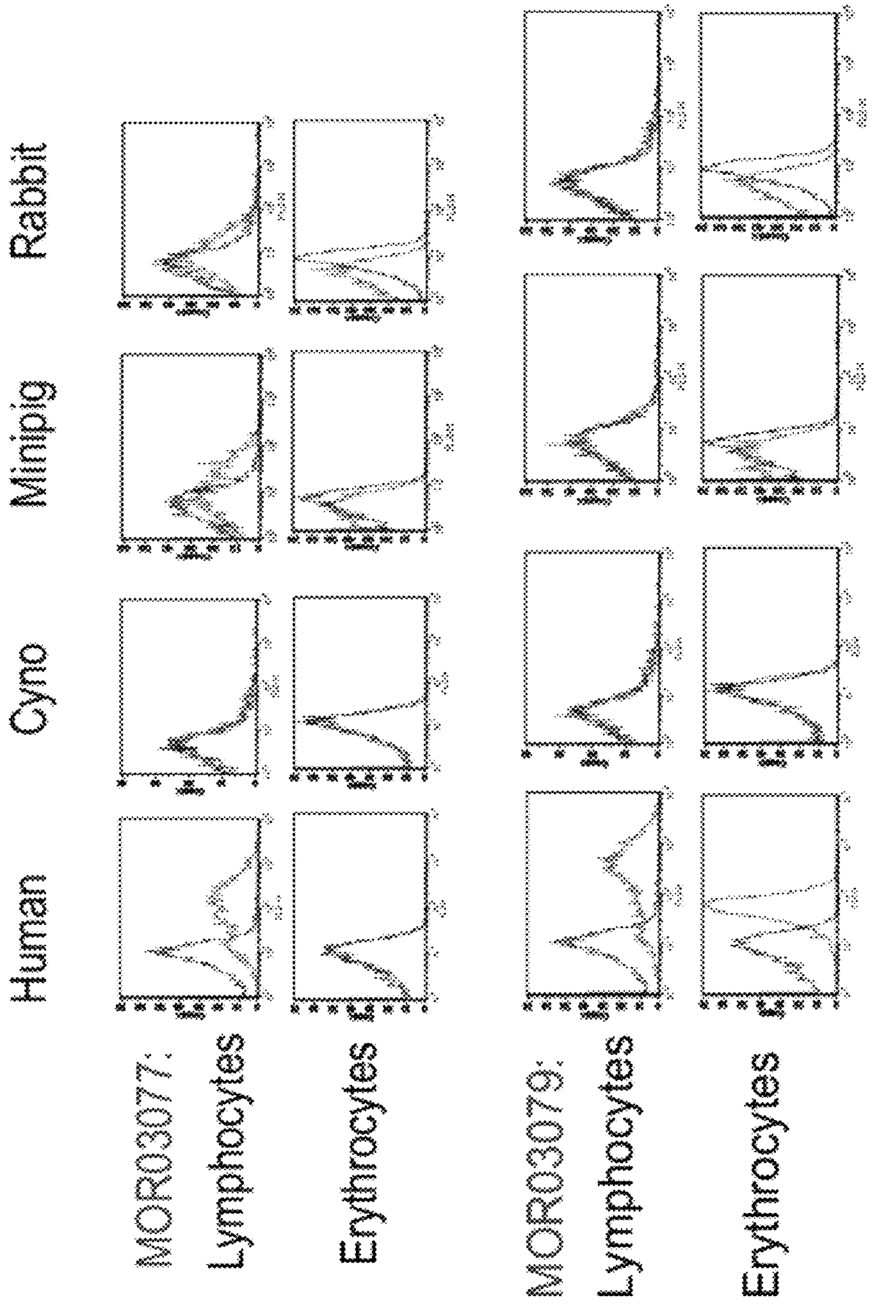

Figure 18: CD38 cross-linking with Raji cells
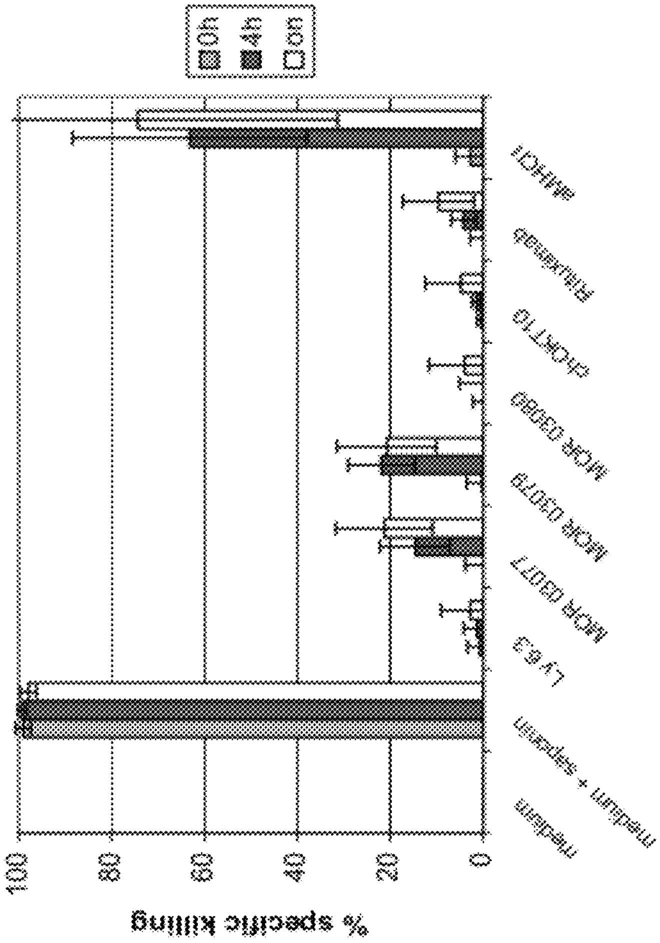

Figure 19: CDC assay with hCD38 CHO-transfectants
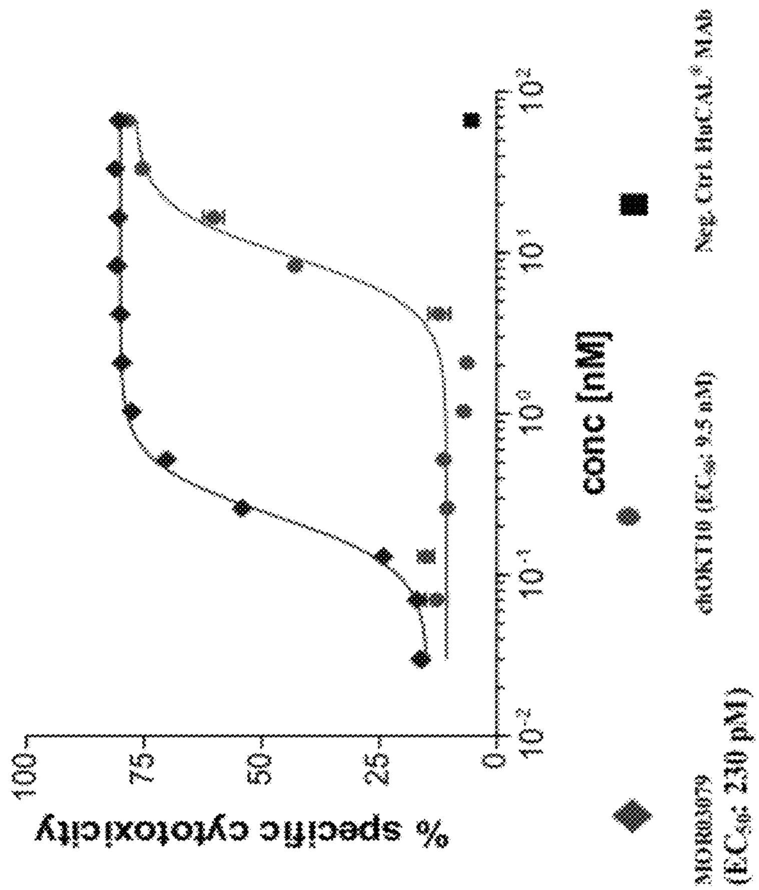

Figure 20: ADCC assay with primary multiple myeloma samples
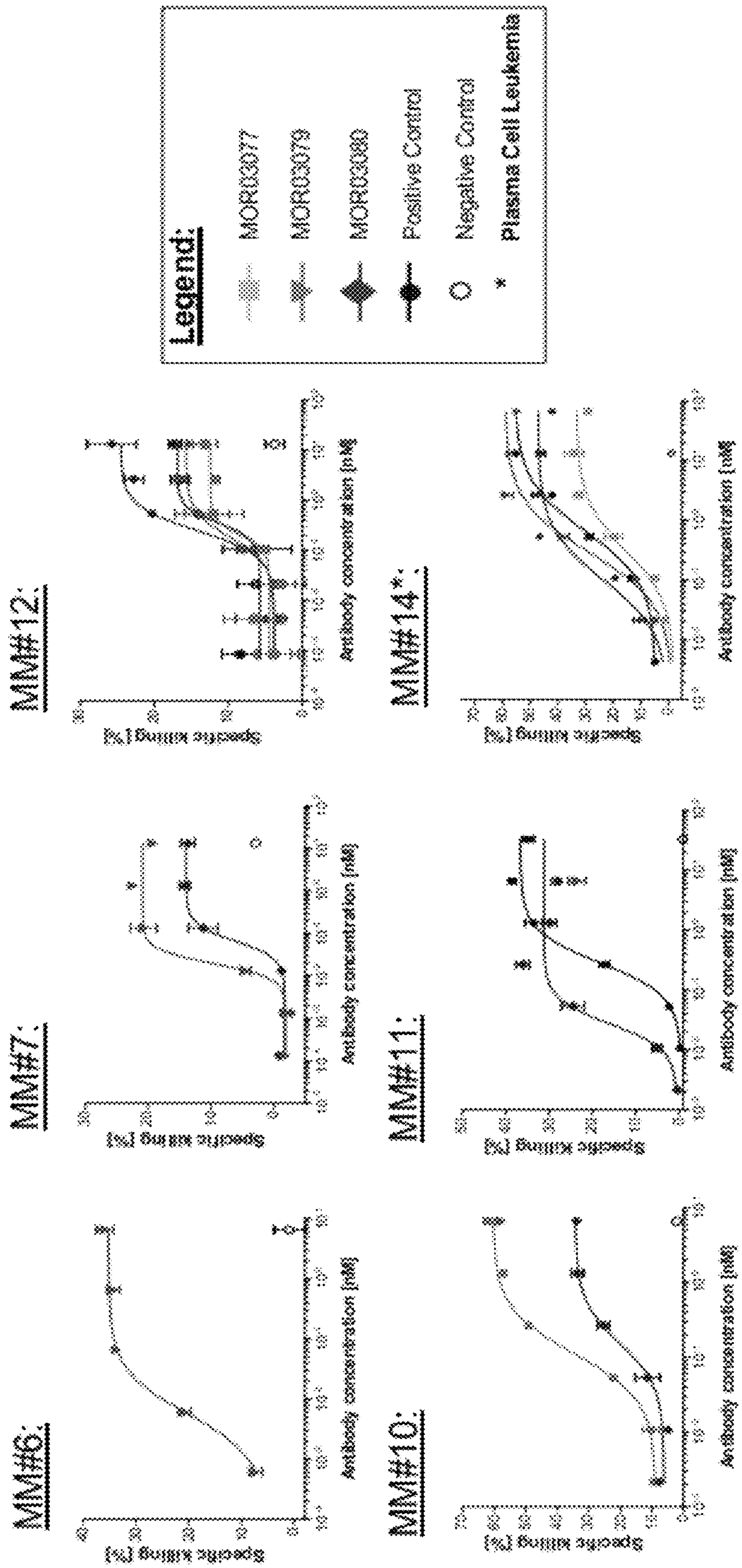

SEQUENCE LISTING

```
<160> NUMBER OF SEQ ID NOS: 67

<210> SEQ ID NO 1
<211> LENGTH: 363
<212> TYPE: DNA
<213> ORGANISM: Homo sapiens

<400> SEQUENCE: 1

caggtgcaat tggttcagag cggcgcggaa gtgaaaaaac cgggcgcgag cgtgaaagtg     60

agctgcaaag cctccggata tacctttact tcttattcta ttaattgggt ccgccaagcc    120

cctgggcagg gtctcgagtg gatgggctat atcgatccga atcgtggcaa tacgaattac    180

gcgcagaagt ttcagggccg ggtgaccatg acccgtgata ccagcattag caccgcgtat    240

atggaactga gcagcctgcg tagcgaagat acggccgtgt attattgcgc gcgtgagtat    300

atttatttta ttcatggtat gcttgatttt tggggccaag gcaccctggt gacggttagc    360

tca                                                                  363


<210> SEQ ID NO 2
<211> LENGTH: 366
<212> TYPE: DNA
<213> ORGANISM: Homo sapiens

<400> SEQUENCE: 2

caggtgcaat tggtggaaag cggcggcggc ctggtgcaac cgggcggcag cctgcgtctg     60

agctgcgcgg cctccggatt taccttttct aattatggta tgcattgggt gcgccaagcc    120

cctgggaagg gtctcgagtg ggtgagcaat atccgttctg atggtagctg gacctattat    180

gcggatagcg tgaaaggccg ttttaccatt tcacgtgata attcgaaaaa caccctgtat    240

ctgcaaatga acagcctgcg tgcggaagat acggccgtgt attattgcgc gcgtcgttat    300

tggtctaagt ctcatgcttc tgttactgat tattggggcc aaggcaccct ggtgacggtt    360

agctca                                                               366


<210> SEQ ID NO 3
<211> LENGTH: 366
<212> TYPE: DNA
<213> ORGANISM: Homo sapiens

<400> SEQUENCE: 3

caggtgcaat tggtggaaag cggcggcggc ctggtgcaac cgggcggcag cctgcgtctg     60

agctgcgcgg cctccggatt taccttttct tcttatggta tgcattgggt gcgccaagcc    120

cctgggaagg gtctcgagtg ggtgagcaat atctattctg atggtagcaa taccttttat    180

gcggatagcg tgaaaggccg ttttaccatt tcacgtgata attcgaaaaa caccctgtat    240

ctgcaaatga acagcctgcg tgcggaagat acggccgtgt attattgcgc gcgtaatatg    300

tatcgttggc cttttcatta ttttttgat tattggggcc aaggcaccct ggtgacggtt    360
```

-continued

```
agctca                                                              366


<210> SEQ ID NO 4
<211> LENGTH: 357
<212> TYPE: DNA
<213> ORGANISM: Homo sapiens

<400> SEQUENCE: 4

caggtgcaat tggtggaaag cggcggcggc ctggtgcaac cgggcggcag cctgcgtctg     60

agctgcgcgg cctccggatt taccttttct tctaatggta tgtcttgggt gcgccaagcc    120

cctgggaagg gtctcgagtg ggtgagcaat atctcttatc tttctagctc tacctattat    180

gcggatagcg tgaaaggccg ttttaccatt tcacgtgata attcgaaaaa caccctgtat    240

ctgcaaatga acagcctgcg tgcggaagat acggccgtgt attattgcgc gcgtttttat    300

ggttatttta attatgctga tgtttggggc caaggcaccc tggtgacggt tagctca       357


<210> SEQ ID NO 5
<211> LENGTH: 121
<212> TYPE: PRT
<213> ORGANISM: Homo sapiens

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Ile Asn Trp Val Arg Gln Ala Pro Gly Gln Gly Leu Glu Trp Met
        35                  40                  45

Gly Tyr Ile Asp Pro Asn Arg Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Ile Tyr Phe Ile His Gly Met Leu Asp Phe Trp Gly
            100                 105                 110

Gln Gly Thr Leu Val Thr Val Ser Ser
        115                 120


<210> SEQ ID NO 6
<211> LENGTH: 122
<212> TYPE: PRT
<213> ORGANISM: Homo sapiens

<400> SEQUENCE: 6

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ser Asn Ile Arg Ser Asp Gly Ser Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Arg Tyr Trp Ser Lys Ser His Ala Ser Val Thr Asp Tyr Trp
            100                 105                 110

Gly Gln Gly Thr Leu Val Thr Val Ser Ser
        115                 120


<210> SEQ ID NO 7
<211> LENGTH: 122
<212> TYPE: PRT
<213> ORGANISM: Homo sapiens

<400> SEQUENCE: 7

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Asn Ile Tyr Ser Asp Gly Ser Asn Thr Phe Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Met Tyr Arg Trp Pro Phe His Tyr Phe Phe Asp Tyr Trp
            100                 105                 110

Gly Gln Gly Thr Leu Val Thr Val Ser Ser
        115                 120


<210> SEQ ID NO 8
<211> LENGTH: 119
<212> TYPE: PRT
<213> ORGANISM: Homo sapiens

<400> SEQUENCE: 8

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Asn
            20                  25                  30

Gly Met Ser Trp Val Arg Gln Ala Pro Gly Lys Gly Leu Glu Trp Val
        35                  40                  45

Ser Asn Ile Ser Tyr Leu Ser Ser Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Tyr Gly Tyr Phe Asn Tyr Ala Asp Val Trp Gly Gln Gly
            100                 105                 110

Thr Leu Val Thr Val Ser Ser
        115


<210> SEQ ID NO 9
<211> LENGTH: 342
<212> TYPE: DNA
<213> ORGANISM: Homo sapiens

<400> SEQUENCE: 9
```

-continued

```
gatatcgtga tgacccagag cccactgagc ctgccagtga ctccgggcga gcctgcgagc     60

attagctgca gaagcagcca aagcctgctt tttattgatg gcaataatta tctgaattgg    120

taccttcaaa aaccaggtca aagcccgcag ctattaattt atcttggttc taatcgtgcc    180

agtggggtcc cggatcgttt tagcggctct ggatccggca ccgattttac cctgaaaatt    240

agccgtgtgg aagctgaaga cgtgggcgtg tattattgcc agcagtattc ttctaagtct    300

gctacctttg gccagggtac gaaagttgaa attaaacgta cg                       342
```

```
<210> SEQ ID NO 10
<211> LENGTH: 327
<212> TYPE: DNA
<213> ORGANISM: Homo sapiens

<400> SEQUENCE: 10

gatatccaga tgacccagag cccgtctagc ctgagcgcga gcgtgggtga tcgtgtgacc     60

attacctgca gagcgagcca ggatatttct gcttttctga attggtacca gcagaaacca    120

ggtaaagcac cgaaactatt aatttataag gtttctaatt tgcaaagcgg ggtcccgtcc    180

cgttttagcg gctctggatc cggcactgat tttaccctga ccattagcag cctgcaacct    240

gaagactttg cgacttatta ttgccagcag gcttattctg gttctattac ctttggccag    300

ggtacgaaag ttgaaattaa acgtacg                                        327
```

```
<210> SEQ ID NO 11
<211> LENGTH: 324
<212> TYPE: DNA
<213> ORGANISM: Homo sapiens

<400> SEQUENCE: 11

gatatcgaac tgacccagcc gccttcagtg agcgttgcac caggtcagac cgcgcgtatc     60

tcgtgtagcg gcgataatat tggtaataag tatgtttctt ggtaccagca gaaacccggg    120

caggcgccag ttgttgtgat ttatggtgat aataatcgtc cctcaggcat cccggaacgc    180

tttagcggat ccaacagcgg caacaccgcg accctgacca ttagcggcac tcaggcggaa    240

gacgaagcgg attattattg ctcttcttat gattcttctt attttgtgtt tggcggcggc    300

acgaagttaa ccgttcttgg ccag                                           324
```

```
<210> SEQ ID NO 12
<211> LENGTH: 327
<212> TYPE: DNA
<213> ORGANISM: Homo sapiens

<400> SEQUENCE: 12

gatatcgaac tgacccagcc gccttcagtg agcgttgcac caggtcagac cgcgcgtatc     60

tcgtgtagcg gcgataatat tggtcattat tatgcttctt ggtaccagca gaaacccggg    120

caggcgccag ttcttgtgat ttatcgtgat aatgatcgtc cctcaggcat cccggaacgc    180

tttagcggat ccaacagcgg caacaccgcg accctgacca ttagcggcac tcaggcggaa    240

gacgaagcgg attattattg ccagtcttat gattatcttc atgattttgt gtttggcggc    300

ggcacgaagt taaccgttct tggccag                                        327
```

```
<210> SEQ ID NO 13
<211> LENGTH: 114
<212> TYPE: PRT
<213> ORGANISM: Homo sapiens

<400> SEQUENCE: 13
```

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu Phe Ile
             20                  25                  30

Asp Gly Asn Asn Tyr Leu Asn Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Tyr
                 85                  90                  95

Ser Ser Lys Ser Ala Thr Phe Gly Gln Gly Thr Lys Val Glu Ile Lys
            100                 105                 110

Arg Thr


<210> SEQ ID NO 14
<211> LENGTH: 109
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Ala Phe
             20                  25                  30

Leu Asn Trp Tyr Gln Gln Lys Pro Gly Lys Ala Pro Lys Leu Leu Ile
         35                  40                  45

Tyr Lys Val Ser Asn Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Tyr Ser Gly Ser Ile
                 85                  90                  95

Thr Phe Gly Gln Gly Thr Lys Val Glu Ile Lys Arg Thr
            100                 105


<210> SEQ ID NO 15
<211> LENGTH: 108
<212> TYPE: PRT
<213> ORGANISM: Homo sapiens

<400> SEQUENCE: 15

Asp Ile Glu Leu Thr Gln Pro Pro Ser Val Ser Val Ala Pro Gly Gln
  1               5                  10                  15

Thr Ala Arg Ile Ser Cys Ser Gly Asp Asn Ile Gly Asn Lys Tyr Val
             20                  25                  30

Ser Trp Tyr Gln Gln Lys Pro Gly Gln Ala Pro Val Val Val Ile Tyr
         35                  40                  45

Gly Asp Asn Asn Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ser Ser Tyr Asp Ser Ser Tyr Phe Val
                 85                  90                  95
```

Phe Gly Gly Gly Thr Lys Leu Thr Val Leu Gly Gln
            100                 105

<210> SEQ ID NO 16
<211> LENGTH: 109
<212> TYPE: PRT
<213> ORGANISM: Homo sapiens

<400> SEQUENCE: 16

Asp Ile Glu Leu Thr Gln Pro Pro Ser Val Ser Val Ala Pro Gly Gln
  1               5                  10                  15

Thr Ala Arg Ile Ser Cys Ser Gly Asp Asn Ile Gly His Tyr Tyr Ala
             20                  25                  30

Ser Trp Tyr Gln Gln Lys Pro Gly Gln Ala Pro Val Leu Val Ile Tyr
         35                  40                  45

Arg Asp Asn Asp Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Asp Tyr Leu His Asp Phe
                 85                  90                  95

Val Phe Gly Gly Gly Thr Lys Leu Thr Val Leu Gly Gln
            100                 105

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 17

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 18
<211> LENGTH: 120
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 18

Gln Val Gln Leu Val Glu Ser Gly Gly Gly Leu Val Gln Pro Gly Gly

```
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 19

Ser Tyr Glu Leu Thr Gln Pro Pro Ser Val Ser Val Ala Pro Gly Gln
  1               5                  10                  15

Thr Ala Arg Ile Ser Cys Ser Gly Asp Ala Leu Gly Asp Lys Tyr Ala
             20                  25                  30

Ser Trp Tyr Gln Gln Lys Pro Gly Gln Ala Pro Val Leu Val Ile Tyr
         35                  40                  45

Asp Asp Ser Asp Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Gln His Tyr Thr Thr Pro Pro Val
                 85                  90                  95

Phe Gly Gly Gly Thr Lys Leu Thr Val Leu Gly
            100                 105


<210> SEQ ID NO 20
<211> LENGTH: 108
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 20

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Tyr
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
```

```
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg
            100                 105
```

<210> SEQ ID NO 21
<211> LENGTH: 113
<212> TYPE: PRT
<213> ORGANISM: Artificial Sequence
<220> FEATURE:
<223> OTHER INFORMATION: Description of Artificial Sequence: Synthetic consensus sequence

<400> SEQUENCE: 21

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln His
                 85                  90                  95

Tyr Thr Thr Pro Pro Thr Phe Gly Gln Gly Thr Lys Val Glu Ile Lys
            100                 105                 110

Arg
```

<210> SEQ ID NO 22
<211> LENGTH: 300
<212> TYPE: PRT
<213> ORGANISM: Homo sapiens

<400> SEQUENCE: 22

```
Met Ala Asn Cys Glu Phe Ser Pro Val Ser Gly Asp Lys Pro Cys Cys
  1               5                  10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
     50                  55                  60

Ala Arg Cys Val Lys Tyr Thr Glu Ile His Pro Glu Met Arg His Val
 65                  70                  75                  80

Asp Cys Gln Ser Val Trp Asp Ala Phe Lys Gly Ala Phe Ile Ser Lys
                 85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
    130                 135                 140

Leu Glu Asp Thr Leu Leu Gly Tyr Leu Ala Asp Asp Leu Thr Trp Cys
145                 150                 155                 160
```

Gly Glu Phe Asn Thr Ser Lys Ile Asn Tyr Gln Ser Cys Pro Asp Trp
165 170 175

Arg Lys Asp Cys Ser Asn Asn Pro Val Ser Val Phe Trp Lys Thr Val
180 185 190

Ser Arg Arg Phe Ala Glu Ala Ala Cys Asp Val Val His Val Met Leu
195 200 205

Asn Gly Ser Arg Ser Lys Ile Phe Asp Lys Asn Ser Thr Phe Gly Ser
210 215 220

Val Glu Val His Asn Leu Gln Pro Glu Lys Val Gln Thr Leu Glu Ala
225 230 235 240

Trp Val Ile His Gly Gly Arg Glu Asp Ser Arg Asp Leu Cys Gln Asp
245 250 255

Pro Thr Ile Lys Glu Leu Glu Ser Ile Ile Ser Lys Arg Asn Ile Gln
260 265 270

Phe Ser Cys Lys Asn Ile Tyr Arg Pro Asp Lys Phe Leu Gln Cys Val
275 280 285

Lys Asn Pro Glu Asp Ser Ser Cys Thr Ser Glu Ile
290 295 300

<210> SEQ ID NO 23
<211> LENGTH: 1317
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 23
caggtggaat tggtggaatc tggaggatcc ctgaaactct cctgtgcagc ctcaggattc 60
gattttagta gatcctggat gaattgggtc cggcaggctc caggaaaagg gctagaatgg 120
attggagaaa ttaatccaga tagcagtacg ataaactata cgacatctct aaaggataaa 180
ttcatcatct ccagagacaa cgccaaaaat acgctgtacc tgcaaatgac caaagtgaga 240
tctgaggaca cagcccttta ttactgtgca agatatggta actggtttcc ttattggggc 300
caagggactc tggtcactgt cagctcagcc tccaccaagg gtccatcggt cttccccctg 360
gcaccctcct ccaagagcac ctctgggggc acagcggccc tgggctgcct ggtcaaggac 420
tacttccccg aaccggtgac ggtgtcgtgg aactcaggcg ccctgaccag cggcgtgcac 480
accttcccgg ctgtcctaca gtcctcagga ctctactccc tcagcagcgt ggtgaccgtg 540
ccctccagca gcttgggcac ccagacctac atctgcaacg tgaatcacaa gcccagcaac 600
accaaggtgg acaagaaagt tgagcccaaa tcttgtgaca aaactcacac atgcccaccg 660
tgcccagcac ctgaactcct ggggggaccg tcagtcttcc tcttcccccc aaaacccaag 720
gacaccctca tgatctcccg gacccctgag gtcacatgcg tggtggtgga cgtgagccac 780
gaagaccctg aggtcaagtt caactggtac gtggacggcg tggaggtgca taatgccaag 840
acaaagccgc gggaggagca gtacaacagc acgtaccggg tggtcagcgt cctcaccgtc 900
ctgcaccagg actggctgaa tggcaaggag tacaagtgca aggtctccaa caaagccctc 960
ccagccccca tcgagaaaac catctccaaa gccaaagggc agccccgaga accacaggtg 1020
tacaccctgc ccccatcccg ggatgagctg accaagaacc aggtcagcct gacctgcctg 1080
gtcaaaggct tctatcccag cgacatcgcc gtggagtggg agagcaatgg gcagccggag 1140
aacaactaca agaccacgcc tcccgtgctg gactccgacg gctccttctt cctctacagc 1200

-continued aagctcaccg tggacaagag caggtggcag caggggaacg tcttctcatg ctccgtgatg 1260
catgaggctc tgcacaacca ctacacgcag aagagcctct ccctgtctcc gggtaaa 1317

<210> SEQ ID NO 24
<211> LENGTH: 642
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 24
gatatcctga tgacccagtc tcaaaaaatc atgcccacat cagtgggaga cagggtcagc 60
gtcacctgca aggccagtca aaatgtggat actaatgtag cctggtatca acagaaacca 120
ggacagtctc ctaaagcact gatttactcg gcatcctacc gatacagtgg agtccctgat 180
cgcttcacag gcagtggatc tgggacagat ttcactctca ccatcaccaa tgtgcagtct 240
gaggacttgg cagagtattt ctgtcagcaa tatgacagct atcctctcac gttcggtgct 300
gggaccaagc tggacctgaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
atggccaact gcgagttcag c 21

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
tcagatctca gatgtgcaag atgaatc 27

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
ttggtaccag gtggcgccag cagtg 25

<210> SEQ ID NO 28
<211> LENGTH: 23

-continued

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ttggtaccat ggccaactgc gag 23

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccgatatcag atctcagatg tgcaagatg 29

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccgatatcga tctcagatgt gcaagatg 28

<210> SEQ ID NO 31
<211> LENGTH: 363
<212> TYPE: DNA
<213> ORGANISM: Homo sapiens

<400> SEQUENCE: 31
caggtgcaat tagtccaaag tggtgcggaa gtgaaaaaac cgggcgcgag cgtgaaagtg 60
agctgcaaag cctccggata tacctttact tcttattcta ttaattgggt ccgccaagcc 120
cctgggcagg gtctcgagtg gatgggctat atcgatccga atcgtggcaa tacgaattac 180
gcgcagaagt ttcagggccg ggtgaccatg acccgtgata ccagcattag caccgcgtat 240
atggaactga gcagcctgcg tagcgaagat acggccgtgt attattgcgc gcgtgagtat 300
atttatttta ttcatggtat gcttgatttt tggggccaag gcaccctggt gacggttagc 360
tca 363

<210> SEQ ID NO 32
<211> LENGTH: 1500
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (307)..(393)

<400> SEQUENCE: 32
tcgctattac catggtgatg cggttttggc agtacatcaa tgggcgtgga tagcggtttg 60
actcacgggg atttccaagt ctccacccca ttgacgtcaa tgggagtttg ttttggcacc 120
aaaatcaacg ggactttcca aaatgtcgta acaactccgc cccattgacg caaatgggcg 180
gtaggcgtgt acggtgggag gtctatataa gcagagctct ctggctaact agagaaccca 240

```
ctgcttactg gcttatcgaa attaatacga ctcactatag ggagacccaa gctggctagc    300

gccacc atg aaa cac ctg tgg ttc ttc ctc ctg ctg gtg gca gct ccc       348
       Met Lys His Leu Trp Phe Phe Leu Leu Leu Val Ala Ala Pro
         1               5                  10

aga tgg gtc ctg tcc cag gtg gaa ttc tgc agg cgg tta gct cag          393
Arg Trp Val Leu Ser Gln Val Glu Phe Cys Arg Arg Leu Ala Gln
 15                  20                  25

cctccaccaa gggtccatcg gtcttccccc tggcaccctc ctccaagagc acctctgggg    453

gcacagcggc cctgggctgc ctggtcaagg actacttccc cgaaccggtg acggtgtcgt    513

ggaactcagg cgccctgacc agcggcgtgc acaccttccc ggctgtccta cagtcctcag    573

gactctactc cctcagcagc gtggtgaccg tgccctccag cagcttgggc acccagacct    633

acatctgcaa cgtgaatcac aagcccagca acaccaaggt ggacaagaaa gttgagccca    693

aatcttgtga caaaactcac acatgcccac cgtgcccagc acctgaactc ctggggggac    753

cgtcagtctt cctcttcccc ccaaaaccca aggacaccct catgatctcc cggacccctg    813

aggtcacatg cgtggtggtg gacgtgagcc acgaagaccc tgaggtcaag ttcaactggt    873

acgtggacgg cgtggaggtg cataatgcca agacaaagcc gcgggaggag cagtacaaca    933

gcacgtaccg ggtggtcagc gtcctcaccg tcctgcacca ggactggctg aatggcaagg    993

agtacaagtg caaggtctcc aacaaagccc tcccagcccc catcgagaaa accatctcca   1053

aagccaaagg gcagccccga gaaccacagg tgtacaccct gcccccatcc cgggatgagc   1113

tgaccaagaa ccaggtcagc ctgacctgcc tggtcaaagg cttctatccc agcgacatcg   1173

ccgtggagtg ggagagcaat gggcagccgg agaacaacta caagaccacg cctcccgtgc   1233

tggactccga cggctccttc ttcctctaca gcaagctcac cgtggacaag agcaggtggc   1293

agcaggggaa cgtcttctca tgctccgtga tgcatgaggc tctgcacaac cactacacgc   1353

agaagagcct ctccctgtct ccgggtaaat gagggcccgt ttaaacccgc tgatcagcct   1413

cgactgtgcc ttctagttgc cagccatctg ttgtttgccc ctcccccgtg ccttccttga   1473

ccctggaagg tgccactccc actgtcc                                       1500


<210> SEQ ID NO 33
<211> LENGTH: 800
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (307)..(705)

<400> SEQUENCE: 33

tcgctattac catggtgatg cggttttggc agtacatcaa tgggcgtgga tagcggtttg     60

actcacgggg atttccaagt ctccacccca ttgacgtcaa tgggagtttg ttttggcacc    120

aaaatcaacg ggactttcca aaatgtcgta acaactccgc cccattgacg caaatgggcg    180

gtaggcgtgt acggtgggag gtctatataa gcagagctct ctggctaact agagaaccca    240

ctgcttactg gcttatcgaa attaatacga ctcactatag ggagacccaa gctggctagc    300

gccacc atg gtg ttg cag acc cag gtc ttc att tct ctg ttg ctc tgg       348
       Met Val Leu Gln Thr Gln Val Phe Ile Ser Leu Leu Leu Trp
         1               5                  10

atc tct ggt gcc tac ggg gat atc gtg atg att aaa cgt acg gtg gct      396
Ile Ser Gly Ala Tyr Gly Asp Ile Val Met Ile Lys Arg Thr Val Ala
```

-continued

```
 15                  20                  25                  30

gca cca tct gtc ttc atc ttc ccg cca tct gat gag cag ttg aaa tct      444
Ala Pro Ser Val Phe Ile Phe Pro Pro Ser Asp Glu Gln Leu Lys Ser
                 35                  40                  45

gga act gcc tct gtt gtg tgc ctg ctg aat aac ttc tat ccc aga gag      492
Gly Thr Ala Ser Val Val Cys Leu Leu Asn Asn Phe Tyr Pro Arg Glu
             50                  55                  60

gcc aaa gta cag tgg aag gtg gat aac gcc ctc caa tcg ggt aac tcc      540
Ala Lys Val Gln Trp Lys Val Asp Asn Ala Leu Gln Ser Gly Asn Ser
         65                  70                  75

cag gag agt gtc aca gag cag gac agc aag gac agc acc tac agc ctc      588
Gln Glu Ser Val Thr Glu Gln Asp Ser Lys Asp Ser Thr Tyr Ser Leu
     80                  85                  90

agc agc acc ctg acg ctg agc aaa gca gac tac gag aaa cac aaa gtc      636
Ser Ser Thr Leu Thr Leu Ser Lys Ala Asp Tyr Glu Lys His Lys Val
 95                 100                 105                 110

tac gcc tgc gaa gtc acc cat cag ggc ctg agc tcg ccc gtc aca aag      684
Tyr Ala Cys Glu Val Thr His Gln Gly Leu Ser Ser Pro Val Thr Lys
                115                 120                 125

agc ttc aac agg gga gag tgt taggggcccg tttaaacccg ctgatcagcc         735
Ser Phe Asn Arg Gly Glu Cys
            130

tcgactgtgc cttctagttg ccagccatct gttgtttgcc cctcccccgt gccttccttg    795

accct                                                                800


<210> SEQ ID NO 34
<211> LENGTH: 800
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (307)..(384)

<400> SEQUENCE: 34

tcgctattac catggtgatg cggttttggc agtacatcaa tgggcgtgga tagcggtttg     60

actcacgggg atttccaagt ctccacccca ttgacgtcaa tgggagtttg ttttggcacc    120

aaaatcaacg ggactttcca aaatgtcgta acaactccgc cccattgacg caaatgggcg    180

gtaggcgtgt acggtgggag gtctatataa gcagagctct ctggctaact agagaaccca    240

ctgcttactg gcttatcgaa attaatacga ctcactatag ggagacccaa gctggctagc    300

gccacc atg gcc tgg gct ctg ctg ctc ctc acc ctc ctc act cag ggc       348
       Met Ala Trp Ala Leu Leu Leu Leu Thr Leu Leu Thr Gln Gly
         1               5                  10

aca gga tcc tgg gct gat atc gtg atg cac gaa gtt aaccgtccta           394
Thr Gly Ser Trp Ala Asp Ile Val Met His Glu Val
 15                  20                  25

ggtcagccca aggctgcccc ctcggtcact ctgttcccgc cctcctctga ggagcttcaa    454

gccaacaagg ccacactggt gtgtctcata agtgacttct acccgggagc cgtgacagtg    514

gcctggaagg gagatagcag ccccgtcaag gcgggagtgg agaccaccac accctccaaa    574

caaagcaaca acaagtacgc ggccagcagc tatctgagcc tgacgcctga gcagtggaag    634

tcccacagaa gctacagctg ccaggtcacg catgaaggga gcaccgtgga gaagacagtg    694

gcccctacag aatgttcata ggggcccgtt taaacccgct gatcagcctc gactgtgcct    754

tctagttgcc agccatctgt tgtttgcccc tcccccgtgc cttcct                   800
```

<210> SEQ ID NO 35
<211> LENGTH: 29
<212> TYPE: PRT
<213> ORGANISM: Artificial Sequence
<220> FEATURE:
<223> OTHER INFORMATION: Description of Artificial Sequence: Synthetic construct

<400> SEQUENCE: 35

```
Met Lys His Leu Trp Phe Phe Leu Leu Leu Val Ala Ala Pro Arg Trp
  1               5                  10                  15

Val Leu Ser Gln Val Glu Phe Cys Arg Arg Leu Ala Gln
            20                  25
```

<210> SEQ ID NO 36
<211> LENGTH: 330
<212> TYPE: PRT
<213> ORGANISM: Artificial Sequence
<220> FEATURE:
<223> OTHER INFORMATION: Description of Artificial Sequence: Synthetic construct

<400> SEQUENCE: 36

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 37
<211> LENGTH: 133
<212> TYPE: PRT
<213> ORGANISM: Artificial Sequence
<220> FEATURE:
<223> OTHER INFORMATION: Description of Artificial Sequence: Synthetic construct

<400> SEQUENCE: 37

Met Val Leu Gln Thr Gln Val Phe Ile Ser Leu Leu Leu Trp Ile Ser
1 5 10 15

Gly Ala Tyr Gly Asp Ile Val Met Ile Lys Arg Thr Val Ala Ala Pro
20 25 30

Ser Val Phe Ile Phe Pro Pro Ser Asp Glu Gln Leu Lys Ser Gly Thr
35 40 45

Ala Ser Val Val Cys Leu Leu Asn Asn Phe Tyr Pro Arg Glu Ala Lys
50 55 60

Val Gln Trp Lys Val Asp Asn Ala Leu Gln Ser Gly Asn Ser Gln Glu
65 70 75 80

Ser Val Thr Glu Gln Asp Ser Lys Asp Ser Thr Tyr Ser Leu Ser Ser
85 90 95

Thr Leu Thr Leu Ser Lys Ala Asp Tyr Glu Lys His Lys Val Tyr Ala
100 105 110

Cys Glu Val Thr His Gln Gly Leu Ser Ser Pro Val Thr Lys Ser Phe
115 120 125

Asn Arg Gly Glu Cys
130

<210> SEQ ID NO 38
<211> LENGTH: 26
<212> TYPE: PRT
<213> ORGANISM: Artificial Sequence
<220> FEATURE:
<223> OTHER INFORMATION: Description of Artificial Sequence: Synthetic construct

<400> SEQUENCE: 38

Met Ala Trp Ala Leu Leu Leu Leu Thr Leu Leu Thr Gln Gly Thr Gly
1 5 10 15

Ser Trp Ala Asp Ile Val Met His Glu Val
20 25

<210> SEQ ID NO 39
<211> LENGTH: 109
<212> TYPE: PRT
<213> ORGANISM: Artificial Sequence
<220> FEATURE:
<223> OTHER INFORMATION: Description of Artificial Sequence: Synthetic construct

<400> SEQUENCE: 39

-continued

```
Thr Val Leu Gly Gln Pro Lys Ala Ala Pro Ser Val Thr Leu Phe Pro
  1               5                  10                  15

Pro Ser Ser Glu Glu Leu Gln Ala Asn Lys Ala Thr Leu Val Cys Leu
             20                  25                  30

Ile Ser Asp Phe Tyr Pro Gly Ala Val Thr Val Ala Trp Lys Gly Asp
         35                  40                  45

Ser Ser Pro Val Lys Ala Gly Val Glu Thr Thr Thr Pro Ser Lys Gln
     50                  55                  60

Ser Asn Asn Lys Tyr Ala Ala Ser Ser Tyr Leu Ser Leu Thr Pro Glu
 65                  70                  75                  80

Gln Trp Lys Ser His Arg Ser Tyr Ser Cys Gln Val Thr His Glu Gly
                 85                  90                  95

Ser Thr Val Glu Lys Thr Val Ala Pro Thr Glu Cys Ser
            100                 105


<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Val Ser Arg Arg Phe Ala Glu Ala Ala Cys Asp Val Val His Val
  1               5                  10                  15


<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Phe Leu Gln Cys Val Lys Asn Pro Glu Asp Ser Ser Cys Thr Ser
  1               5                  10                  15


<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Gln Ser Val Trp Asp Ala Phe Lys Gly Ala Phe Ile
  1               5                  10


<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Trp Cys Gly Glu Phe Asn Thr Ser Lys Ile Asn Tyr
  1               5                  10


<210> SEQ ID NO 44
```

<211> LENGTH: 13
<212> TYPE: PRT
<213> ORGANISM: Homo sapiens

<400> SEQUENCE: 44

Cys Gln Ser Val Trp Asp Ala Phe Lys Gly Ala Phe Ile
1 5 10

<210> SEQ ID NO 45
<211> LENGTH: 13
<212> TYPE: PRT
<213> ORGANISM: Macaca fascicularis

<400> SEQUENCE: 45

Cys Gln Ser Val Trp Asp Ala Phe Lys Gly Ala Phe Ile
1 5 10

<210> SEQ ID NO 46
<211> LENGTH: 13
<212> TYPE: PRT
<213> ORGANISM: Rattus sp.

<400> SEQUENCE: 46

Cys Lys Lys Ile Leu Ser Thr Phe Lys Arg Gly Phe Ile
1 5 10

<210> SEQ ID NO 47
<211> LENGTH: 13
<212> TYPE: PRT
<213> ORGANISM: Mus musculus

<400> SEQUENCE: 47

Cys Gln Glu Ile Leu Ser Thr Phe Lys Gly Ala Phe Val
1 5 10

<210> SEQ ID NO 48
<211> LENGTH: 13
<212> TYPE: PRT
<213> ORGANISM: Oryctolagus sp.

<400> SEQUENCE: 48

Cys Lys Lys Ile Leu Asn Thr Phe Thr Ser Ala Phe Val
1 5 10

<210> SEQ ID NO 49
<211> LENGTH: 13
<212> TYPE: PRT
<213> ORGANISM: Canis sp.

<400> SEQUENCE: 49

Cys Gln Lys Ile Gly Lys Ala Phe Thr Ser Ala Phe Leu
1 5 10

<210> SEQ ID NO 50
<211> LENGTH: 13
<212> TYPE: PRT
<213> ORGANISM: Homo sapiens

<400> SEQUENCE: 50

Thr Trp Cys Gly Glu Phe Asn Thr Ser Lys Ile Asn Tyr
1 5 10

<210> SEQ ID NO 51
<211> LENGTH: 13
<212> TYPE: PRT

<213> ORGANISM: Macaca fascicularis

<400> SEQUENCE: 51

Thr Trp Cys Gly Glu Phe Asn Thr Phe Glu Ile Asn Tyr
1 5 10

<210> SEQ ID NO 52
<211> LENGTH: 13
<212> TYPE: PRT
<213> ORGANISM: Rattus sp.

<400> SEQUENCE: 52

Arg Trp Cys Gly Asp Pro Ser Thr Ser Asp Met Asn Tyr
1 5 10

<210> SEQ ID NO 53
<211> LENGTH: 13
<212> TYPE: PRT
<213> ORGANISM: Mus musculus

<400> SEQUENCE: 53

Arg Trp Cys Gly Asp Pro Ser Thr Ser Asp Met Asn Tyr
1 5 10

<210> SEQ ID NO 54
<211> LENGTH: 13
<212> TYPE: PRT
<213> ORGANISM: Oryctolagus sp.

<400> SEQUENCE: 54

Val Met Cys Gly Asp Pro Arg Thr Ser Glu Val Lys Glu
1 5 10

<210> SEQ ID NO 55
<211> LENGTH: 13
<212> TYPE: PRT
<213> ORGANISM: Canis sp.

<400> SEQUENCE: 55

Lys Trp Cys Gly Asp Thr Ser Ser Ser Glu Met Asn Tyr
1 5 10

<210> SEQ ID NO 56
<211> LENGTH: 19
<212> TYPE: PRT
<213> ORGANISM: Homo sapiens

<400> SEQUENCE: 56

Arg Pro Asp Lys Phe Leu Gln Cys Val Lys Asn Pro Glu Asp Ser Ser
1 5 10 15

Cys Thr Ser

<210> SEQ ID NO 57
<211> LENGTH: 19
<212> TYPE: PRT
<213> ORGANISM: Macaca fascicularis

<400> SEQUENCE: 57

Arg Pro Asp Lys Phe Leu Gln Cys Val Lys Asn Pro Glu Asp Ser Ser
1 5 10 15

Cys Leu Ser

<210> SEQ ID NO 58

<211> LENGTH: 19
<212> TYPE: PRT
<213> ORGANISM: Rattus sp.

<400> SEQUENCE: 58

```
Arg Pro Val Arg Phe Leu Gln Cys Val Lys Asn Pro Glu His Pro Ser
  1               5                  10                  15

Cys Arg Leu
```

<210> SEQ ID NO 59
<211> LENGTH: 19
<212> TYPE: PRT
<213> ORGANISM: Mus musculus

<400> SEQUENCE: 59

```
Arg Pro Ala Arg Phe Leu Gln Cys Val Lys Asn Pro Glu His Pro Ser
  1               5                  10                  15

Cys Arg Leu
```

<210> SEQ ID NO 60
<211> LENGTH: 19
<212> TYPE: PRT
<213> ORGANISM: Oryctolagus sp.

<400> SEQUENCE: 60

```
Arg Pro Ala Arg Phe Val Gln Cys Val Arg His Pro Glu His Pro Ser
  1               5                  10                  15

Cys Ser Val
```

<210> SEQ ID NO 61
<211> LENGTH: 19
<212> TYPE: PRT
<213> ORGANISM: Canis sp.

<400> SEQUENCE: 61

```
Arg Pro Val Arg Leu Leu Gln Cys Val Lys Asn Pro Glu His Ser Ser
  1               5                  10                  15

Cys Lys Tyr
```

<210> SEQ ID NO 62
<211> LENGTH: 15
<212> TYPE: PRT
<213> ORGANISM: Homo sapiens

<400> SEQUENCE: 62

```
Val Ser Arg Arg Phe Ala Glu Ala Ala Cys Asp Val Val His Val
  1               5                  10                  15
```

<210> SEQ ID NO 63
<211> LENGTH: 15
<212> TYPE: PRT
<213> ORGANISM: Macaca fascicularis

<400> SEQUENCE: 63

```
Val Ser Arg Arg Phe Ala Glu Thr Ala Cys Gly Val Val His Val
  1               5                  10                  15
```

<210> SEQ ID NO 64
<211> LENGTH: 15
<212> TYPE: PRT
<213> ORGANISM: Rattus sp.

<400> SEQUENCE: 64

-continued

```
Ile Ser Gln Lys Phe Ala Glu Asp Ala Cys Gly Val Val Gln Val
  1               5                  10                  15


<210> SEQ ID NO 65
<211> LENGTH: 15
<212> TYPE: PRT
<213> ORGANISM: Mus musculus

<400> SEQUENCE: 65

Ile Ser Gln Lys Phe Ala Glu Asp Ala Cys Gly Val Val Gln Val
  1               5                  10                  15


<210> SEQ ID NO 66
<211> LENGTH: 15
<212> TYPE: PRT
<213> ORGANISM: Oryctolagus sp.

<400> SEQUENCE: 66

Val Ser Arg Lys Phe Ala Glu Ser Ala Cys Gly Thr Val Tyr Val
  1               5                  10                  15


<210> SEQ ID NO 67
<211> LENGTH: 15
<212> TYPE: PRT
<213> ORGANISM: Canis sp.

<400> SEQUENCE: 67

Val Ser Lys Arg Phe Ala Glu Asp Ala Cys Gly Val Val His Val
  1               5                  10                  15
```

GENERATION AND PROFILING OF FULLY HUMAN HUCAL GOLD®-DERIVED THERAPEUTIC ANTIBODIES SPECIFIC FOR HUMAN CD3I

CROSS-REFERENCE TO RELATED APPLICATIONS

This application is a continuation of U.S. application Ser. No. 11/920,830, which is the U.S. National Stage application of PCT/EP2006/004991, filed May 24, 2006, which was published in English on Nov. 30, 2006, as WO 2006/125640; which claims the benefit of priority from U.S. Provisional Applications 60/683,772, filed May 24, 2005, and 60/706,004, filed Aug. 8, 2005.

This application is also a continuation-in-part of U.S. application Ser. No. 10/588,568, now U.S. Pat. No. 8,263,746, which is the U.S. National Stage application of PCT/1B2005/002476, filed Feb. 7, 2005, which was published in English as WO 2005/103083 on Nov. 3, 2005; which claims the benefit of priority from US Provisional Application Nos. 60/541,911, filed Feb. 6, 2004; 60/547,584, filed Feb. 26, 2004; 60/553,948, filed Mar. 18, 2004; 60/599,014, filed Aug. 6, 2004; and 60/614,471, filed Oct. 1, 2004.

The instant application contains a Sequence Listing which has been submitted in ASCII format via EFS-WEB and is hereby incorporated by reference in its entirety. Said ASCII copy, created on Nov. 21, 2011, is named sequence.txt and is 45 KB.

The foregoing disclosures are incorporated by reference.

SUMMARY OF THE INVENTION

It is an object of the present invention to provide a method of inducing specific killing of tumor cells that express CD38. In one aspect, the specific killing of tumor cells occurs by CD38 cross-linking through incubating CD38-expressing tumor cells in the presence of a sufficient amount of a human or humanized anti-CD38 antibody or a functional fragment thereof and a control antibody designated as anti-CD20 under conditions that permit cross-linking, and detecting the specific killing activity of the human or humanized anti-CD38 antibody or functional fragment thereof. Preferably, the specific killing activity of the human or humanized anti-CD38 antibody is at least 2-fold, 3-fold, 4-fold or 5-fold better than the specific killing activity of the control antibody.

It is also an object of the present invention to provide a method of inducing specific killing of tumor cells that express CD38, by CD38 cross-linking, through administering to a subject in need thereof an effective amount of a human or humanized anti-CD38 antibody or a functional fragment thereof, and detecting the specific killing activity of the human or humanized anti-CD38 antibody or the functional fragment thereof. Such tumor cells can be of human, minipig or rabbit origin.

In one aspect, the invention provides a human or humanized anti-CD38 antibody or a functional fragment thereof that can be used in a method of inducing specific killing of tumor cells. Such an antibody or functional fragment thereof may contain a variable heavy chain depicted in SEQ ID NO: 1 (DNA), 5 (protein), 2 (DNA), 6 (protein), 3 (DNA), 7 (protein) or 4 (DNA), 8 (protein); and/or a light chain depicted in SEQ ID NO: 9 (DNA), 13 (protein), 10 (DNA), 14 (protein), 11 (DNA), 15 (protein) or 12.

It is also an object of the present invention to provide a method of detecting the presence of CD38 in a tissue or a cell of minipig origin, comprising the steps of allowing a human or humanized anti-CD38 antibody or a functional fragment thereof to come into contact with CD38 and detecting the specific binding of the human or humanized anti-CD38 antibody or functional fragment thereof to the CD38, where the antibody or functional fragment thereof is also able to specifically bind to CD38 of human origin. CD38 of minipig origin may be comprised within an isolated cell type selected from the group consisting of peripheral blood monocyte, erythrocyte, lymphocyte, thymocyte, muscle cell, cerebellum cell, pancreas cell, lymph-node cell, tonsil cell, spleen cell, prostate cell, skin cell and a cell of the retina.

Such a human or humanized anti-CD38 antibody or a functional fragment thereof may contain a heavy chain depicted in SEQ ID NO: 1 (DNA), 5 (protein); and/or a light chain depicted in SEQ ID NO: 9 (DNA), 13 (protein) and may have at least 60 percent identity in the heavy chain regions depicted in SEQ ID NO: 1 (DNA), 5 (protein) and/or may have at least 60 percent identity in the light chain regions depicted in SEQ ID NO 9 (DNA), 13 (protein).

It is another object of the present invention to provide a method of detecting CD38 in a CD38-expressing erythrocyte, by allowing a human or humanized anti-CD38 antibody or a functional fragment thereof to come into contact with CD38-expressing erythrocytes, and detecting the specific binding of the human or humanized anti-CD38 antibody or functional fragment thereof to the CD38-expressing erythrocytes, where the antibody or functional fragment thereof is also able to specifically bind to human CD38 from a cell or tissue other than human erythrocytes. Such a cell can be a human lymphocyte. Such a human or humanized anti-CD38 antibody or functional fragment thereof may contain a heavy chain depicted in SEQ ID NO: 2 (DNA), 6 (protein) or 3 (DNA), 7 (protein); and/or a light chain depicted in SEQ ID NO: 10 (DNA), 14 (protein) or 11 (DNA), 15 (protein) and may have at least 60 percent identity in the heavy chain regions depicted in SEQ ID NO 2 (DNA), 6 (protein) or 3 (DNA), 7 (protein) and at least 60 percent identity in the light chain regions depicted in SEQ ID NO: 10 (DNA), 14 (protein) or 11 (DNA), 15 (protein).

Finally, the present invention relates to a method for inducing specific killing, wherein the specific killing which occurs by CD38 cross-linking additionally is caused by antibody-dependent cellular cytotoxicity and/or complement-dependent cytotoxicity

BRIEF DESCRIPTION OF THE FIGURES

FIG. 1*a* provides nucleic acid sequences of various antibody variable heavy regions for use in the present invention.

FIG. 1*b* provides amino acid sequences of various antibody variable heavy regions for use in the present invention. CDR regions HCDR1, HCDR2 and HCDR3 are designated from N- to C-terminus in boldface.

FIG. 2*a* provides nucleic acid sequences of various antibody variable light regions for use in the present invention.

FIG. 2*b* provides amino acid sequences of various antibody variable light regions for use in the present invention. CDR regions LCDR1, LCDR2 and LCDR3 are designated from N- to C-terminus in boldface.

FIG. 3 provides amino acid sequences of variable heavy regions of various consensus-based HuCAL® antibody master gene sequences. CDR regions HCDR1, HCDR2 and HCDR3 are designated from N- to C-terminus in boldface.

FIG. 4 provides amino acid sequences of variable light regions of various consensus-based HuCAL® antibody master gene sequences. CDR regions LCDR1, LCDR2 and LCDR3 are designated from N- to C-terminus in boldface.

FIG. 5 provides, the amino acid sequence of CD38 (SWISS-PROT primary accession number P28907).

FIG. 6 provides the nucleotide sequences of the heavy and light chains of chimeric OKT10.

FIG. 7 provides a schematic overview of epitopes of representative antibodies of the present invention.

FIG. 8 provides the DNA sequence of pMORPH®_h_IgG1_1 (bp 601-2100) (SEQ ID NO: 32): The vector is based on the pcDNA3.1+ vectors (Invitrogen). The amino acid sequence of the VH-stuffer sequence is indicated in bold, whereas the final reading frames of the VH-leader sequence and the constant region gene are printed in non-bold. Restriction sites are indicated above the sequence. The priming sites of the sequencing primers are underlined. Proteins are disclosed as SEQ ID NOS 35 & 36, respectively in order of appearance.

FIG. 9 provides the DNA sequence of Ig kappa light chain expression vector pMORPH® _h_Igκ_1 (bp 601-1400) (SEQ ID NO: 33): The vector is based on the pcDNA3.1+ vectors (Invitrogen). The amino acid sequences of the Vκ-stuffer sequence is indicated in bold, whereas the final reading frames of the Vκ-leader sequence and of the constant region gene are printed in non-bold. Restriction sites are indicated above the sequence. The priming sites of the sequencing primers are underlined. Protein is disclosed as SEQ ID NO: 37.

FIG. 10 provides the DNA sequence of HuCAL® Ig lambda light chain vector pMORPHO®_h_Igλ_1 (bp 601-1400) (SEQ ID NO: 34): The amino acid sequence of the Vλ-stuffer sequence is indicated in bold, whereas the final reading frames of the Vλ-leader sequence and of the constant region gene are printed in non-bold. Restriction sites are indicated above the sequence. The priming sites of the sequencing primers are underlined. Proteins are disclosed as SEQ ID NOS 38 & 39, respectively in order of appearance.

FIG. 11: PBMCs from 4-6 different human donors (as indicated by individual dots) were incubated with MOR03077, 03079, 03080, 03100 and the chimeric OKT10. The agonistic murine monoclonal antibody IB4 and phytohemagglutinine (PHA) served as positive controls for the induction of IL-6 (panel A), IFN-γ (panel B), and proliferation—(panel C). For detection of proliferation a standard BrdU-assay was applied and incorporation measured via chemiluminescence (in relative light units; RLU). IFN-γ and IL-6 release into the cell culture supernatant were analyzed according to a given standard in pg/ml (IFN-γ) or increase in RLU (IL-6) using an ELISA set-up. An irrelevant HuCAL® antibody served as negative control (NC).

Figure 17:
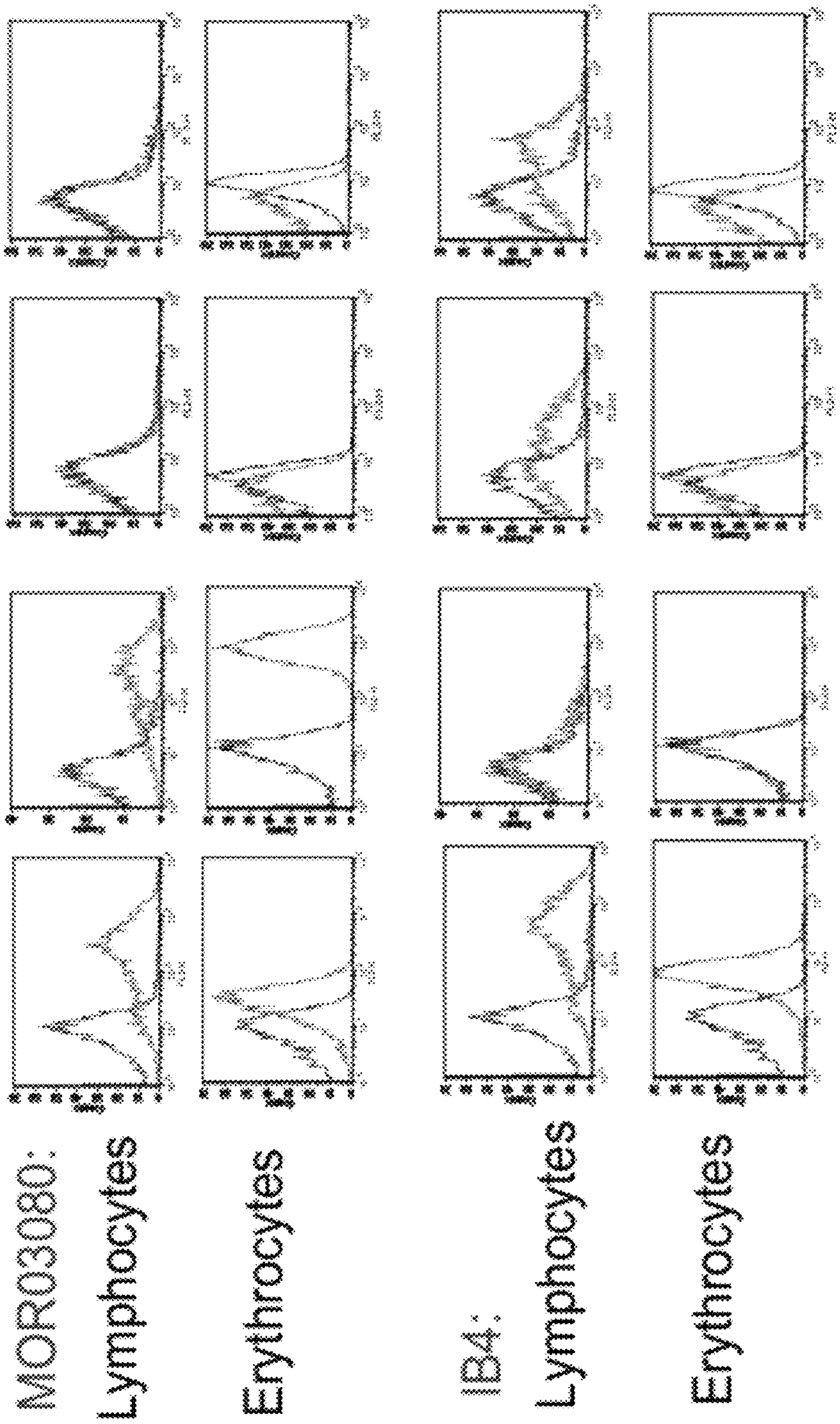
Figure 17:
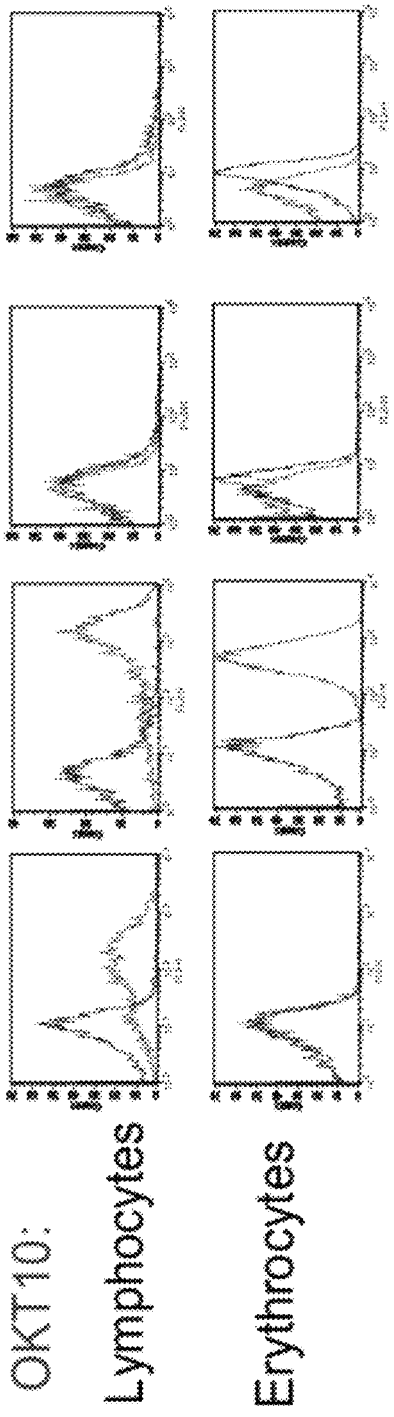

PBMCs for proliferation assay were cultured for 3 days, PBMCs for IL-6 and IFN γ—Release Assay were cultured for 24 hours in the presence of the respective antibodie(s).

FIG. 12: hCD38 Fc fusion proteins (aa 45-300 or aa 45-273) as well as the control antigens bovine serum albumine (BSA) and lysozyme were directly coated onto ELISA wells at concentrations of 5 μg/ml followed by a blocking step and the addition of 10 μg/ml of different anti-hCD38 antibodies as fully human or chimeric IgG1 (A: chOKT10, hu03077, hu03079, hu03080, hu03100) or murine IgG2a (B: mu03079, mu03080, muIB4) or IgG1 isotypes (B: murine OKT10). Bound antibodies were detected via anti-human or anti-murine Fab alkaline phosphatase conjugates (Conj.) in a fluorescence-based read-out (Excitation-wavelength at 430 nm; Emission-wavelength: 535 nm).

FIG. 13 provides data about the cytotoxicity towards CD34+/CD38+ progenitor cells: PBMCs from healthy donors harboring autologous CD34+/CD38+ progenitor cells were incubated with HuCAL® Mab#1 (=MOR03077), Mab#2 (=MOR03079), and Mab#3 (=MOR03080), the positive control (PC=chOKT10) and an irrelevant HuCAL® negative control for 4 hours, respectively. Afterwards, the cell suspension was mixed with conditioned methyl-cellulose medium and incubated for 2 weeks. Colony forming units (CFU) derived from erythroid burst forming units (BFU-E; panel B) and granulocyte/erythroid/macrophage/megakaryocyte stem cells (CFU-GEMM; panels B) and granulocyte/macrophage stem cells (CFU-GM; panel C) were counted and normalized against the medium control ("none"=medium). Panel A represents the total number of CFU (Total CFUc) for all progenitors. Mean values from at least 10 different PBMC donors are given. Error bars represent standard error of the mean.

FIG. 14 provides data about ADCC with different cell-lines:

a: Single measurements (except for RPMI8226: average from 4 indiv. Assays); E:T-ratio: 30:1 b: Namba et al., 1989 c: 5 μg/ml used for antibody conc. (except for Raji with 0.1 μg/ml)

d: Addition of retinoic assay for stimulation of CD38-expression specific killing $$[\%]=[(\text{exp. killing}-\text{medium killing})/(1-\text{medium killing})]*100$$

PC: Positive control (=chOKT10)

MM: Multiple myeloma

CLL: Chronic B-cell leukemia

ALL: Acute lymphoblastic leukemia

AML: Acute myeloid leukemia

DSMZ: Deutsche Sammlung für Mikroorganismen and Zellkulturen GmbH

ATCC: American type culture collection

ECACC: European collection of cell cultures

MFI: Mean fluorescence intensities.

FIG. 15 provides data about ADCC with MM-samples:

a: 2-4 individual analyses

FIG. 16 provides the experimental results of mean tumor volumes after treatment of human myeloma xenograft with MOR03080: group 1: vehicle; group 2: MOR03080 as hIgG1 1 mg/kg 32-68 days every second day; group 3: MOR03080 as hIgG1 5 mg/kg 32-68 days every second day; group 4: MOR03080 as chIgG2a 5 mg/kg 32-68 days every second day; group 5: MOR03080 as hIgG1 1 mg/kg, 14-36 days every second day; group 6: untreated.

FIG. 17 provides FACS analysis of cross-reactivity of anti-CD38 antibodies with different animal species.

FIG. 18 provides CD38 cross-linking with Raji cells.

FIG. 19: CDC assay with hCD38 CHO transfectants

CHO cells stably transfected with hCD38 were incubated with MOR03079 hIgG1, chimeric OKT10 (chOKT10) or an irrelevant HuCAL® IgG1 as negative control in the presence of human serum (source of complement). The negative control is represented by the highest antibody concentration used. Error bars represent the standard deviation based on three individual measurements for each antibody concentration. $EC_{50}$ values were calculated appropriately.

FIG. 20: ADCC assay with primary multiple myeloma samples

Human PBMCs (Effectors) and cells from the bone marrow aspirates of several MM-patients (MM-sample #6,7,10, 11,12,14) were mixed at an E:T-ratio of 30:1. Serial dilutions were applied for the human IgG1 MAbs (MOR03077, MOR03079, MOR03080) or the chimeric OKT10 (chOKT10) whereas the irrelevant negative control antibody (HuCAL® MAb, NC) antibody as well as MOR03079

(MM#10 and #11) is represented by the highest antibody concentration used. Error bars represent standard deviations based on three individual measurements for each antibody concentration. Sample MM#14 was derived from a plasma cell leukemia patient.

DETAILED DESCRIPTION OF THE INVENTION

The present invention is based on the discovery of novel methods of using antibodies that are specific to or have a high affinity for CD38 and can deliver a therapeutic benefit to a subject. The antibodies, which may be human or humanized, can be used in many contexts, which are more fully described herein. Suitable antibodies for use in the present invention are disclosed in U.S. 60/614,471, which hereby is incorporated by reference.

A "human" antibody or functional human antibody fragment is hereby defined as one that is not chimeric (e.g., not "humanized") and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment, is one that is encoded by a nucleic acid isolated from a library of antibody sequences of human origin (i.e., such library being based on antibodies taken from a human natural source).

A "humanized antibody" or functional humanized antibody fragment is defined herein as one that is (i) derived from a non-human source (e.g., a transgenic mouse which bears a heterologous immune system), which antibody is based on a human germline sequence; or (ii) chimeric, wherein the variable domain is derived from a non-human origin and the constant domain is derived from a human origin or (iii) CDR-grafted, wherein the CDRs of the variable domain are from a non-human origin, while one or more frameworks of the variable domain are of human origin and the constant domain (if any) is of human origin.

As used herein, an antibody "binds specifically to," is "specific to/for" or "specifically recognizes" an antigen (here, CD38) if such antibody is able to discriminate between such antigen and one or more reference antigen(s), since binding specificity is not an absolute, but a relative property. In its most general form (and when no defined reference is mentioned), "specific binding" is referring to the ability of the antibody to discriminate between the antigen of interest and an unrelated antigen, as determined, for example, in accordance with one of the following methods. Such methods comprise, but are not limited to Western blots, ELISA-, RIA-, ECL-, IRMA-tests, FACS, IHC and peptide scans. For example, a standard ELISA assay can be carried out. The scoring may be carried out by standard color development (e.g. secondary antibody with horseradish peroxide and tetramethyl benzidine with hydrogenperoxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like. It is possible for an antibody to be "specific to" or "specific for" an antigen of 2 or more cells/tissues and/or 2 or more species, provided that the antibody meets binding criteria for each of such cells/tissues and species, for example. Accordingly, an antibody may bind specifically to the target antigen CD38 on various cell types and/or tissues, e.g. erythrocytes, lymphocytes isolated from peripheral blood, spleen or lymph-nodes. In addition, an antibody may be specific to both CD38 of one species and CD38 of another species.

"Specific binding" also may refer to the ability of an antibody to discriminate between the target antigen and one or more closely related antigen(s), which are used as reference points, e.g. between CD38 and CD157. Additionally, "specific binding" may relate to the ability of an antibody to discriminate between different parts of its target antigen, e.g. different domains or regions of CD38, such as epitopes in the N-terminal or in the C-terminal region of CD38, or between one or more key amino acid residues or stretches of amino acid residues of CD38.

Also, as used herein, an "immunoglobulin" (Ig) hereby is defined as a protein belonging to the class IgG, IgM, IgE, IgA, or IgD (or any subclass thereof), and includes all conventionally known antibodies and functional fragments thereof. A "functional fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hypervariable region(s) of an antibody, i.e., the CDR-1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320). A preferred class of immunoglobulins for use in the present invention is IgG. "Functional fragments" of the invention include the domain of a $F(ab')_2$ fragment, a Fab fragment and scFv. The $F(ab')_2$ or Fab may be engineered to minimize or completely remove the intermolecular disulphide interactions that occur between the $C_{HI}$ and $C_L$ domains.

An antibody for use in the invention may be derived from a recombinant antibody library that is based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silica-created sequences are described, for example, in Knappik et al., J. Mol. Biol. (2000) 296:57; Krebs et al., J. Immunol. Methods. (2001) 254:67; and U.S. Pat. No. 6,300,064 issued to Knappik et al., which hereby are incorporated by reference in their entirety.

Antibodies for Use in the Invention

Throughout this document, reference is made to the following representative antibodies for use in the invention: "antibody nos." or "LACS" or "MOR" 3077 or 03077 (MAb#1), 3079 or 03079 (MAb#2), 3080 or 03080 (MAb#3) and 3100 or 03100 (MAb#4). LAC 3077 represents an antibody having a variable heavy region corresponding to SEQ ID NO: 1 (DNA)/SEQ ID NO: 5 (protein) and a variable light region corresponding to SEQ ID NO: 9 (DNA)/SEQ ID NO:

13 (protein). LAC 3079 represents an antibody having a variable heavy region corresponding to SEQ ID NO: 2 (DNA)/SEQ ID NO: 6 (protein) and a variable light region corresponding to SEQ ID NO: 10 (DNA)/SEQ ID NO: 14 (protein). LAC 3080 represents an antibody having a variable heavy region corresponding to SEQ ID NO: 3 (DNA)/SEQ ID NO: 7 (protein) and a variable light region corresponding to SEQ ID NO: 11 (DNA)/SEQ ID NO: 15 (protein). LAC 3100 represents an antibody having a variable heavy region corresponding to SEQ ID NO: 4 (DNA)/SEQ ID NO: 8 (protein) and a variable light region corresponding to SEQ ID NO: 12 (DNA)/SEQ ID NO: 16 (protein).

In one aspect, the invention provides methods for using antibodies having an antigen-binding region that can bind specifically to or has a high affinity for one or more regions of CD38, whose amino acid sequence is depicted by SEQ ID NO: 22. An antibody is said to have a "high affinity" for an antigen if the affinity measurement is at least 100 nM (monovalent affinity of Fab fragment). An antibody or antigen-binding region for use in the present invention preferably can bind to CD38 with an affinity of about less than 100 nM, more preferably less than about 60 nM, and still more preferably less than about 30 nM. Further preferred are uses of antibodies that bind to CD38 with an affinity of less than about 10 nM, and more preferably less than 3 about nM. For instance, the affinity of an antibody for use in the invention against CD38 may be about 10.0 nM or 2.4 nM (monovalent affinity of Fab fragment).

Specificity

The four representative antibodies were tested as human IgG1 and human-mouse chimeric IgG2a (except for MOR03100) on a panel of different antigens including two hCD38 Fc fusion (aa 45-300 & aa 45-273), BSA and lysozyme. All hCD38-specific antibodies recognized only the "full-length" hCD38 Fc-fusion protein (aa 45-300) (FIG. 12), when tested with such full-length protein and a format having a C-terminally deleted format, most likely due to misfolding and loss of antigenic sites Table 1 provides a summary of affinities of representative antibodies, as determined by surface plasmon resonance (Biacore) and FACS Scatchard analysis:

TABLE 1

Antibody Affinities

| Antibody (Fab or IgG1) | BIACORE (Fab) $K_D$ [nM][a] | FACS Scatchard (IgG1)[b] $K_D$ [nM][a] |
|---|---|---|
| MOR03077 | 56.0 | 0.89 |
| MOR03079 | 2.4 | 0.60 |
| MOR03080 | 27.5 | 0.47 |
| MOR03100 | 10.0 | 6.31 |
| Chimeric OKT10 | not determined | 8.28 |

[a]mean from at least 2 different affinity determinations
[b]RPMI8226 MM cell-line used for FACS-Scatchards With reference to Table 1, the affinity of LACs 3077, 3079, 3080 and 3100 was measured by surface plasmon resonance (Biacore) on immobilized recombinant CD38 and by a flow cytometry procedure utilizing the CD38-expressing human RPMI8226 cell line. The Biacore studies were performed on directly immobilized antigen (CD38-Fc fusion protein). The Fab format of LACs 3077, 3079, 3080 and 3100 exhibit an monovalent affinity range between about 2.4 and 56 nM on immobilized CD38-Fc fusion protein with LAC 3079 showing the highest affinity, followed by Fabs 3100, 3080 and 3077.

The IgG1 format was used for the cell-based affinity determination (FACS Scatchard). The right column of Table 1 denotes the binding strength of the LACS in this format. LAC 3080 showed the strongest binding, which is slightly stronger than LACS 3079 and 3077.

Another preferred feature of preferred antibodies for use in the invention is their specificity for an area within the N-terminal region of CD38. For example, LACs 3077, 3079, 3080, and 3100 of the invention can bind specifically to the N-terminal region of CD38.

The type of epitope to which an antibody for use in the invention binds may be linear (i.e. one consecutive stretch of amino acids) or conformational (i.e. multiple stretches of amino acids). In order to determine whether the epitope of a particular antibody is linear or conformational, the skilled worker can analyze the binding of antibodies to overlapping peptides (e.g., 13-mer peptides with an overlap of 11 amino acids) covering different domains of CD38. LACS 3077, 3080, and 3100 recognize discontinuous epitopes in the N-terminal region of CD38, whereas the epitope of LAC 3079 can be described as linear (see FIG. 7). Combined with the knowledge provided herein, the skilled worker in the art will know how to use one or more isolated epitopes of CD38 for generating antibodies having an antigen-binding region that is specific for said epitopes (e.g. using synthetic peptides of epitopes of CD38 or cells expressing epitopes of CD38).

An antibody for use in the invention preferably is species cross-reactive with humans and at least one other non-human species. The non-human species can be non-human primate, e.g. rhesus, baboon and/or cynomolgus. Other non-human species can be minipig, rabbit, mouse, rat and/or hamster. An antibody that is cross reactive with at least one other species beside human can provide greater flexibility and benefits over known anti-CD38 antibodies, for purposes of conducting in vivo studies in multiple species with the same antibody. An antibody that is cross reactive with minipig and/or rabbit, for example, can be a candidate for toxicology and safety studies.

Preferably, an antibody for use in the invention not only is able to bind to CD38, but also is able to mediate killing of a cell expressing CD38. More specifically, an antibody for use in the invention can mediate its therapeutic effect by depleting CD38-positive (e.g., malignant) cells via antibody-effector functions. These functions include antibody-dependent cellular cytotoxicity (ADCC) and complement-dependent cytotoxicity (CDC).

Table 2 provides a summary of the determination of EC50 values of representative antibodies of the invention in both ADCC and CDC:

TABLE 2

EC50 Values of Antibodies

| Antibody | ADCC EC50 [nM] | | CDC EC50 [nM] |
|---|---|---|---|
| (IgG1) | LP-1 | RPMI8226 | CHO-transfectants |
| MOR03077 | 0.60a | 0.08a | 0.8c; 0.94d |
| MOR03079 | 0.09[a] | 0.04[a] | 0.41[c] |
| MOR03080 | 0.17[b] | 0.05[a] | 3.2[c]; 2.93[d] |
| MOR03100 | 1.00[b] | 0.28[a] | 10.9[c]; 13.61[e] |
| Chimeric OKT10 | 5.23[a] | 4.10[a] | 9.30[c] |

[a]mean from at least 2 EC50 determinations
[b]single determination
[c]mean from 2 EC50 determinations
[d]mean from 3 EC50 determinations
[e]mean from 4 EC50 determinations CD38-expression, however, is not only found on immune cells within the myeloid (e.g. monocytes, granulocytes) and lymphoid lineage (e.g. activated B and T-cells; plasma cells), but also on the respective precursor cells. Since it is important that those cells are not affected by antibody-mediated killing of malignant cells, the antibodies of the present invention are preferably not cytotoxic to precursor cells.

In addition to its catalytic activities as a cyclic ADP-ribose cyclase and hydrolase, CD38 displays the ability to transduce signals of biological relevance (Hoshino et al., 1997; Ausiello et al., 2000). Those functions can be induced in vivo by, e.g. receptor-ligand interactions or by cross-linking with agonistic anti-CD38 antibodies, leading, e.g. to calcium mobilization, lymphocyte proliferation and release of cytokines. Preferably, the antibodies of the present invention are non-agonistic antibodies.

Peptide Variants

Antibodies for use in the invention are not limited to the specific peptide sequences provided herein. Rather, the invention also embodies the use of variants of these polypeptides. With reference to the instant disclosure and conventionally available technologies and references, the skilled worker will be able to prepare, test and utilize functional variants of the antibodies disclosed herein, while appreciating that variants having the ability to mediate killing of a CD38+ target cell fall within the scope of the present invention. As used in this context, "ability to mediate killing of a CD38+ target cell" means a functional characteristic ascribed to an anti-CD38 antibody for use in the invention. Ability to mediate killing of a CD38+ target cell, thus, includes the ability to mediate killing of a CD38+ target cell, e.g. by ADCC and/or CDC, or by toxin constructs conjugated to an antibody for use in the invention.

A variant can include, for example, an antibody that has at least one altered complementarity determining region (CDR) (hyper-variable) and/or framework (FR) (variable) domain/position, vis-à-vis a peptide sequence disclosed herein. To better illustrate this concept, a brief description of antibody structure follows.

An antibody is composed of two peptide chains, each containing one (light chain) or three (heavy chain) constant domains and a variable region (VL, VH), the latter of which is in each case made up of four FR regions and three interspaced CDRs. The antigen-binding site is formed by one or more CDRs, yet the FR regions provide the structural framework for the CDRs and, hence, play an important role in antigen binding. By altering one or more amino acid residues in a CDR or FR region, the skilled worker routinely can generate mutated or diversified antibody sequences, which can be screened against the antigen, for new or improved properties, for example.

Tables 3a (VH) and 3b (VL) delineate the CDR and FR regions for certain antibodies for use in the invention and compare amino acids at a given position to each other and to corresponding consensus or "master gene" sequences (as described in U.S. Pat. No. 6,300,064):

TABLE 3a

VH Sequences

VH sequences CD 38 binders

| | VH | Framework 1 | | | | | | | | | | | | | | | | CDR 1 | | | | | | | | | | | | Framework 2 | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | 1 | | | | | | | | | | 2 | | | | | | | | | | 3 | | | | | | | | | | | | 4 | | | | | | | | | |
| | Position | 0 | 1 | 2 | 3 | 4 | 5 | 6 | 7 | 8 | 9 | 0 | 1 | 2 | 3 | 4 | 5 | 6 | 7 | 8 | 9 | 0 | 1 | a | b | 2 | 3 | 4 | 5 | 6 | 7 | 8 | 9 | 0 | 1 | 2 | 3 | 4 | 5 | 6 | 7 | 8 | 9 |
| | | | | | | | | | | | | | | | | | | BspEl | | | | | | | | | | | | | | | | | BstXl | | | | | Xhol | | | |
| SEQ ID NO 17 | VH1B | E | V | K | K | P | G | A | S | V | K | V | S | C | K | A | S | G | Y | T | F | T | S | - | - | Y | Y | M | H | W | V | R | Q | A | P | G | Q | G | L | E | W | M | G |
| SEQ ID NO 5 | 3077 | E | V | K | K | P | G | A | S | V | K | V | S | C | K | A | S | G | Y | T | F | T | S | | | Y | S | I | N | W | V | R | Q | A | P | G | Q | G | L | E | W | M | G |
| SEQ ID NO 18 | VH3 | G | L | V | Q | P | G | G | S | L | R | L | S | C | A | A | S | G | F | T | F | S | S | - | - | Y | A | M | S | W | V | R | Q | A | P | G | K | G | L | E | W | V | S |
| SEQ ID NO 6 | 3079 | G | L | V | Q | P | G | G | S | L | R | L | S | C | A | A | S | G | F | T | F | S | N | | | Y | G | M | H | W | V | R | Q | A | P | G | K | G | L | E | W | V | S |
| SEQ ID NO 7 | 3080 | G | L | V | Q | P | G | G | S | L | R | L | S | C | A | A | S | G | F | T | F | S | S | | | Y | G | M | H | W | V | R | Q | A | P | G | K | G | L | E | W | V | S |
| SEQ ID NO 8 | 3100 | G | L | V | Q | P | G | G | S | L | R | L | S | C | A | A | S | G | F | T | F | S | S | | | N | G | M | S | W | V | R | Q | A | P | G | K | G | L | E | W | V | S |

| | | CDR 2 | | | | | | | | | | | | | | | | | | | | | | Framework 3 | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | 5 | | | | | | | | | | | | | 6 | | | | | | | | | | 7 | | | | | | | | | | 8 | | | | | | | | |
| | Position | 0 | 1 | 2 | a | b | c | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | a | b | c | 3 | 4 | 5 |
| | | | | | | | | | | | | | | | | | | | | | | | BstEl | | | | | | | | | | | | | | | | | | | | |
| SEQ ID NO 17 | VH1B | W | I | N | P | - | - | N | S | G | G | T | N | Y | A | Q | K | F | Q | G | R | V | T | M | T | R | D | T | S | I | S | T | A | Y | M | E | L | S | S | L | R | S | E |
| SEQ ID NO 5 | 3077 | Y | I | D | P | | | N | R | G | N | T | N | Y | A | Q | K | F | Q | G | R | V | T | M | T | R | D | T | S | I | S | T | A | Y | M | E | L | S | S | L | R | S | E |
| SEQ ID NO 18 | VH3 | A | I | S | G | - | - | S | G | G | S | T | Y | Y | A | D | S | V | K | G | R | F | T | I | S | R | D | N | S | K | N | T | L | Y | L | Q | M | N | S | L | R | A | E |
| SEQ ID NO 6 | 3079 | N | I | R | S | | | D | G | S | W | T | Y | Y | A | D | S | V | K | G | R | F | T | I | S | R | D | N | S | K | N | T | L | Y | L | Q | M | N | S | L | R | A | E |
| SEQ ID NO 7 | 3080 | N | I | Y | S | | | D | G | S | N | T | F | Y | A | D | S | V | K | G | R | F | T | I | S | R | D | N | S | K | N | T | L | Y | L | Q | M | N | S | L | R | A | E |
| SEQ ID NO 8 | 3100 | N | I | S | Y | | | L | S | S | S | T | Y | Y | A | D | S | V | K | G | R | F | T | I | S | R | D | N | S | K | N | T | L | Y | L | Q | M | N | S | L | R | A | E |

TABLE 3a-continued

VH Sequences

| | | Framework 3 | CDR 3 | Framework 4 |
|---|---|---|---|---|
| | Position | 6 7 8 9 9 0 1 2 3 4 5 6 7 8 9 | 10 0 a b c d e f g h i j 1 2 | 3 4 5 6 7 8 9 11 0 1 2 3 |
| | | Eagl BssHll | | Styl Blpl |
| SEQ ID NO 17 | VH1B | D T A V Y Y C A R | W G G D G F Y A - - - - - - - M D Y | W G Q G T L V T V S S |
| SEQ ID NO 5 | 3077 | D T A V Y Y C A R | E Y I Y F I H G M - - - - - - L D F | W G Q G T L V T V S S |
| SEQ ID NO 18 | VH3 | D T A V Y Y C A R | W G G D G F Y A - - - - - - - M D Y | W G Q G T L V T V S S |
| SEQ ID NO 6 | 3079 | D T A V Y Y C A R | R Y W S K S H A S V - - - - - T D Y | W G Q G T L V T V S S |
| SEQ ID NO 7 | 3080 | D T A V Y Y C A R | N M Y R W P F H Y F - - - - - F D Y | W G Q G T L V T V S S |
| SEQ ID NO 8 | 3100 | D T A V Y Y C A R | F Y G Y F N Y - - - - - - - - A D V | W G Q G T L V T V S S |

TABLE 3b

VL Sequences

VL sequences CD 38 binders

| | VL | Framework 1 | CDR 1 |
|---|---|---|---|
| | Position | 1 2 3 4 5 6 7 8 9 1 0 1 2 3 4 5 6 7 8 9 2 0 1 2 3 | 4 5 6 7 8 9 3 0 a b c d e f 1 2 3 4 |
| | | EccRY SecAl EssSl | |
| SEQ ID NO 19 | VLλ3 | S Y E L T Q P P - S V S V A P G G T A R I S C | S G D A L G D - - - - - - K Y A S |
| SEQ ID NO 15 | 3080 | D I E L T Q P P - S V S V A P G G T A R I S C | S G D N I G N - - - - - - K Y V S |
| SEQ ID NO 16 | 3100 | D I E L T Q P P - S V S V A P G G T A R I S C | S G D N I G H - - - - - - Y Y A S |
| | | 1 1 | 1 1 1 1 |
| SEQ ID NO 20 | VLκ1 | D I Q M T Q S P S S L S A S V G C F Y T I T C | R A S Q G I S - - - - - - S Y L A |
| SEQ ID NO 14 | 3079 | D I Q M T Q S P S S L S A S Y G C F Y T I T C | R A S Q D I S - - - - - - A F L N |
| | | | 1 1 1 1 |
| SEQ ID NO 21 | VLκ2 | D I V M T Q S P L S L P V T P G E P A S I S C | R S S Q S L L H S - N G Y N Y L D |
| SEQ ID NO 13 | 3077 | D I V M T Q S P L S L P V T P G E P A S I S C | R S S Q S L L F I - D G N N Y L N |
| | | | 1 1 1 1 1 |

| | | Framework 2 | CDR 2 | Framework 3 |
|---|---|---|---|---|
| | Position | 5 6 7 8 9 4 0 1 2 3 4 5 6 7 8 9 | 5 0 1 2 3 4 5 6 | 7 8 9 6 0 1 2 3 4 5 6 7 8 9 7 0 1 2 3 4 |
| | | Kpnl Xnal Bbel | Bsu361 | BanHl |
| SEQ ID NO 19 | VLλ3 | W Y Q Q K P G Q A P V L V I Y | D D S D R P S | G I P E R F S G S N S G N T A T L T |
| SEQ ID NO 15 | 3080 | W Y Q Q K P G Q A P V V V I Y | G D N N R P S | G I P E R F S G S N S G N T A T L T |
| SEQ ID NO 16 | 3100 | W Y Q Q K P G Q A P V L V I Y | R D N D R P S | G I P E R F S G S N S G N T A T L T |
| | | | 1 | |
| SEQ ID NO 20 | VLκ1 | W Y Q Q K P G K A P K L L I Y | A A S S - Q S | G V P S R F S G S G S G T D F T L T |
| SEQ ID NO 14 | 3079 | W Y Q Q K P G K A P K L L I Y | K V S N - Q S | G Y P S R F S G S G S G T D F T L T |
| | | | 1 1 | |
| SEQ ID NO 21 | VLκ2 | W Y L Q K P G Q S P Q L L I Y | L G S N R A S | G V P D R F S G S G S G T D F T L K |
| SEQ ID NO 13 | 3077 | W Y L Q K P G Q S P Q L L I Y | L G S N R A S | G V P D R F S G S G S G T D F T L K |

TABLE 3b-continued

VL Sequences

| | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|
| | | Framework 3 | | | | | | | | | | | | | | | CDR 3 | | | | | | | | Framework 4 | | | | | | | | | | | | | |
| | | | | | | | 8 | | | | | | | | | | 9 | | | | | | | | | | | | 10 | | | | | | | | | |
| | Position | 5 | 6 | 7 | 8 | 9 | 0 | 1 | 2 | 3 | 4 | 5 | 6 | 7 | 8 | 9 | 0 | 1 | 2 | 3 | 4 | 5 | a | b | 6 | 7 | 8 | 9 | 0 | 1 | 2 | 3 | 4 | 5 | 6 | 7 | 8 | 9 |
| | | | | | | | | BbsI | | | | | | | | | | | | | | | | | | | | | | | | | HpaI | | | | MscI | |
| SEQ ID NO 19 | VLλ3 | I | S | G | T | Q | A | E | D | E | A | D | Y | Y | C | Q | Q | H | Y | T | T | P | - | - | P | V | F | G | G | G | T | K | L | T | V | L | G | |
| SEQ ID NO 15 | 3080 | I | S | G | T | Q | A | E | D | E | A | D | Y | Y | C | S | S | Y | D | S | S | Y | - | - | F | V | F | G | G | G | T | K | L | T | V | L | G | Q |
| SEQ ID NO 16 | 3100 | I | S | G | T | Q | A | E | D | E | A | D | Y | Y | C | Q | S | Y | D | Y | L | H | D | - | F | V | F | G | G | G | T | K | L | T | V | L | G | Q |
| | | | | | | | | | | | | | | | | | 1 | 1 | 1 | 1 | 1 | 1 | 1 | | 1 | | | | | | | | | | | | | 1 |
| SEQ ID NO 20 | VLκ1 | I | S | S | L | Q | P | E | D | F | A | T | Y | Y | C | Q | Q | H | Y | T | T | P | - | - | P | T | F | G | Q | G | T | K | V | E | I | K | R | |
| SEQ ID NO 14 | 3079 | I | S | S | L | Q | P | E | D | F | A | T | Y | Y | C | Q | Q | A | Y | S | G | S | | | I | T | F | G | Q | G | T | K | V | E | I | K | R | T |
| | | | | | | | | | | | | | | | | | | 1 | | 1 | 1 | 1 | 1 | 1 | 1 | | | | | | | | | | | | | 1 |
| SEQ ID NO 21 | VLκ2 | I | S | R | V | E | A | E | D | V | G | V | Y | Y | C | Q | Q | H | Y | T | T | P | - | - | P | T | F | G | Q | G | T | K | L | E | I | K | R | |
| SEQ ID NO 13 | 3077 | I | S | R | V | E | A | E | D | V | G | V | Y | Y | C | Q | Q | Y | S | S | K | S | | | A | T | F | G | Q | G | T | K | V | E | I | K | R | T |
| | | | | | | | | | | | | | | | | | | 1 | 1 | 1 | 1 | 1 | 1 | 1 | 1 | | | | | | | | 1 | | | | | 1 |

The skilled worker can use the data in Tables 3a and 3b to design peptide variants, the use of which is within the scope of the present invention. It is preferred that variants are constructed by changing amino acids within one or more CDR regions; a variant might also have one or more altered framework regions. With reference to a comparison of the antibodies to each other, candidate residues that can be changed include e.g. residues 4 or 37 of the variable light and e.g. residues 13 or 43 of the variable heavy chains of LACs 3080 and 3077, since these are positions of variance vis-à-vis each other. Alterations also may be made in the framework regions. For example, a peptide FR domain might be altered where there is a deviation in a residue compared to a germline sequence.

With reference to a comparison of the antibodies to the corresponding consensus or "master gene" sequence, candidate residues that can be changed include e.g. residues 27, 50 or 90 of the variable light chain of LAC 3080 compared to VLλ3 and e.g. residues 33, 52 and 97 of the variable heavy chain of LAC 3080 compared to VH3. Alternatively, the skilled worker could make the same analysis by comparing the amino acid sequences disclosed herein to known sequences of the same class of such antibodies, using, for example, the procedure described by Knappik et al., 2000 and U.S. Pat. No. 6,300,064 issued to Knappik et al.

Furthermore, variants may be obtained by using one LAC as starting point for optimization by diversifying one or more amino acid residues in the LAC, preferably amino acid residues in one or more CDRs, and by screening the resulting collection of antibody variants for variants with improved properties. Particularly preferred is diversification of one or more amino acid residues in CDR-3 of VL, CDR-3 of VH, CDR-1 of VL and/or CDR-2 of VH. Diversification can be done by synthesizing a collection of DNA molecules using trinucleotide mutagenesis (TRIM) technology (Virnekäs, B., Ge, L., Plückthun, A., Schneider, K. C., Wellnhofer, G., and Moroney S. E. (1994) Trinucleotide phosphoramidites: ideal reagents for the synthesis of mixed oligonucleotides for random mutagenesis. Nucl. Acids Res. 22, 5600.).

Conservative Amino Acid Variants

Polypeptide variants may be made that conserve the overall molecular structure of an antibody peptide sequence described herein. Given the properties of the individual amino acids, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved.

For example, (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants. In one particular example, amino acid position 3 in SEQ ID NOS: 5, 6, 7, and/or 8 can be changed from a Q to an E.

As used herein, "sequence identity" between two polypeptide sequences indicates the percentage of amino acids that are identical between the sequences. "Sequence similarity" indicates the percentage of amino acids that either are identical or that represent conservative amino acid substitutions. Preferred polypeptide sequences of the invention have a sequence identity in the CDR regions of at least 60%, more preferably, at least 70% or 80%, still more preferably at least 90% and most preferably at least 95%. Preferred antibodies also have a sequence similarity in the CDR regions of at least 80%, more preferably 90% and most preferably 95%.

DNA Molecules of the Invention

The present invention also relates to uses of DNA molecules that encode an antibody for use in the invention. These sequences include, but are not limited to, those DNA molecules set forth in FIGS. 1*a* and 2*a*.

DNA molecules of the invention are not limited to the sequences disclosed herein, but also include variants thereof. DNA variants within the invention may be described by reference to their physical properties in hybridization. The skilled worker will recognize that DNA can be used to identify its complement and, since DNA is double stranded, its equivalent or homolog, using nucleic acid hybridization techniques. It also will be recognized that hybridization can occur with less than 100% complementarity. However, given appropriate choice of conditions, hybridization techniques can be used to differentiate among DNA sequences based on their structural relatedness to a particular probe. For guidance regarding such conditions see, Sambrook et al., 1989 (Sambrook, J., Fritsch, E. F. and Maniatis, T. (1989) Molecular Cloning: A laboratory manual, Cold Spring Harbor Laboratory Press, Cold Spring Harbor, USA) and Ausubel et al., 1995 (Ausubel, F. M., Brent, R., Kingston, R. E., Moore, D. D., Sedman, J. G., Smith, J. A., & Struhl, K. eds. (1995). Current Protocols in Molecular Biology. New York: John Wiley and Sons).

Structural similarity between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules' displaying a lesser degree of structural relatedness. Hybridization stringency, therefore, directly correlates with the structural relationships of two nucleic acid sequences. The following relationships are useful in correlating hybridization and relatedness (where $T_m$ is the melting temperature of a nucleic acid duplex):

a. $T_m=69.3+0.41(G+C)\%$
b. The $T_m$ of a duplex DNA decreases by 1° C. with every increase of 1% in the number of mismatched base pairs.
c. $(T_m)_{\mu 2}-(T_m)_{\mu 1}=18.5\ \log_{10}\mu 2/\mu 1$ where μ1 and μ2 are the ionic strengths of two solutions.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding. Hybridization typically is performed in two phases: the "binding" phase and the "washing" phase.

First, in the binding phase, the probe is bound to the target under conditions favoring hybridization. Stringency is usually controlled at this stage by altering the temperature. For high stringency, the temperature is usually between 65° C. and 70° C., unless short (<20 nt) oligonucleotide probes are used. A representative hybridization solution comprises 6×SSC, 0.5% SDS, 5× Denhardt's solution and 100 μg of nonspecific carrier DNA. See Ausubel et al., section 2.9, supplement 27 (1994). Of course, many different, yet functionally equivalent, buffer conditions are known. Where the degree of relatedness is lower, a lower temperature may be chosen. Low stringency binding temperatures are between about 25° C. and 40° C. Medium stringency is between at least about 40° C. to less than about 65° C. High stringency is at least about 65° C.

Second, the excess probe is removed by washing. It is at this phase that more stringent conditions usually are applied. Hence, it is this "washing" stage that is most important in determining relatedness via hybridization. Washing solutions typically contain lower salt concentrations. One exemplary medium stringency solution contains 2×SSC and 0.1% SDS. A high stringency wash solution contains the equivalent (in ionic strength) of less than about 0.2×SSC, with a preferred stringent solution containing about 0.1×SSC. The temperatures associated with various stringencies are the same as discussed above for "binding." The washing solution also typically is replaced a number of times during washing. For example, typical high stringency washing conditions comprise washing twice for 30 minutes at 55° C. and three times for 15 minutes at 60° C.

Accordingly, the present invention includes the use of nucleic acid molecules that hybridize to the molecules of set forth in FIGS. 1*a* and 2*a* under high stringency binding and washing conditions, where such nucleic molecules encode an antibody or functional fragment thereof for uses as described herein. Preferred molecules (from an mRNA perspective) are those that have at least 75% or 80% (preferably at least 85%, more preferably at least 90% and most preferably at least 95%) homology or sequence identity with one of the DNA molecules described herein. In one particular example of a variant of the invention, nucleic acid position 7 in SEQ ID NOS: 1, 2, 3 and/or 4 can be substituted from a C to a G; thereby changing the codon from CAA to GAA.

Functionally Equivalent Variants

Yet another class of DNA variants the use of which is within the scope of the invention may be described with reference to the product they encode (see the peptides listed in FIGS. 1*b* and 2*b*). These functionally equivalent genes are characterized by the fact that they encode the same peptide sequences found in FIGS. 1*b* and 2*b* due to the degeneracy of the genetic code. SEQ ID NOS: 1 and 31 are an example of functionally equivalent variants, as their nucleic acid sequences are different, yet they encode the same polypeptide, i.e. SEQ ID NO: 5.

It is recognized that variants of DNA molecules provided herein can be constructed in several different ways. For example, they may be constructed as completely synthetic DNAs. Methods of efficiently synthesizing oligonucleotides in the range of 20 to about 150 nucleotides are widely available. See Ausubel et al., section 2.11, Supplement 21 (1993). Overlapping oligonucleotides may be synthesized and assembled in a fashion first reported by Khorana et al., J. Mol. Biol. 72:209-217 (1971); see also Ausubel et al., supra, Section 8.2. Synthetic DNAs preferably are designed with convenient restriction sites engineered at the 5' and 3' ends of the gene to facilitate cloning into an appropriate vector.

As indicated, a method of generating variants is to start with one of the DNAs disclosed herein and then to conduct site-directed mutagenesis. See Ausubel et al., supra, chapter 8, Supplement 37 (1997). In a typical method, a target DNA is cloned into a single-stranded DNA bacteriophage vehicle. Single-stranded DNA is isolated and hybridized with an oligonucleotide containing the desired nucleotide alteration(s). The complementary strand is synthesized and the double stranded phage is introduced into a host. Some of the resulting progeny will contain the desired mutant, which can be confirmed using DNA sequencing. In addition, various methods are available that increase the probability that the progeny phage will be the desired mutant. These methods are well known to those in the field and kits are commercially available for generating such mutants.

Recombinant DNA Constructs and Expression

The present invention further provides for the use of recombinant DNA constructs comprising one or more of the nucleotide sequences of the present invention. The recombinant constructs are used in connection with a vector, such as a plasmid or viral vector, into which a DNA molecule encoding an antibody for use in the invention is inserted.

The encoded gene may be produced by techniques described in Sambrook et al , 1989, and Ausubel et al., 1989. Alternatively, the DNA sequences may be chemically synthesized using, for example, synthesizers. See, for example, the techniques described in OLIGONUCLEOTIDE SYNTHESIS (1984, Gait, ed., IRL Press, Oxford), which is incorporated by reference herein in its entirety. Recombinant constructs of the invention are comprised with expression vectors that are capable of expressing the RNA and/or protein products of the encoded DNA(s). The vector may further comprise regulatory sequences, including a promoter operably linked to the open reading frame (ORF). The vector may further comprise a selectable marker sequence. Specific initiation and bacterial secretory signals also may be required for efficient translation of inserted target gene coding sequences.

The present invention further provides for uses of host cells containing at least one of the DNAs disclosed herein. The host cell can be virtually any cell for which expression vectors are available. It may be, for example, a higher eukaryotic host cell, such as a mammalian cell, a lower eukaryotic host cell, such as a yeast cell, but preferably is a prokaryotic cell, such as a bacterial cell. Introduction of the recombinant construct into the host cell can be effected by calcium phosphate transfection, DEAE, dextran mediated transfection, electroporation or phage infection.

Bacterial Expression

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus.*

Bacterial vectors may be, for example, bacteriophage-, plasmid- or phagemid-based. These vectors can contain a selectable marker and bacterial origin of replication derived from commercially available plasmids typically containing elements of the well known cloning vector pBR322 (ATCC 37017). Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

In bacterial systems, a number of expression vectors may be advantageously selected depending upon the use intended for the protein being expressed. For example, when a large quantity of such a protein is to be produced, for the generation of antibodies or to screen peptide libraries, for example, vectors which direct the expression of high levels of fusion protein products that are readily purified may be desirable.

Therapeutic Methods

Therapeutic methods involve administering to a subject in need of treatment a therapeutically effective amount of an antibody contemplated by the invention. A "therapeutically effective" amount hereby is defined as the amount of an antibody that is of sufficient quantity to deplete CD38-positive cells in a treated area of a subject—either as a single dose or according to a multiple dose regimen, alone or in combination with other agents, which leads to the alleviation of an adverse condition, yet which amount is toxicologically tolerable. The subject may be a human or non-human animal (e.g., rabbit, rat, mouse, monkey or other lower-order primate).

An antibody for use in the invention might be co-administered with known medicaments, and in some instances the antibody might itself be modified. For example, an antibody could be conjugated to an immunotoxin or radioisotope to potentially further increase efficacy.

The antibodies can be used as a therapeutic or a diagnostic tool in a variety of situations where CD38 is undesirably expressed or found. For example, in an in vivo study treating human myeloma xenografts in mice, the anti-tumor efficacy of intraperitoneally applied antibodies (HuCAL® anti-CD38) to the vehicle treatment (PBS) was compared. The human antibody hMOR03080 (isotype IgG1) was tested in different amounts and treatment schedules and it is assumed that the human antibodies MOR03077 and MOR03079 would lead to similar results than the tested antibody MOR03080.

Disorders and conditions particularly suitable for treatment with an antibody are multiple myeloma (MM) and other haematological diseases, such as chronic lymphocytic leukemia (CLL), chronic myelogenous leukemia (CML), acute myelogenous leukemia (AML), and acute lymphocytic leukemia (ALL). An antibody also might be used to treat inflammatory disease such as rheumatoid arthritis (RA) or systemic lupus erythematosus (SLE).

To treat any of the foregoing disorders, pharmaceutical compositions for use in accordance with the present invention may be formulated in a conventional manner using one or more physiologically acceptable carriers or excipients. An antibody for use in the invention can be administered by any suitable means, which can vary, depending on the type of disorder being treated. Possible administration routes include parenteral (e.g., intramuscular, intravenous, intraarterial, intraperitoneal, or subcutaneous), intrapulmonary and intranasal, and, if desired for local immunosuppressive treatment, intralesional administration. In addition, an antibody for use in the invention might be administered by pulse infusion, with, e.g., declining doses of the antibody. Preferably, the dosing is given by injections, most preferably intravenous or subcutaneous injections, depending in part on whether the administration is brief or chronic. The amount to be administered will depend on a variety of factors such as the clinical symptoms, weight of the individual, whether other drugs are administered. The skilled artisan will recognize that the route of administration will vary depending on the disorder or condition to be treated.

Determining a therapeutically effective amount of the novel polypeptide, according to this invention, largely will depend on particular patient characteristics, route of administration, and the nature of the disorder being treated. General guidance can be found, for example, in the publications of the International Conference on Harmonisation and in REMINGTON'S PHARMACEUTICAL SCIENCES, chapters 27 and 28, pp. 484-528 (18th ed., Alfonso R. Gennaro, Ed., Easton, Pa.: Mack Pub. Co., 1990). More specifically, determining a therapeutically effective amount will depend on such factors as toxicity and efficacy of the medicament. Toxicity may be determined using methods well known in the art and found in the foregoing references. Efficacy may be determined utilizing the same guidance in conjunction with the methods described below in the Examples.

Diagnostic Methods

CD38 is highly expressed on hematological cells in certain malignancies; thus, an anti-CD38 antibody for use in the invention may be employed in order to image or visualize a site of possible accumulation of malignant cells in a patient. In this regard, an antibody can be detectably labeled, through the use of radioisotopes, affinity labels (such as biotin, avidin, etc.) fluorescent labels, paramagnetic atoms, etc. Procedures for accomplishing such labeling are well known to the art. Clinical application of antibodies in diagnostic imaging are reviewed by Grossman, H. B., Urol. Clin. North Amer. 13:465-474 (1986)), Unger, E. C. et al., Invest. Radiol. 20:693-700 (1985)), and Khaw, B. A. et al., Science 209:295-297 (1980)).

The detection of foci of such detectably labeled antibodies might be indicative of a site of tumor development, for example. In one embodiment, this examination is done by removing samples of tissue or blood and incubating such samples in the presence of the detectably labeled antibodies. In a preferred embodiment, this technique is done in a non-invasive manner through the use of magnetic imaging, fluorography, etc. Such a diagnostic test may be employed in monitoring the success of treatment of diseases, where presence or absence of CD38-positive cells is a relevant indicator. The invention also contemplates the use of an anti-CD38 antibody, as described herein for diagnostics in an ex vivo setting.

Therapeutic and Diagnostic Compositions

The antibodies for use in the present invention can be formulated according to known methods to prepare pharmaceutically useful compositions, wherein an antibody for use in the invention (including any functional fragment thereof) is combined in a mixture with a pharmaceutically acceptable carrier vehicle. Suitable vehicles and their formulation are described, for example, in REMINGTON'S PHARMACEUTICAL SCIENCES (18th ed., Alfonso R. Gennaro, Ed., Easton, Pa.: Mack Pub. Co., 1990). In order to form a pharmaceutically acceptable composition suitable for effective administration, such compositions will contain an effective amount of one or more of the antibodies for use in the present invention, together with a suitable amount of carrier vehicle.

Preparations may be suitably formulated to give controlled-release of the active compound. Controlled-release preparations may be achieved through the use of polymers to complex or absorb anti-CD38 antibody. The controlled delivery may be exercised by selecting appropriate macromolecules (for example polyesters, polyamino acids, polyvinyl, pyrrolidone, ethylenevinyl-acetate, methylcellulose, carboxymethylcellulose, or protamine, sulfate) and the concentration of macromolecules as well as the methods of incorporation in order to control release. Another possible method to control the duration of action by controlled release preparations is to incorporate anti-CD38 antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly (methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

The compounds may be formulated for parenteral administration by injection, e.g., by bolus injection or continuous infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration.

The invention further is understood by reference to the following working examples, which are intended to illustrate and, hence, not limit the invention.

EXAMPLES

Cell-Lines

The following cell-lines were obtained from the European Collection of Cell Cultures (ECACC), the German Collection of Microorganisms (DSMZ) or the American Type Culture collection (ATCC): hybridoma cell line producing the CD38 mouse IgG1 monoclonal antibody OKT10 (ECACC, #87021903), Jurkat cells (DSMZ, ACC282), LP-1 (DSMZ, ACC41), RPMI8226 (ATCC, CCL-155), HEK293 (ATCC, CRL-1573), CHO-K1 (ATCC, CRL-61) and Raji (ATCC, CCL-86)

Cells and Culture-Conditions

All cells were cultured under standardized conditions at 37° C. and 5% $CO_2$ in a humidified incubator. The cell-lines LP-1, RPMI8226, Jurkat and Raji were cultured in RPMI1640 (Pan biotech GmbH, #P04-16500) supplemented with 10% FCS (PAN biotech GmbH, #P30-3302), 50 U/ml penicillin, 50 μg/ml streptomycin (Gibco, #15140-122) and 2 mM glutamine (Gibco, #25030-024) and, in case of Jurkat- and Raji-cells, additionally 10 mM Hepes (Pan biotech GmbH, #P05-01100) and 1 mM sodium pyruvate (Pan biotech GmbH, #P04-43100) had to be added.

CHO-K1 and HEK293 were grown in DMEM (Gibco, #10938-025) supplemented with 2 mM glutamine and 10% FCS. Stable CD38 CHO-K1 transfectants were maintained in the presence of G418 (PAA GmbH, P11-012) whereas for HEK293 the addition of 1 mM sodium-pyruvate was essential. After transient transfection of HEK293 the 10% FCS was replaced by Ultra low IgG FCS (Invitrogen, #16250-078). The cell-line OKT10 was cultured in IDMEM (Gibco, #31980-022), supplemented with 2 mM glutamine and 20% FCS.

Preparation of Single Cell Suspensions from Peripheral Blood

All blood samples were taken after informed consent. Peripheral blood mononuclear cells (PBMC) were isolated by Histopaque®-1077 (Sigma) according to the manufacturer's instructions from healthy donors. Red blood cells were depleted from these cell suspensions by incubation in ACK Lysis Buffer (0.15 M NH4Cl, 10 mM $KHCO_3$, 0.1 M EDTA) for 5 min at RT or a commercial derivative (Bioscience,

#00-4333). Cells were washed twice with PBS and then further processed for flow cytometry or ADCC (see below).

Flow Cytometry ("FACS")

All stainings were performed in round bottom 96-well culture plates (Nalge Nunc) with $2\times10^5$ cells per well. Cells were incubated with Fab or IgG antibodies at the indicated concentrations in 50 μl FACS buffer (PBS, 3% FCS, 0.02% $NaN_3$) for 40 min at 4° C. Cells were washed twice and then incubated with R-Phycoerythrin (PE) conjugated goat-anti-human or goat-anti-mouse IgG (H+L) $F(ab')_2$ (Jackson Immuno Research), diluted 1:200 in FACS buffer, for 30 min at 4° C. Cells were again washed, resuspended in 0.3 ml FACS buffer and then analyzed by flow cytometry in a FACSCalibur (Becton Dickinson, San Diego, Calif.).

For FACS based Scatchard analyses RPMI8226 cells were stained with at 12 different dilutions (1:2ⁿ) starting at 12.5 μg/ml (IgG) final concentration. At least two independent measurements were used for each concentration and $K_D$ values extrapolated from median fluorescence intensities according to Chamow et al. (1994).

Surface Plasmon Resonance

The kinetic constants $k_{on}$ and $k_{off}$ were determined with serial dilutions of the respective Fab binding to covalently immobilized CD38-Fc fusion protein using the BIAcore 3000 instrument (Biacore, Uppsala, Sweden). For covalent antigen immobilization standard EDC-NHS amine coupling chemistry was used. For direct coupling of CD38 Fc-fusion protein CM5 senor chips (Biacore) were coated with ~600-700 RU in 10 mM acetate buffer, pH 4.5. For the reference flow cell a respective amount of HSA (human serum albumin) was used. Kinetic measurements were done in PBS (136 mM NaCl, 2.7 mM KCl, 10 mM $Na_2HPO_4$, 1.76 mM $KH_2PO_4$ pH 7.4) at a flow rate of 20 μl/min using Fab concentration range from 1.5-500 nM. Injection time for each concentration was 1 min, followed by 2 min dissociation phase. For regeneration 5 μl 10 mM HCl was used. All sensograms were fitted locally using BIA evaluation software 3.1 (Biacore).

Example 1

Antibody Generation from HuCAL® Libraries

For the generation of therapeutic antibodies against CD38, selections with the MorphoSys HuCAL GOLD® phage display library were carried out. HuCAL GOLD® is a Fab library based on the HuCAL® concept (Knappik et al., 2000; Krebs et al., 2001), in which all six CDRs are diversified, and which employs the CysDisplay™ technology for linking Fab fragments to the phage surface (Löhning, 2001).

A. Phagemid Rescue, Phage Amplification and Purification

HuCAL GOLD® phagemid library was amplified in 2× TY medium containing 34 μg/ml chloramphenicol and 1% glucose (2× TY-CG). After helper phage infection (VCSM13) at an OD600 of 0.5 (30 min at 37° C. without shaking; 30 min at 37° C. shaking at 250 rpm), cells were spun down (4120 g; 5 min; 4° C.), resuspended in 2× TY/34 μg/ml chloramphenicol/50 μg/ml kanamycin and grown overnight at 22° C. Phages were PEG-precipitated from the supernatant, resuspended in PBS/20% glycerol and stored at −80° C. Phage amplification between two panning rounds was conducted as follows: mid-log phase TG1 cells were infected with eluted phages and plated onto LB-agar supplemented with 1% of glucose and 34 μg/ml of chloramphenicol (LB-CG). After overnight incubation at 30° C., colonies were scraped off, adjusted to an OD600 of 0.5 and helper phage added as described above.

B. Pannings with HuCAL GOLD®

For the selections HuCAL GOLD® antibody-phages were divided into three pools corresponding to different VH master genes (pool 1: VH1/5λκ, pool 2: VH3 λκ, pool 3: VH2/4/6 λκ). These pools were individually subjected to 3 rounds of whole cell panning on CD38-expressing CHO-K1 cells followed by pH-elution and a post-adsorption step on CD38-negative CHO-K1-cells for depletion of irrelevant antibody-phages. Finally, the remaining antibody phages were used to infect *E. coli* TG1 cells. After centrifugation the bacterial pellet was resuspended in 2× TY medium, plated on agar plates and incubated overnight at 30° C. The selected clones were then scraped from the plates, phages were rescued and amplified. The second and the third round of selections were performed as the initial one.

The Fab encoding inserts of the selected HuCAL GOLD® phages were subcloned into the expression vector pMORPH®x9_Fab_FS (Rauchenberger et al., 2003) to facilitate rapid expression of soluble Fab. The DNA of the selected clones was digested with XbaI and EcoR1 thereby cutting out the Fab encoding insert (ompA-VLCL and phoA-Fd), and cloned into the XbaI/EcoRI cut vector pMORPH®x9_Fab_FS. Fab expressed in this vector carry two C-terminal tags (FLAG™ and Strep-tag® II) for detection and purification.

Example 2

Biological Assays

Antibody dependent cellular cytotoxicity (ADCC) and complement-dependent cytotoxicity was measured according to a published protocol based on flow-cytometry analysis (Naundorf et al., 2002) as follows:

ADCC:

For ADCC measurements, target cells (T) were adjusted to 2.0E+05 cells/ml and labeled with 100 ng/ml Calcein AM (Molecular Probes, C-3099) in RPMI1640 medium (Pan biotech GmbH) for 2 minutes at room temperature. Residual calcein was removed by 3 washing steps in RPMI1640 medium. In parallel PBMC were prepared as source for (natural killer) effector cells (E), adjusted to 1.0E+07 and mixed with the labeled target cells to yield a final E:T-ratio of 50:1 or less, depending on the assay conditions. Cells were washed once and the cell-mix resuspended in 200 μl RPMI1640 medium containing the respective antibody at different dilutions. The plate was incubated for 4 hrs under standardized conditions at 37° C. and 5% $CO_2$ in a humidified incubator. Prior to FACS analysis cells were labeled with propidium-iodide (PI) and analyzed by flow-cytometry (Becton-Dickinson). Between 50.000 and 150.000 events were counted for each assay.

The following equation gave rise to the killing activity [in %]:

$$\frac{ED^A}{EL^A + ED^A} \times 100$$

with $ED^A$=events dead cells (calcein+PI stained cells), and $EL^A$=events living cells (calcein stained cells)

CDC:

For CDC measurements, 5.0E+04 CD38 CHO-K1 transfectants were added to a microtiter well plate (Nunc) together with a 1:4 dilution of human serum (Sigma, #S-1764) and the respective antibody. All reagents and cells were diluted in RPMI1640 medium (Pan biotech GmbH) supplemented with 10% FCS. The reaction-mix was incubated for 2 hrs under standardized conditions at 37° C. and 5% $CO_2$ in a humidified incubator. As negative controls served either heat-inactivated complement or CD38-transfectants without antibody. Cells were labeled with PI and subjected to FACS-analysis.

In total 5000 events were counted and the number of dead cells at different antibody concentrations used for the determination of EC50 values. The following equation gave rise to the killing activity [in %]:

$$\frac{ED^C}{EL^C + ED^C} \times 100$$

with $ED^C$=events dead cells (PI stained cells), and $EL^C$=events living cells (unstained)

Cytotoxicity values from a total of 12 different antibody-dilutions (1:2") in triplicates were used in ADCC and duplicates in CDC for each antibody in order obtain EC-50 values with a standard analysis software (PRISM®, Graph Pad Software).

Example 3

Generation Of Stable CD38-Transfectants And CD38 Fc-Fusion Proteins

In order to generate CD38 protein for panning and screening two different expression systems had to be established. The first strategy included the generation of CD38-Fc-fusion protein, which was purified from supernatants after transient transfection of HEK293 cells. The second strategy involved the generation of a stable CHO-K1-cell line for high CD38 surface expression to be used for selection of antibody-phages via whole cell panning.

As an initial step Jurkat cells (DSMZ ACC282) were used for the generation of cDNA (Invitrogen) followed by amplification of the entire CD38-coding sequence using primers complementary to the first 7 and the last 9 codons of CD38, respectively (primer MTE001 & MTE002rev; Table 4). Sequence analysis of the CD38-insert confirmed the published amino acid sequence by Jackson et al. (1990) except for position 49 which revealed a glutamine instead of a tyrosine as described by Nata et al. (1997). For introduction of restriction endonuclease sites and cloning into different derivatives of expression vector pcDNA3.1 (Stratagene), the purified PCR-product served as a template for the re-amplification of the entire gene (primers MTE006 & MTE007rev, Table 4) or a part (primers MTE004 & MTE009rev, Table 4) of it. In the latter case a fragment encoding for the extracellular domain (aa 45 to 300) was amplified and cloned in frame between a human Vkappa leader sequence and a human Fc-gamma 1 sequence. This vector served as expression vector for the generation of soluble CD38-Fc fusion-protein. Another pcDNA3.1-derivative without, leader-sequence was used for insertion of the CD38 full-length gene. In this case a stop codon in front of the Fc-coding region and the missing leader-sequence gave rise to CD38-surface expression. HEK293 cells were transiently transfected with the Fc-fusion protein vector for generation of soluble CD38 Fc-fusion protein and, in case of the full-length derivative, CHO-K1-cells were transfected for the generation of a stable CD38-expressing cell line.

TABLE 4

| Primer # | Sequence (5'->3') |
|---|---|
| MTE001 | ATG GCC AAC TGC GAG TTC AGC (SEQ ID NO: 25) |
| MTE002rev | TCA GAT CTC AGA TGT GCA AGA TGA ATC (SEQ ID NO: 26) |
| MTE004 | TT GGT ACC AGG TGG CGC CAG CAG TG (SEQ ID NO: 27) |
| MTE006 | TT GGT ACC ATG GCC AAC TGC GAG (SEQ ID NO: 28) |
| MTE007rev | CCG ATA **TCA*** GAT CTC AGA TGT GCA AGA TG (SEQ ID NO: 29) |
| MTE009rev | CCG ATA TC GAT CTC AGA TGT GCA AGA TG (SEQ ID NO: 30) |

*leading to a stop codon (TGA) in the sense orientation.

Example 4

Cloning, Expression And Purification Of HuCAL® IgG1

In order to express full length IgG, variable domain fragments of heavy (VH) and light chains (VL) were subcloned from Fab expression vectors into appropriate pMORPH®_hlg vectors (see FIGS. 8 to 10). Restriction endonuclease pairs BlpUMfeI (insert-preparation) and BlpllEcoRI (vector-preparation) were used for subcloning of the. VH domain fragment into pMORPH®_hIgGl. Enzyme-pairs EcoRV/HpaI (lambda-insert) and EcoRV/BsiWI (kappa-insert) were used for subcloning of the VL domain fragment into the respective pMORPH®_hIgκ_1 or pMORPH®_h_Igλ_1 vectors. Resulting IgG constructs were expressed in HEK293 cells (ATCC CRL-1573) by transient transfection using standard calcium phosphate—DNA coprecipitation technique.

IgGs were purified from cell culture supernatants by affinity chromatography via Protein A Sepharose column. Further down stream processing included a buffer exchange by gel filtration and sterile filtration of purified IgG. Quality control revealed a purity of >90% by reducing SDS-PAGE and >90% monomeric IgG as determined by analytical size exclusion chromatography. The endotoxin content of the material was determined by a kinetic LAL based assay (Cambrex European Endotoxin Testing Service, Belgium).

Example 5

Generation And Production Of Chimeric OKT10 (Chokt10; SEQ ID NOS: 23 And 24)

For the construction of chOKT10 the mouse VH and VL regions were amplified by PCR using cDNA prepared from the murine OKT10 hybridoma cell line (ECACC #87021903). A set of primers was used as published (Dattamajumdar et al., 1996; Zhou et al., 1994). PCR products were used for Topo-cloning (Invitrogen; pCRII-vector) and single colonies subjected to sequence analysis (M13 reverse primer) which revealed two different kappa light chain sequences and one heavy chain sequence. According to sequence alignments (EMBL-nucleotide sequence database) and literature (Krebber et al, 1997) one of the kappa-sequence belongs to the intrinsic repertoire of the tumor cell fusion partner X63Ag8.653 and hence does not belong to OKT10 antibody. Therefore, only the new kappa sequence and the single VH-fragment was used for further cloning. Both fragments were reamplified for the addition of restriction endonuclease sites followed by cloning into the respective pMORPH® IgG1-expression vectors. The sequences for the heavy chain (SEQ ID NO: 23) and light chain (SEQ ID NO: 24) are given in FIG. 6. HEK293 cells were transfected transiently and the supernatant analyzed in FACS for the chimeric OKT10 antibody binding to the CD38 over-expressing Raji cell line (ATCC).

Example 6

Epitope Mapping

1. Materials And Methods:

Antibodies:

The following anti-CD38 IgGs were sent for epitope mappings:

| MOR# | LOT # | FORMAT | Conc. [mg/ml]/Vol. [μl] |
|---|---|---|---|
| MOR03077 | 2CHE106_030602 | human IgG1 | 0.44/1500 |
| MOR03079 | 2APO31 | human IgG1 | 0.38/500 |
| MOR03080 | 030116_4CUE16 | human IgG1 | 2.28/200 |
| MOR03100 | 030612_6SBA6 | human IgG1 | 0.39/500 |
| CHIM. OKT10* | 030603_2CHE111 | human IgG1 | 0.83/500 |

*chimeric OKT10 consisting of human Fc and mouse variable regions.

CD38-Sequence:

The amino acid (aa) sequence (position 44-300) is based on human CD38 taken from the published sequence under SWISS-PROT primary accession number P28907. At position 49 the aa Q (instead of T) has been used for the peptide-design.

PepSpot-Analysis:

The antigen peptides were synthesized on a cellulose membrane in a stepwise manner resulting in a defined arrangement (peptide array) and are covalently bound to the cellulose membrane. Binding assays were performed directly on the peptide array.

In general an antigen peptide array is incubated with blocking buffer for several hours to reduce non-specific binding of the antibodies. The incubation with the primary (antigen peptide-binding) antibody in blocking buffer occurs followed by the incubation with the peroxidase (POD)-labelled secondary antibody, which binds selectively the primary antibody. A short T (Tween)-TBS-buffer washing directly after the incubation of the antigen peptide array with the secondary antibody followed by the first chemiluminescence experiment is made to get a first overview which antigen peptides do bind the primary antibody. Several buffer washing steps follow (T-TBS- and TBS-buffer) to reduce false positive binding (unspecific antibody binding to the cellulose membrane itself). After these washing steps the final chemiluminescence analysis is performed. The data were analysed with an imaging system showing the signal intensity (Boehringer Light units, BLU) as single measurements for each peptide. In order to evaluate non-specific binding of the secondary antibodies (anti-human IgG), these antibodies were incubated with the peptide array in the absence of primary antibodies as the first step. If the primary antibody does not show any binding to the peptides it can be directly labelled with POD, which increases the sensitivity of the system (as performed for MOR3077). In this case a conventional coupling chemistry via free amino-groups is performed.

The antigen was scanned with 13-mer peptides (11 amino acids overlap). This resulted in arrays of 123 peptides. Binding assays were performed directly on the array. The peptide-bound antibodies MOR03077, MOR03079, MOR03080, MOR03100 and chimeric OKT10 were detected using a peroxidase-labelled secondary antibody (peroxidase conjugate-goat anti-human IgG, gamma chain specific, affinity isolated antibody; Sigma-Aldrich, A6029). The mappings were performed with a chemiluminescence substrate in combination with an imaging system. Additionally, a direct POD-labelling of MOR03077 was performed in order to increase the sensitivity of the system.

2. Summary And Conclusions:

All five antibodies showed different profiles in the PepSpot analysis. A schematic summary is given in FIG. 7, which illustrates the different aa sequences of CD38 being recognized. The epitope for MOR03079 and chimeric OKT10 can clearly be considered as linear. The epitope for MOR03079 can be postulated within aa 192-206 (VSRRFAEAACDVVHV) (SEQ ID NO: 40) of CD38 whereas for chimeric OKT10 a sequence between aa 284 and 298 (FLQCVKNPEDSSCTS) (SEQ ID NO: 41) is recognized predominantly. The latter results confirm the published data for the parental murine OKT10 (Hoshino et al., 1997), which postulate its epitope between aa 280-298. Yet, for a more precise epitope definition and determination of key amino acids (main antigen-antibody interaction sites) a shortening of peptides VSRRFAEAACDVVHV (SEQ ID NO: 40) and FLQCVKNPEDSSCTS (SEQ ID NO: 41) and an alanine-scan of both should be envisaged.

The epitopes for MOR03080 and MOR03100 can be clearly considered as discontinuous since several peptides covering different sites of the protein sites were recognized. Those peptides comprise aa 82-94 and aa 158-170 for MOR03080 and aa 82-94, 142-154, 158-170, 188-200 and 280-296 for MOR03100. However, some overlaps between both epitopes can be postulated since two different sites residing within aa positions 82-94 (CQSVWDAFKGAFI (SEQ ID NO:42) peptide #20) and 158-170 (TWCGEFNTSKINY (SEQ ID NO:43); peptide #58) are recognized by both antibodies.

The epitope for MOR03077 can be considered as clearly different from the latter two and can be described as multi-segmented discontinuous epitope. The epitope includes aa 44-66, 110-122, 148-164, 186-200 and 202-224.

Example 6A

As described above, MOR03077, 03080, and 03100 recognize discontinuous epitopes, whereas the epitope of MOR03079 and OKT10 can be described as linear. Interestingly MOR03080 and MOR03100 recognize strongly peptides covering aa 280-298, which are not included in the reaction pattern of the other antibodies. The sequence of this 13 aa (amino acid) peptide is conserved between human and macaque species' CD38 (table 9) (Ferrero et al., 2004) and thus might determine the cross-reactivity of both antibodies with non-human primates' CD38. A weaker reaction of MOR03080 is shown for a second peptide (aa 158-170, (table 10), which shows a 2 aa difference to cynomolgus. Both epitopes are most heterogeneous when compared to the corresponding sequence from other species, including rat (8 or 6 aa differences), mouse (6 aa differences), rabbit (9 aa differences) and dog (7 aa differences), supporting the specific binding behaviour of said antibodies in INC with the human and non-human primate tissues that were tested. Amino acids 280-298 show also a very high homology between human and cynomolgus CD38 (only 1 aa difference at position 297), which includes the epitopes for the cross-reactive OKT10 (aa 284-298) and MOR03100 (aa 280-296). On the other hand this sequence is highly heterogeneous when compared to non-primate species exhibiting differences between 6 (rat, mouse, dog) and 9 (rabbit) aa (table 11). MOR03077 and MOR03079 specifically bind to some of the peptides tested, which exhibit between 1 and 3 aa differences to the macaque sequence and even more differences to other species, supporting , inter alia, the specific binding behaviour of said antibodies to human hCD38. An example for epitope aa 192-206 of MOR03079 is shown in table 12.

Example 7

IL-6-Release/Proliferation Assay

1. Materials And Methods:

Proliferation and a IL-6 release and also IFN-γ assays have been performed according to Ausiello et al. (2000) with the following modifications: PBMCs from different healthy donors (after obtaining informed consent) were purified by density gradient centrifugation using the Histopaque cell separation system according to the instructions of the supplier (Sigma) and cultured under standard conditions (5% CO2, 37° C.) in RPMI1640 medium, supplemented with 10% FCS and glutamine ("complete RPMI1640"). For both assays the following antibodies were used: HuCAL® anti-CD38 IgGls Mabs MOR03077, MOR03079, and MOR03080, an agonistic murine IgG2a monoclonal antibody (IB4; Malavasi et al., 1984), an irrelevant HuCAL® IgG1 antibody, a matched isotype control (murine IgG2a: anti-trinitrophenol, hapten-specific antibody; cat.#: 555571, clone G155-178; Becton Dickinson; not shown) or a medium control. For the IL-6 release assay, 1.0 E+06 PBMCs in 0.5 ml complete RPMI1640 medium were incubated for 24 hrs in a 15 ml culture tube (Falcon) in the presence of 20 μg/ml antibodies. Cell culture supernatants were harvested and analysed for IL-6 release using the Quantikine kit according to the manufacturer's protocol (R&D systems). For the proliferation assay 2.0E+05 PBMCs were incubated for 3 days in a 96-well flat bottom plate (Nunc) in the presence of 20 μg/ml antibodies. Each assay was carried out in duplicates. After 4 days BrdU was added to each well and cells incubated for an additional 24 hrs at 37° C. prior to cell fixation and DNA denaturation according to the protocol of the supplier (Roche). Incorporation of BrdU was measured via an anti-BrdU peroxidase-coupled antibody in a chemiluminescence-based setting.

2. Summary And Conclusions:

Proliferation Assay:

In addition to its catalytic activities as a cyclic ADP-ribose cyclase and hydrolase, CD38 displays the ability to transduce signals of biological relevance (Hoshino et al., 1997; Ausiello et al., 2000). Those functions can be induced in vivo by e.g. receptor-ligand interactions or by cross-linking with anti-CD38 antibodies. Those signalling events lead e.g. to calcium mobilization, lymphocyte proliferation and release of cytokines. However, this signalling is not only dependent on the antigenic epitope but might also vary from donor to donor (Ausiello et al., 2000). In the view of immunotherapy non-agonistic antibodies are preferable over agonistic antibodies. Therefore, HuCAL® anti-CD38 antibodies (Mabs MOR03077; MOR03079, MOR03080) were further characterized in a proliferation assay and IL-6- (important MM growth-factor) and IFN γ release assay in comparison to the reference antibody chOKT10 and the agonistic anti-CD38 monoclonal antibody IB4.

As demonstrated in FIG. 11 the HuCAL® anti-CD38 antibodies Mab#1, 2 and 3 as well as the reference antibody chOKT10 and corresponding negative controls showed no or only weak induction of proliferation and no IL-6/FN-γ-release as compared to the agonistic antibody 1B4.

Example 8

Clonogenic Assay

1. Materials And Methods:

PBMCs harbouring autologous CD34+/CD38+ precursor cells were isolated from healthy individuals (after Obtaining informed consent) by density gradient centrifugation using the Histopaque cell separation system according to the instructions of the supplier (Sigma) and incubated with different HuCAL® IgG1 anti-CD38 antibodies (Mabs MOR03077, MOR03079, and MOR03080) and the positive control (PC) chOKT10 at 10 μg/ml. Medium and an irrelevant HuCAL® IgG1 served as background control. Each ADCC-assay consisted of 4.0E+05 PBMCs which were incubated for 4 hrs at 37° C. in RPMI1640 medium supplemented with 10% FCS. For the clonogenic assay 2.50 ml "complete" methylcellulose (CellSystems) was inoculated with 2.5 E+05 cells from the ADCC-assay and incubated for colony-development for at least 14 days in a controlled environment (37° C.; 5% CO2). Colonies were analyzed by two independent operators and grouped into BFU-E+CFU-GEMM (erythroid burst forming units and granulocyte/erythroid/macrophage/megakaryocyte stem cells) and CFU-GM (granulocyte/macrophage stem cells).

2. Summary And Conclusions:

Since CD38-expression is not only found on immune cells within the myeloid (e.g. monocytes, granulocytes) and lymphoid lineage (e.g. activated B and T-cells; plasma cells) but also on the respective precursor cells (CD34+/CD38+), it is important that those cells are not affected by antibody-mediated killing. Therefore, a clonogenic assay was applied in order to analyse those effects on CD34+/CD38+ progenitors.

PBMCs from healthy donors were incubated with HuCAL® anti-CD38 antibodies (Mab#1, Mab#2 and Mab#3) or several controls (irrelevant HuCAL® antibody, medium and reference antibody chOKT10 as positive control) according to a standard ADCC-protocol followed by further incubation in conditioned methylcellulose for colony-development. As shown in FIG. 13 no significant reduction of colony-forming units are shown for all HuCAL® anti-CD38 antibodies as compared to an irrelevant antibody or the reference antibody.

Example 9

ADCC Assays With Different Cell-Lines And Primary Multiple Myeloma Cells

1. Materials And Methods:

Isolation and ADCC of MM-patient samples: Bone marrow aspirates were obtained from multiple myeloma patients (after obtaining informed consent). Malignant cells were purified via a standard protocol using anti-CD138 magnetic beads (Milteny Biotec) after density gradient centrifugation (Sigma). An ADCC-assay was performed as described before.

2. Summary And Conclusions:

Several cell-lines derived from different malignancies were used in ADCC in order to show the cytotoxic effect of the HuCAL® anti-CD38 antibodies on a broader spectrum of cell-lines including different origins and CD38 expression-levels. As shown in FIG. 14, all cells were killed in ADCC at constant antibody concentrations (5 μg/ml) and E:T ratios at 30:1. Cytotoxicity via ADCC was also shown for several multiple myeloma samples from patients. All HuCAL® anti-CD38 antibodies were able to perform a dose-dependent killing of MM-cells and the EC50-values varied between 0.006 and 0.249 nM (FIG. 15).

Example 9A

Cytotoxic Activity: Complement-Dependent Cytotoxicity (CDC) And Antibody-Dependent Cellular Cytotoxicity (ADCC)

Complement-Dependent Cytotoxicity (CDC)

The representative anti-hCD38 antibodies of the invention were tested in CDC on hCD38-transfectants. The resulting $EC_{50}$ values ranged from 0.41 to 13.61 nM (table 2 and table 13). Except for MOR03100 all HuCAL® anti-hCD38 showed at least a 3-fold better $EC_{50}$ value compared to the reference antibody chOKT10. In all cases maximum specific cytotoxicity varied between 75-90% . An example is shown for chOKT10 and MOR03079 in FIG. 19. Among the different tumor cell lines (Raji, RPMI8226 and LP-1) only LP-1 was susceptible to CDC-mediated lysis although to a lower extent (20-40% of specific killing). In this case $EC_{50}$ values of 5.6 and 0.55 nM could be determined for MOR03077 and MOR03079, respectively.

Antibody-Dependent Cellular Cytotoxicity (ADCC)

All four representative antibodies of the invention were able to kill MM cell lines RPMI8226 and LP-1 in a dose-dependent manner using effector cells from healthy volunteers at an E:T-ratio of 30:1. $EC_{50}$ values range from 40 pM to 1.0 nM as shown in table 2 and table 13. A number of other cell lines from different indications were included in this proof of in vitro efficacy and maximal specific killing was determined using anti-hCD38 antibodies MOR03077, MOR03079 and MOR03080. The maximal specific killing rates of up to 73% (FIG. 14) fall within the published range of ADCC results despite the fact, that different assay sets (e.g. read out) and targets have been used (Ellis et al., 1995; Flavell et al., 2001, Naundorf et al., 2003; Shinkawa et al., 2003; Hayashi et al., 2003; Golay et al., 2000; Reff et al., 1994; Santi et al., 2002; Kono et al., 2002).

Among the different cell lines used for ADCC hCD38-expression was highly variable (as determined by mean-fluorescence intensities) but no correlation could be made between the expression level and the susceptibility to ADCC (FIG. 14). However, different expression levels of hCD38 within the same cell line corresponded well with the specific killing-rates when hCD38-expression was induced or enhanced by the addition of retinoic acid (Mehta et al., 2004; data not shown). In a second proof of in vitro efficacy ADCC-mediated killing could be demonstrated for all primary MM samples (FIG. 20) derived from the bone marrow of patients after density gradient purification and enrichment by anti-CD138 beads. Additionally, a single patient sample of plasma cell leukemia which included ~90% of tumor cells after density gradient centrifugation was successfully killed. As shown in FIG. 14 strong variations in $EC_{50}$ values for the individual anti-hCD38 antibodies were observed which might be due to the heterogeneity of the primary MM material in combination with different PBMC donors. However, $EC_{50}$ values were in the same range as observed for established MM cell lines. In conclusion, all cell lines and MM samples that express hCD38 could be killed in ADCC to various extent by the anti-hCD38 antibodies and only minor differences among the HuCAL® hCD38 antibodies were found except for MOR03100 which was less efficient as judged from its $EC_{50}$ values. The reference antibody chOKT1 0 exhibited the lowest efficacy in ADCC among all tested anti-hCD38 antibodies, which is in good agreement with the affinity determinations.

Example 10

Cross-Reactivity Analysis By FACS And Immunohisto-Chemistry (IHC)

Binding of the HuCAL® antibodies to target cells is shown using FACS and IHC analysis (table 5, FIG. 17). The binding to non-target cells, such as the binding of MOR03079 to erythrocytes, could be desirable for specific therapeutic uses of the compound. One such use would be to alter the half-life of the compound through the specific interaction of the antibody to the erythrocytes. However, if a specific interaction between the therapeutic antibody and a non-target cell is undesirable, antibodies that bind target cells significantly better compared to the non-target cells could be identified and utilized. The following example characterises the recognition of the HuCAL® antibodies for target and non-target cells. In addition, cross-reactivity to these target and non-target cells of other species is characterised to identify a proper animal species for toxicity and safety studies.

1. Materials And Methods:

FACS analysis of lymphocytes: EDTA-treated blood samples were obtained from healthy humans (after obtaining informed consent), from non human primates (Rhesus, Cynomolgus and Marmoset), dogs, minipigs, rabbits, rat and mouse were subjected to density gradient centrifugation using the Histopaque cell separation system according to the instructions of the supplier (Sigma). For FACS-analysis, cells from the interphase (PBMC-fraction) and pellet (Erythrocyte-fraction) were incubated with anti-CD38 HuCAL® antibodies in different formats (fully human IgG1: MOR03077, MOR03079 and MOR03080; chimeric IgG2a [Fc gamma 2a fused to the human variable region]: MOR03077, MOR03079 and MOR03080), the reference antibody chOKT10 (ch: chimeric; human Fc gamma 1 fused to mouse variable region) and several commercially available CD38-specific murine monoclonal antibodies (OKT10 , IB4, ATI, AT13/5, HB7 and T16) as well as a matched isotype negative control). After several washes in FACS-buffer (PBS+3% FCS), bound primary antibodies were detected with phycoerythrin (PE)-labelled anti-mouse or anti-human conjugates (Jackson Research). FACS analysis was performed on the gated lymphocyte population.

FACS analysis of spleen and lymph-node cells: Animals were sacrificed and spleen and lymph-nodes were removed. Spleen and lymph-nodes were cut into small pieces (1 mm3) and passed through a steel mesh into a petri-dish containing cell-culture medium (RPMI1640, 10% FCS). In order to remove fat, cell debris and aggregates, the cells were further passed through a cotton wool column. After a microscopic check to confirm single cell-suspension, cells were washed several times and subjected to density gradient centrifugation for removal of dead cells and contaminating erythrocytes. Cells from the interphase were subjected to FACS analysis as described above.

2. Summary And Conclusions:

All HuCAL® anti-CD38 Mabs were able to detect human CD38 on lymphocytes in FACS (FIG. 17). Positive staining of erythrocytes could be demonstrated for MOR03079 and to a weaker extent by MOR03080. MOR03077 did not react with human erythrocytes. MOR03080 was cross-reactive on cynomolgus and rhesus lymphocytes and erythrocytes, whereas MOR03077 reacted with minipig and rabbit lymphocytes but not on the corresponding red blood cells. In order to confirm cross-reactivity of MOR03077 on minipig and rabbit, cells from spleen and lymph-nodes were subjected to FACS-analysis. Both additional cell-types confirmed previous results (table. 5). The cross-reactivity on rhesus and cyno as well those on minipig and rabbit could be also confirmed by mouse monoclonal antibodies OKT10 and IB4 (FIG. 17), respectively.

TABLE 5

| | Antibody[h] | | | | |
|---|---|---|---|---|---|
| Species | MAb#1 | MAb#2 | MAb#3 | OKT10 | IB4 |
| Human[a] | ++[f] | ++ | ++ | ++ | ++[d] |
| Cynomolgus Monkey[a] | – | – | ++ | ++ | –[d] |
| Rhesus Monkey[a] | – | – | ++ | ++ | n.d. |
| Baboon Monkey[e] | – | – | ++ | n.d. | n.d. |
| Marmoset Monkey[a] | – | – | – | – | –[d] |
| Dog[d] | – | – | – | – | – |
| Minipig[g] | + | – | – | – | + |
| Rabbit[g] | +/– | – | – | – | + |
| Mouse[c] | – | – | – | – | n.d. |
| Rat[b] | – | – | – | – | – |

[a]FACS: lymphocytes; IHC: spleen, lymph-nodes
[b]FACS: lymphocytes, spleen; IHC: spleen
[c]IHC: lymph nodes
[d]FACS: lymphocytes
[e]IHC: spleen, lymph-nodes
[f]IHC: negative on lymph-nodes
[g]FACS: lymphocytes, spleen, lymph-nodes
[h]Formats: Mab#1-3: chimeric: human variable domaine/murine Fc 2a
OKT10: murine MAb IgG1
IB4: murine MAb IgG2a
++: strong positive staining
+: positive staining
+/–: weak positive staining
n.d.: not determined
IHC: Immuno-histochemistry (use of cryo material)
MAb#1 = MOR03077
MAb#2 = MOR03079
MAb#3 = MOR03080

Example 10A

Analysis of hCD38 expression on human normal tissues

All representative HuCAL® anti-hCD38 antibodies of the invention reacted with tissue from the human lymphoid system (table 14) including thymus, tonsils, lymph nodes and spleen except for MOR03077 which showed no positive reaction in any of the examined human lymph node sections (n=2 donors). This may be caused by an altered accessibility of the respective hCD38 epitope in lymph nodes or weak antibody antigen interaction on this tissue specimen. In blood hCD38 expression can be detected on lymphocytes by all antibodies whereas in one case (MOR03079) hCD38-expression was also detected on human erythrocytes (n>3 donors)—although to a very low extent. The latter result may be due to the high affinity of said antibody since another anti-hCD38 antibody (MAb IB4) with comparable affinities exhibited the same FACS-shift on erythrocytes (not shown). Among the different tissues prostate was hCD38-positive for all antibodies, which stained the epithelium of prostate glandules and connective tissue. In muscle all representative anti-hCD38 antibodies were tested negative. The IHC results for cerebellum and pancreas were most heterogenous among the panel of anti-hCD38 antibodies, suggesting an altered accessibility, e.g. by conformational changes or masking, of the hCD38 molecule. Neurons in the cerebellum showed a strong hCD38 expression with the reference antibody murine OKT10 but only a very weak staining with the HuCAL® anti-hCD38 antibodies. In pancreas only MOR03100 showed a strong cytoplasmic hCD38 expression of the glandular cells within the exocrine part of the pancreas. Surprisingly, the islets of Langerhans (Antonelli et al., 2001; Maloney et al., 2002; Marchetti, 2002), which are reported to express hCD38, showed no reaction in the IHC studies. In summary, the IHC and FACS data of the HuCAL® MOR03077, 03079 and 03080 resemble those shown by an RNA dot blot analysis using human multiple tissue array (Mehta et al., 2004). Those data revealed that hCD38-expression is highest in thymus and moderate to low in spleen, lymph nodes and prostate. In all other human tissues, hCD38 expression was either absent or barely detectable.

Example 11

Treatment Of Human Myeloma Xenografts In Mice (Using The RPMI8226 Cell Line) With MOR03080

1. Establishment Of Subcutaneous Mouse Model:

A subcutaneous mouse model for the human myeloma-derived tumor cell line RPMI8226 in female C.B-17-SCID mice was established as follows by Aurigon Life Science GmbH (Tutzing, Germany): on day ~1, 0, and 1, anti-asialo GM1 polyclonal antibodies (ASGM) (WAKO-Chemicals), which deplete the xenoreactive NK-cells in the SCID mice were applied intravenously in order to deactivate any residual specific immune reactivity in C.B-17-SCID mice. On day 0, either $5\times10^6$ or $1\times10^7$ RPMI8226 tumor cells in 50 μl PBS were inoculated subcutaneously into the right flank of mice either treated with ASGM (as described above) or untreated (each group consisting of five mice). Tumor development was similar in all 4 inoculated groups with no significant difference being found for treatment with or without anti-asialo GM1 antibodies or by inoculation of different cell numbers. Tumors appear to be slowly growing with the tendency of stagnation or oscillation in size for some days. Two tumors oscillated in size during the whole period of investigation, and one tumor even regarded and disappeared totally from a peak volume of 321 $mm^3$. A treatment study with this tumor model should include a high number of tumor-inoculated animals per group.

2. Treatment With MOR03080:

2.1 Study Objective

This study was performed by Aurigon Life Science GmbH (Tutzing, Germany) to compare the anti-tumor efficacy of intraperitoneally applied antibodies (HuCAL® anti-CD38) as compared to the vehicle treatment (PBS). The human antibody hMOR03080 (isotype IgG1) was tested in different amounts and treatment schedules. In addition the chimeric antibody chMOR03080 (isotype IgG2a: a chimeric antibody comprising the variable regions of MOR03080 and murine constant regions constructed in a similar way as described in Example 5 for chimeric OKT10 (murine VH/VL and human constant regions)) was tested. The RPMI8226 cancer cell line had been chosen as a model and was inoculated subcutaneously in female SCID mice as described above. The endpoints in the study were body weight (b.w.), tumor volume and clinical signs.

2.2 Antibodies And Vehicle

The antibodies were provided ready to use to Aurigon at concentrations of 2.13 mg/ml (MOR03080 hIgG1) and 1.73 mg/ml (MOR03080 chIgG2a, and stored at -80° C. until application. The antibodies were thawed and diluted with PBS to the respective end concentration. The vehicle (PBS) was provided ready to use to Aurigon and stored at 4° C. until application.

2.3 Animal Specification

Species: mouse

Strain: Fox chase C.B-17-scid (C.B-Igh-lb/IcrTac)

Number and sex: 75 females

Supplier: Taconic M&B, Bomholtvej 10, DK-8680 Ry

Health status: SPF

Weight ordered: appr. 18 g

Acclimatization: 9 days 2.4 Tumor Cell Line

The tumor cells (RPMI8226 cell line) were grown and transported to Aurigon Life Science GmbH, where the cells were splitted and grown for another cycle. Aurigon prepared the cells for injection on the day of inoculation. The culture medium used for cell propagation was RPMI 1640 supplemented with 5% FCS, 2 mM L-Glutamin and PenStrep. The cells showed no unexpected growth rate or behaviour.

For inoculation, tumor cells were suspended in PBS and adjusted to a final concentration of $1\times10^7$ cells/50 μl in PBS. The tumor cell suspension was mixed thoroughly before being injected.

2.5 Experimental Procedure

On day 0, $1\times10^7$ RPMI8226 tumor cells were inoculated subcutaneously into the right dorsal flank of 75 SCID mice. A first group was built with 15 randomly chosen animals (group 5) directly after inoculation. This group was treated with 1 mg/kg b.w. hIgGl-MOR03080 every second day between day 14 and 36. From all other 60 animals 4 groups were built with ten animals in each group on day 31 (tumor volume of about 92 $mm^3$). Groups 1-4 were built with comparable means tumor sizes and standard deviations. An additional group of 5 animals (group 6) was chosen showing relatively small tumor volumes (tumor volume of about 50 $mm^3$) for comparison with pre-treated group 5 (all but three mice showing tumor volumes of less than 10 $mm^3$, one with about 22 $mm^3$, one with about 44 $mm^3$ and one with about 119 $mm^3$). Groups 1 to 4 were treated every second day from day 32 to day 68 with either PBS (Vehicle; group 1), 1 mg/kg b.w. hIgG1-MOR03080 (group 2) or 5 mg/kg b.w.hIgG I -MOR03080 (group 3), or with 5 mg/kg b.w. chIgG2a-MOR03080 (group 4). Group 6 did not receive any treatment (see Table 6). Tumor volumes, body weight and clinical signs were measured two times a week until end of study.

TABLE 6

| Group | No. of animals | Type of application | Substance | Schedule | Treatment dose [mg/kg] | Appl. volume [μl/kg] |
|---|---|---|---|---|---|---|
| 1 | 10 | i.p. | vehicle (PBS) | every second day between day 32 and day 68 | — | 10 |
| 2 | 10 | i.p. | MOR03080 human IgG1 | every second day between day 32 and day 68 | 1 | 10 |
| 3 | 10 | i.p. | MOR03080 human IgG1 | every second day between day 32 and day 68 | 5 | 10 |
| 4 | 10 | i.p. | MOR03080 chimeric IgG2a | every second day between day 32 and day 68 | 5 | 10 |
| 5 | 15 | i.p. | MOR03080 human IgG1 | every second day between day 14 and day 36 | 1 | 10 |
| 6 | 5 | — | — | — | — | — |

2.6 Results

Clinical Observations And Mortality

No specific tumor or substance related clinical findings or mortality were observed. In group 3 (hIgG1 5 mg/kg) four animals died during blood sampling (one on day 3, one on day 34; two on day 52). In group 4 (mulgG2a 1 mg/kg) a single animal died during blood sampling (day 34). All other animals, that died during the study have been euthanized because of the tumor size.

Body Weight Development

No drug related interference with weight development was observed in comparison to group 1 (vehicle). Body weight was markedly influenced by blood sampling in groups 3 (hIgG1 5 mg/kg) and 4 (mulgG2a 5 mg/kg). Despite such interruptions the mean weight gain of all groups was continuous.

Tumor Development (See FIG. 16)

In group 1 (vehicle) tumor growth was found in the expected rate with a slow progression. As this cell line has a pronounced standard deviation values for the largest and smallest tumor have been excluded from further statistical analysis. The tumor growth of animals in group 1 was comparable to the tumor growth in group 6 (untreated), although this group started with a lower mean tumor volume on day 31. Treatment might therefore have a slight influence on the tumor growth rate. In group 1, two mice had to be euthanized before day 83 because of the tumor size, and a further one before day 87, so that the mean value of tumor volume is no longer representative after day 80. In group 6, one mouse had to be euthanized before day 80 because of the tumor size, two mice before day 83, and a further one before day 87, so that the mean value of tumor volume is no longer representative after day 76.

In group 2, treated with 1 mg/kg b.w. of hIgGI, one animal has been excluded from further analysis, because the tumor grew into the muscular tissue and this usually enhances the speed of tumor growth. Compared with the control group 1

(vehicle) the mean tumor size started to differ significantly starting with day 45 until the end of the study. No enhanced tumor growth was observed after end of treatment (day 68).

Animals of group 3 (5 mg/kg b.w. hIgGl) revealed a marked decrease in tumor growth in comparison to group 1 (vehicle), getting statistically significant with day 38 until day 83. The mean tumor volume started to strongly regrow about two weeks after the end of treatment. One out of ten tumors disappeared at day 45 and did not regrow up to 19 days after end of treatment.

The best performance of all treatment groups starting with 92 $mm^3$ tumor volume was found in group 4 (5 mg/kg b.w. mulgG2a), where the mean tumor volume showed clear regression and tumors even disappeared in 4 animals until the end of the observation period. The difference to the mean tumor volume of group 1 (vehicle) was highly significant beginning from day 38 until the end of study.

The early treatment with 1 mg/kg b.w. hIgG1 between days 14 and 36 (group 5) revealed an early as well as long lasting effect on tumor development. One animal has been excluded from further analysis as the tumor grew into muscular tissue. On day 31, only five animals had a measurable tumor at the site of inoculation, in comparison to the rest of the inoculated animals, where only 2 out of 60 did not respond to tumor inoculation. The tumor progression was delayed of about 31 days (comparison of day 52 of control group 1 with day 83 of group 5). About 50% of the animals did not show tumors at the site of inoculation at the end of the study.

2.7 Conclusion

No specific tumor or substance related clinical findings or mortality were observed in comparison with groupl (control).

No drug related interference with weight development was observed.

Tumor growth of RPMI8226 tumor cells after treatment was reduced in the order of efficiency: hIgG1 1 mg/kg, 14-36 days every second day (group 5) >mulgG2a 5 mg/kg 32-68 days every second day (group 4) >hIgG1 5 mg/kg 32-68 days every second day (group 3) >hIgG1 1 mg/kg 32-68 days every second day (group 2). In groups 2 to 4, mean tumor volumes were again increased after end of treatment to varying extents.

This in vivo study compared the anti-tumor efficacy of intraperitoneally applied antibodies (HuCAL® anti-CD38) to the vehicle treatment (PBS). The human antibody hMOR03080 (isotype IgG1) was tested in different amounts and treatment schedules and it is assumed that the human antibodies MOR03077 and MOR03079 would lead to similar results than the tested antibody MOR03080.

Example 12

CD38 Cross-Linking

The term "control antibody" as used in connection with the present invention with respect to the specific killing correlated with CD38 cross-linking refers to any antibody which is capable of cross-linking CD38. Such antibody may be, for example, an antibody directed against CD20 or an antibody directed against CD52. Particularly preferred is the commercially available anti-CD20 antibody Rituximab, such as, for example, Rituxan® or MabThera®.

Much of the biological activity of antibody therapeutics is attributed to the induction of immune effector function (Ludwig et al., 2003). However, a number of antibodies that are currently in use for hematological malignancies, including anti-CD20 (Shan et al., 2002; Rituximab) and anti-CD52 (Rowan et al., 1998; Alemtuzumab), have shown to induce apoptosis in tumor cells directly by antigen cross-linking and this activity may contribute significantly to their clinical performance. In order to address this question for CD38, a panel of 23 different cell lines (table 7) was subjected to CD38-cross-linking by anti-CD38 antibodies MOR03077, MOR03079, MOR03080, chOKT10. The number of dead cells was calculated at timepoints 0, 4 and 24 hrs in comparison to a negative control antibody (Ly6.3) and the two positive controls anti-CD20 (Rituximab for all cell-lines; Maloney et al., 2002) and anti-MHCII for a selected panel of cell-lines; Nagy et al., 2002). Among the different cell-lines only the 2 out of 3 Burkitt's lymphoma cell-lines, Raji and Namalwa, showed anti-CD38 induced killing. FACS analysis revealed CD38 expression for all lines. CD20 expression was only found on both tested CLL, two of six ALL and all three Burkitt's lymphoma cell lines but killing via anti-CD20 cross-linking was exclusively shown for the Raji cell (table 7). A clear correlation between killing and expression was found for the anti-MHCII antibody, which may be due to a different killing mechanism (table 7). After a 24 hour incubation of Raji cells with anti-CD38 antibodies a mean specific killing of 21% was shown for MOR03077 and MOR03079, whereas the specific killing activity for MOR03080 and OKT10 was only slightly above background levels (4-5%). A specific killing activity of 9% was found for the positive control Rituximab (table 8). Highest specific killing rates of up to 77% were achieved with the anti-MHCII-specific antibody (FIG. 18). In order to enhance killing efficacy antibody concentrations were increased up to 5-fold of the initial concentration (10 μg/ml) or antibodies given repeatedly several times during the incubation period which was extended up to 168 hrs. Additionally, super cross-linking with an anti-human antibody as described for Rituximab was included in the cytotoxic assays. However, none of those additional parameters led to an increase in specific killing activity for the anti-CD38 or anti-CD20 antibodies (data not shown), which seemed to reach a maximum between 4 and 24 hours after the addition of antibody. The other Burkitt's lymphoma cell lines were either less sensitive (Namalwa) or did not show any effect (DG-75) despite a comparably high CD38 expression level (table 7). The cytotoxic potential via CD38-cross-linking could be confirmed for MOR03077 and MOR03079 on thus far 2-3 different primary MM-samples. Due to the lack of cells, only specific killing after 4 hrs could be determined. A specific killing of 21 and 24% could be shown for MOR03077 and MOR03079, respectively, whereas MOR03080 and OKT10 exhibited specific killing just above background levels (4-5; table 8). The data show, that the cytotoxic potential of CD38-antibodies by cross-linking is dependent on the antigenic epitope, which are different for all four antibodies (see also chapter "epitope mapping"). It is known that CD38 must exploit the signalling machinery of other receptors such as CD3, CD19 or MHCII e.g. by specific (lateral) interaction. Thus, depending on the antigenic epitope, the CD38 molecule is cross-linked either together with other co-receptors or differentially exposed for interaction with them in order to trigger a cytotoxic mechanism. Although the CD38-function within lymphopoesis is not understood, the signalling mechanism may be triggered by its natural ligand on stromal or epthelial cells or, alternatively, by anti-CD38 antibodies. Several in vitro studies demonstrated that ligation of CD38 by antibodies can cause a drastic cell reduction including primary CD19 B-cells from normal bone marrow, normal immature myeloid cells and leukemic cells from different ALL-and AML-patients (Kumagai et al., 1995; Todiso et al., 2000). For immature cells, the suppressive effect was more pronounced in the presence of stromal cells (Kumagai et al., 1995) suggesting that a stromal factor renders the cells sensitive to anti-CD38. Although the exact mechanism (growth inhibition or apoptosis) needs to be elucidated, for tumor cells, however, a cytotoxic mechanism seems to be triggered as indicated by the appearance of PI-sensitive cells.

TABLE 7

Overview characterization of cell-lines for CD38 cross-linking

| | | Killing by x-linking of: | | | Expression of: | | |
|---|---|---|---|---|---|---|---|
| Cells | Origin | CD38 | CD20 | MHCII | CD38 | CD20 | MHCII |
| RPMI8226 | MM | − | − | − | + | − | − |
| KMS-12-BM | | − | − | − | + | − | − |
| NCI-H929 | | − | − | − | + | − | − |
| OPM-2 | | − | − | − | + | − | − |
| KMS-11 | | − | − | + | + | − | + |
| LP-1 | | − | − | + | + | − | + |
| U266 | | − | − | +/− | +/− | − | + |
| JVM-13 | CLL | − | − | + | + | + | + |
| JVM-2 | | − | − | + | + | + | + |
| CCRF-CEM | ALL | − | − | − | + | − | − |
| Jurkat | | − | − | − | + | − | − |
| NALM-6 | | − | − | n.d. | + | − | n.d. |
| MOLT-4 | | − | − | n.d. | + | − | n.d. |
| REH | | − | − | n.d. | + | − | n.d. |
| RS4; 11 | | − | − | n.d. | + | − | n.d. |
| AML-193 | AML | − | − | − | + | +/− | − |
| OCI-AML5 | | − | − | − | + | − | + |
| NB-4 | | − | − | +/− | + | +/− | +/− |
| THP-1 | | − | − | − | + | n.d. | n.d. |
| HL-60 | | − | − | − | + | − | − |
| Raji | Burkitt's | + | +/− | + | + | + | + |
| Namalwa | lymph. | + | − | n.d. | + | +/− | n.d. |
| DG-75 | | − | − | n.d. | + | +/− | n.d. |

+: positive in expression or killing;
+/−: weak in expression or killing;
−: negative in expression or killing;
n.d.: not determined

TABLE 8

Specific killing of cell-lines by CD38 cross-linking

| Target ($EC_{50}$ & spec. kiling) | MOR03077 | MOR03079 | MOR03080 | chOKT10 | Rituximab |
|---|---|---|---|---|---|
| Raji (max. spec. killing)[a,c]: | 21% | 21% | 4% | 5% | 9% |
| Raji ($EC_{50}$)[b]: | n.d. | 0.08 nM | — | n.d. | n.d. |
| Namalwa (max. spec. Killing)[b,c]: | 11% | 18% | — | n.d. | — |
| Namalwa ($EC_{50}$)[b]: | n.d. | 0.08 nM | — | n.d. | n.d. |
| MM-samples (max. spec. Killing)[b,d]: | 21% | 24% | 4% | 5% | n.d. |

—: no effect (specific killing below 1%)
[a]mean from 7 independent assays
[b]mean from 2-3 independent assays
[c]max. spec. killing after o/n incubation
[d]max. spec. killing after 4 hrs incubation
n.d.: not determined

TABLE 9

Sequence comparisons (epitope aa 82-94; MOR03080/03100)
(SEQ ID NOS 44-49 are disclosed respectively in order of appearance)

| | CD38 aa pos. | | | | | | | | | | | | |
|---|---|---|---|---|---|---|---|---|---|---|---|---|---|
| Species | 82 | 83 | 84 | 85 | 86 | 87 | 88 | 89 | 90 | 91 | 92 | 93 | 94 |
| Human | C | Q | S | V | W | D | A | F | K | G | A | F | I |
| Cyno-molgus | C | Q | S | V | W | D | A | F | K | G | A | F | I |
| Rat | C | K | K | I | L | S | T | F | K | R | G | F | I |
| Mouse | C | Q | E | I | L | S | T | F | K | G | A | F | V |
| Rabbit | C | K | K | I | L | N | T | F | T | S | A | F | V |
| Dog | C | Q | K | I | G | K | A | F | T | S | A | F | L |

TABLE 10

Sequence comparisons (epitope aa 158-170; MOR03080)
(SEQ ID NOS 50-55 are disclosed respectively in order of appearance)

| | CD38 aa pos. | | | | | | | | | | | | |
|---|---|---|---|---|---|---|---|---|---|---|---|---|---|
| Species | 158 | 159 | 160 | 161 | 162 | 163 | 164 | 165 | 166 | 167 | 168 | 169 | 170 |
| Human | T | W | C | G | E | F | N | T | S | K | I | N | Y |
| Cynomolgus | T | W | C | G | E | F | N | T | F | E | I | N | Y |
| Rat | R | W | C | G | D | P | S | T | S | D | M | N | Y |
| Mouse | R | W | C | G | D | P | S | T | S | D | M | N | Y |
| Rabbit | V | M | C | G | D | P | R | T | S | E | V | K | E |
| Dog | K | W | C | G | D | T | S S | S | E | M | N | Y | |

TABLE 11

Sequence comparisons (epitope aa 280-296: MOR03100/OKT10)
(SEQ ID NOS 56-61 are disclosed respectively in order of appearance)

| Species | CD38 aa pos. | | | | | | | | | | | | | | | | | | |
|---|---|---|---|---|---|---|---|---|---|---|---|---|---|---|---|---|---|---|---|
| | 280 | 281 | 282 | 283 | 284 | 285 | 286 | 287 | 288 | 289 | 290 | 291 | 292 | 293 | 294 | 295 | 296 | 297 | 298 |
| Human | R | P | D | K | F | L | Q | C | V | K | N | P | E | D | S | S | C | T | S |
| Cynomolgus | R | P | D | K | F | L | Q | C | V | K | N | P | E | D | S | S | C | L | S |
| Rat | R | P | V | R | F | L | Q | C | V | K | N | P | E | H | P | S | C | R | L |
| Mouse | R | P | A | R | F | L | Q | C | V | K | N | P | E | H | P | S | C | R | L |
| Rabbit | R | P | A | R | F | V | Q | C | V | R | H | P | E | H | P | S | C | S | V |
| Dog | R | P | V | R | L | L | Q | C | V | K | N | P | E | H | S | S | C | K | Y |

TABLE 12

Sequence comparisons (epitope aa 192-206; MOR03079)
(SEQ ID NOS 62-67 are disclosed respectively in order of appearance)

| Species | CD38 aa pos. | | | | | | | | | | | | | | |
|---|---|---|---|---|---|---|---|---|---|---|---|---|---|---|---|
| | 192 | 193 | 194 | 195 | 196 | 197 | 198 | 199 | 200 | 201 | 202 | 203 | 204 | 205 | 206 |
| Human | V | S | R | R | F | A | E | A | A | C | D | V | V | H | V |
| Cynomolgus | V | S | R | R | F | A | E | T | A | C | G | V | V | H | V |
| Rat | I | S | Q | K | F | A | E | D | A | C | G | V | V | Q | V |
| Mouse | I | S | Q | K | F | A | E | D | A | C | G | V | V | Q | V |
| Rabbit | V | S | R | K | F | A | E | S | A | C | G | T | V | Y | V |
| Dog | V | S | K | R | F | A | E | D | A | C | G | V | V | H | V |

TABLE 13

$EC_{50}$ in ADCC and CDC

| Antibody | ADCC $EC_{50}$ values in [nM] Targets | | | CDC $EC_{50}$ values in [nM] |
|---|---|---|---|---|
| | LP-1 | RPMI8226[b] | MM Samples[e] | CHO hCD38-transfectants |
| MOR03077 | 0.60[b] | 0.08 | 0.08 | 0.94[c] |
| MOR03079 | 0.09[b] | 0.04 | 0.112-0.202 | 0.41[b] |
| MOR03080 | 0.17[a] | 0.05 | 0.006-0.185 | 2.93[c] |

TABLE 13-continued $EC_{50}$ in ADCC and CDC

| Antibody | ADCC $EC_{50}$ values in [nM] Targets | | | CDC $EC_{50}$ values in [nM] |
|---|---|---|---|---|
| | LP-1 | RPMI8226[b] | MM Samples[e] | CHO hCD38-transfectants |
| MOR03100 | 1.00[a] | 0.28 | 0.03-0.252 | 13.61[d] |
| chOKT10 | 5.23[b] | 4.1 | 0.301-0.356 | 9.3[b] |

[a]single determination
[b]mean from 2 independent $EC_{50}$ determinations
[c]mean from 3 independent $EC_{50}$ determinations
[d]mean from 4 independent $EC_{50}$ determinations
[e]range from at least 2 independent $EC_{50}$ determinations; purified primary MM-cells

TABLE 14

IHC and FACS-analysis on normal human cells and tissues

| Tissues | Antibody & Analysis | | | | | |
|---|---|---|---|---|---|---|
| | MOR03077 | MOR03079 | MOR03080 | MOR03100 | OKT10 | Analysis |
| Erythrocytes | − | +/− | − | − | − | FACS |
| Lymphocytes | + | + | + | + | + | FACS |
| Thymocytes | + | + | + | + | + | FACS |
| Muscle | − | − | − | − | − | IHC |
| Cerebellum | +/− | +/− | +/− | +/− | ++ | IHC |
| Pancreas | − | − | − | ++ | − | IHC |
| Lymph-nodes | − | + | + | + | + | IHC |
| Tonsils | + | + | + | + | + | IHC |
| Spleen | + | + | + | + | + | IHC |
| Prostate | + | + | + | + | + | IHC |
| Skin | − | − | − | − | − | IHC |

++: strong positive staining
+: positive staining
+/−: weak positive staining
IHC: use of cryo-conserved tissue

REFERENCES

Antonelli, A., Baj., G., Marchetti., P., Fallahi, P., Surico, N., Pupilli, C., Malavasi, F. , Ferrannini, P. (2001). Human anti-CD38 autoantibodies raise intracellular calcium and stimulate insulin release in human pancreatic islets. Diabetes 50: 985-991

Ausiello C. M., Urbani F., Lande R., la Sala A., Di Carlo B., Baj G., Surico N., Hilgers J., Deaglio S., Funaro A., Malavasi F. (2000) Functional topography of discrete domains of human CD38. Tissue Antigens. 2000 Dec;56(6):539-47.

Chamow, S. M., Zhang, D. Z., Tan, X. Y, Mathre, S. M., Marsters, S. A., Peers, D. H., Byrn, R. A., Ashknazi, A., Junghans, R. P (1994). humanized, bispecific immunoadhesin-antibody that retargets CD3+ effectors to kill HIV-1-infected cells. J Immunol. 1994 November 1; 153(9): 4268-80

Dattamajumdar, A. K., Jacobsen, D. P., Hood, L. E., Osman, G. E. (1996). Rapid cloning of rearranged mouse immunoglobulin variable genes. Immunogentetics 43, 141-151

Ellis J. H., Barber, K. A., Tuft, A., Hale, C., Lewis, A. P., Glennie, M. J., Stevenson, G. T., and Crowe, J. (1995). Engineered anti-CD38 monoclonal antibodies for immunotherapy of multiple myeloma. J. Immunol. 155:925-937.

Ferrero, E., Orciani, M., Vacca, P., Ortolan, E., Crovella, S., Titti, F., Saccucci, F., Malavasi, F. (2004). Characterization and phylogenetic epitope mapping of CD38 ADPR cyclase in the cynomolgus macaque. BMC Immunology 5:21

Flavell, D. J., Boehm, D. A., Noss, A., Warnes, S. L., and Flavell, S. U. Therapy of human T-cell acute lymphoblastic leukaemia with a combination of anti-CD7 and anti-CD38-saporin immunotoxins is significantly better than therapy with each individual immunotoxin, Br. J. Cancer. 84:571-578 (2001).

Funaro, A., Spagnoli, G. C., Ausiello, C. M., Alessio, M., Roggero, S., Delia, D., Zaccolo, M., and Malavasi, F. (1990) Involvement of the multilineage CD38 molecule in a unique pathway of cell activation and proliferation. J. Immunol. 145, 2390-2396.

Golay, J., Zaffaroni, Luisella, Vaccari, T., Lazzari, M., Borleri, G.-M., Bernasconi, S., Tedesco, F., Rambaldi, Al, Introna, M. (2000). Biological response of B lymphoma to anti-CD20 monoclonal antibody in vitro: CD55 and CD59 regulate complement-mediated cell lysis. Blood 95: 3900-3908.

Hayashi, T., Treon, S. P., Hideshima, T., Tai, Y-T., Akiyama, M., Richardson, R., Chauhan, D., Grewal, I. S., Anderson, K. C. (2003). Recombinant humanized anti-CD40 monoclonal antibody triggers autologous antibody-dependent cell-mediated cytotoxicity against multiple myeloma. Br. J. Heamatol. 121, 592-596.

Hoshino S., Kukimoto I., Kontani K., Inoue S., Kanda Y., Malavasi F., Katada T. (1997) Mapping of the catalytic and epitopic sites of human CD38/NAD+ glycohydrolase to a functional domain in the carboxyl terminus. J Immunol. 158(2):741-7.

Jackson D. G., Bell J.I. (1990) Isolation of a cDNA encoding the human CD38 (T10) molecule, a cell surface glycoprotein with an unusual discontinuous pattern of expression during lymphocyte differentiation. J Immunol. 144(7):2811-5.

Knappik, A., Ge, L., Honegger, A., Pack, P., Fischer, M., Wellnhofer, G., Hoess, A., Wolle, J., Pluckthun, A., and Virnekas, B. (2000). Fully synthetic human combinatorial antibody libraries (HuCAL) based on modular consensus frameworks and CDRs randomized with trinucleotides. J Mol Biol 296, 57-86.

Kono, K., Takahashi, A., Ichihara, F., Sugai, H., Fujii, H., and Matsumoto, Y. (2002). Impaired antibody-dependent cellular cytotoxicity mediated by Herceptin in patients with gastritic cancer. Cancer Res. 62, 5813-5817.

Konopleva M., Estrov Z., Zhao S., Andreeff M., Mehta K. (1998) Ligation of cell surface CD38 protein with agonistic monoclonal antibody induces a cell growth signal in myeloid leukemia cells. J Immunol. 161(9):4702-8.

Krebber, A., Bornhauser, S., Burmester, J., Honegger, A., Willuda, J., Bossard, H. R., Pliickthun, A. (1997). Reliable cloning of functional antibody variable domains from hybridomas and spleen cell repertoires employing a reengineered phage display system. J. Imm. Meth. 201, 35-55.

Krebs, B., Rauchenberger, R., Reiffert, S., Rothe, C., Tesar, M., Thomassen, E., Cao, M., Dreier, T., Fischer, D., Hoss, A., Inge, L., Knappik, A., Marget, M., Pack, P., Meng, X. Q., Schier, R., Sohlemann, P., Winter, J., Wolle, J., and Kretzschmar, T. (2001). High-throughput generation and engineering of recombinant human antibodies. J Immunol Methods 254, 67-84.

Löhning, C. (2001). Novel methods for displaying (poly) peptides/proteins on bacteriophage particles via disulfide bonds. WO 01/05950.

Malavasi, F., Caligaris-Cappio, F., Milanese, C., Dellabona, P., Richiardi, P., Carbonara, A. O. (1984). Characterization of a murine monoclonal antibody specific for human early lymphohemopoietic cells. Hum. Immunol. 9: 9-20

Maloney, D. G., Smith, B., and Rose, A. (2002). Rituximab: Mechanism of Action and Resistance. Sem. Oncol. 29, 2-9.

Marchetti, P., Antonelli, A., Lupi, R., Marselli, L., Fallahi, P., Nesti, C., Baj, G., Ferrannini, E. (2002). Prolonged in vitro exposure to autoantibodies against CD38 impairs the function and survival of human pancreatic islets. Diabetes 51, 474-477.

Mehta, K., Ocanas, L., Malavasi, f., Marks; J. W., Rosenblum, M. G (2004). Retinoic acid-induced CD38 antigen as a target for immunotoxin-mediated killing of leukemia cells. Mol. Cancer Ther. 3, 345-352

Namba, M., Otsuki, T., Mori, M., Togawa, A., Wada, H., Sugihara, T., Yawata, Y., Kimoto, T. (1989). Establishment of five human myeloma cell lines. In Vitro Cell Dev. Biol. 25: 723.

Nata K., Takamura T., Karasawa T., Kumagai T., Hashioka W., Tohgo A., Yonekura H., Takasawa S., Nakamura S., Okamoto H. (1997). Human gene encoding CD38 (ADP-ribosyl cyclase/cyclic ADP-ribose hydrolase): organization, nucleotide sequence and alternative splicing. Gene 186(2):285-92.

Naundorf, S., Preithner, S., Mayer, P., Lippold, S., Wolf, A., Hanakam, F., Fichtner, I., Kufer, P., Raum, T., Riethmuller, G., Baeuerle, P.A., Dreier, T. (2002). Int. J. Cancer 100, 101-110.

Plückthun A, and Pack P. (1997) New protein engineering approaches to multivalent and bispecific antibody fragments. Immunotechnology 3(2):83-105.

Rauchenberger R., Borges E., Thomassen-Wolf E., Rom E., Adar R., Yaniv Y., Malka M., Chumakov I., Kotzer S., Resnitzky D., Knappik A., Reiffert S., Prassler J., Jury K., Waldherr D., Bauer S., Kretzschmar T., Yayon A., Rothe C. (2003). Human combinatorial Fab library yielding specific and functional antibodies against the human fibroblast growth factor receptor 3. J Biol Chem. 278(40):38194-205.

Reff, M. E., Carner, K., Chambers, K. S., Chinn, P. C., Leonard, J. E., Raab, R., Newman, R. A., Hanna, N., Anderson, D. R. (1994). Depletion of B cells in vivo by a chimeric mouse human monoclonal antibody to CD20. Blood 83: 435-445

Santin, A. D., Bellone, S., Gokden, M., Palmieri, M., Dunn, D., Agha, J., Roman, J. J., Hutchins, L., Pecorelli, S., O'Brian, T., Cannon, M. J., Parham, G. P. (2002). Overexpression of HER-2/Neu in Uterine serous papillary cancer. Cl. Cancer Res. 8: 1271-1279.

Shinkawa, T., Nakamura, K., Yamane, N., Shoji-Hosaka, E., Kanda, Y., Sakurada, M., Uchida, K., Anazawa, H., Satoh, M., Yamasaki, M., Hanai, N., Shitara, K. (2003). The absence of fucose but Not the presence of galactose or bisectin N-Acteylglucosamine of human IgG1 complex-type oligoscaccharides shows the critical role of enhancing antibody-dependent cellular cytotoxicity. J. Biol. Chem. 278, 3466-3473.

Zhou, H., Fisher, R. J., Papas, T. S. (1994). Optimization of primer sequences for mouse scFv repertoire display library construction. Nucleic Acids Res. 22: 888-889.

The invention claimed is:

1. A method for treating a hematologic cancer associated with the undesired presence of CD38+ cells comprising administering to a subject in need thereof an effective amount of a pharmaceutical composition comprising an isolated human or humanized antibody or functional fragment thereof specific for CD38 wherein said antibody or fragment thereof binds an epitope of CD38 that contains one or more amino acid residues within 192-206 of SEQ ID NO: 22 and a pharmaceutically acceptable carrier or excipient.

2. A method for treating a hematologic cancer associated with the undesired presence of CD38+ cells comprising administering to a subject in need thereof an effective amount of a pharmaceutical composition comprising an isolated human or humanized antibody or functional fragment thereof specific for CD38 wherein said antibody or fragment thereof binds an epitope of CD38 that contains one or more amino acid residues within 44-66, 110-122, 148-164, 186-200, and 202-224 of SEQ ID NO: 22 and a pharmaceutically acceptable carrier or excipient.

3. A method for treating a hematologic cancer associated with the undesired presence of CD38+ cells comprising administering to a subject in need thereof an effective amount of a pharmaceutical composition comprising an isolated human or humanized antibody or functional fragment thereof specific for CD38 wherein said antibody or fragment thereof binds an epitope of CD38 that contains one or more amino acid residues within 82-94 and 158-170 of SEQ ID NO: 22 and a pharmaceutically acceptable carrier or excipient.

4. A The method for treating a hematologic cancer associated with the undesired presence of CD38+ cells comprising administering to a subject in need thereof an effective amount of a pharmaceutical composition comprising an isolated human or humanized antibody or functional fragment thereof specific for CD38 wherein said antibody or fragment thereof binds an epitope of CD38 that contains one or more amino acid residues within 82-94, 142-154, 158-170, 188-200, and 280-296 of SEQ ID NO: 22 and a pharmaceutically acceptable carrier or excipient.

5. The method according to any one of claim 1, 2, 3 or 4, wherein said hematologic cancer is multiple myeloma, chronic lymphocytic leukemia, chronic myelogenous leukemia, acute myelogenous leukemia, or acute lymphocytic leukemia.

6. The method of claim 5, wherein said hematologic cancer is multiple myeloma.

7. The method of claim 5, wherein said hematologic cancer is chronic lymphocytic leukemia.

8. The method of claim 5, wherein said hematologic cancer is chronic myelogenous leukemia.

9. The method of claim 5, wherein said hematologic cancer is acute myelogenous leukemia.

10. The method of claim 5, wherein said hematologic cancer is acute lymphocytic leukemia.

11. The method according to any one of claim 1, 2, 3 or 4, wherein said antibody is an IgG.

12. The method of claim 11, wherein said antibody is an IgG1.

13. The method according to any one of claim 1, 2, 3 or 4, wherein said fragment is a Fab.

14. The method according to any one of claim 1, 2, 3 or 4, wherein said fragment is a scFv.

15. The method according to any one of claim 1, 2, 3 or , wherein said antibody or fragment thereof is human.

* * * * *

UNITED STATES PATENT AND TRADEMARK OFFICE

CERTIFICATE OF CORRECTION

PATENT NO. : 9,200,061 B2
APPLICATION NO. : 13/302195
DATED : December 1, 2015
INVENTOR(S) : Michael Tesar and Ute Jaeger It is certified that error appears in the above-identified patent and that said Letters Patent is hereby corrected as shown below:

Title Page

| Title | Current | Should be |
|---|---|---|
| | "...HUMAN CD3l" | -- ...HUMAN CD38 -- |

Claims

| Claim | Line | Current | Should be |
|---|---|---|---|
| 4 | 1 | "A The method..." | -- A method -- |
| 15 | 1 | "one of claim 1, 2, 3 or , wherein..." | -- one of claim 1, 2, 3 or 4, wherein -- |

Signed and Sealed this
Tenth Day of May, 2016

Michelle K. Lee
*Director of the United States Patent and Trademark Office*